(12) United States Patent
Becker et al.

(10) Patent No.: US 7,968,538 B2
(45) Date of Patent: Jun. 28, 2011

(54) SUBSTITUTED ARYLAMINE COMPOUNDS AND METHODS OF TREATMENT

(75) Inventors: Oren Becker, Mevaseret Zion (IL); Rosa Melendez, Woburn, MA (US); Yael Marantz, Kadima (IL); Anurag Sharadendu, Bedford, MA (US); Merav Fichman, Modi'in (IL); Mercedes Lobera, Concord, MA (US); Hanoch Senderowitz, Tel Aviv (IL); Srinivasa Rao Cheruku, Lexington, MA (US); Silvia Noiman, Herzliya (IL); Xiang Y. Yu, Acton, MA (US); Sharon Shacham, Newton, MA (US); Laurence Wu, Tainan (TW); Ashis Saha, Stow, MA (US); Pini Orbach, Needham, MA (US); Dale S. Dhanoa, Delmar, CA (US)

(73) Assignee: Galenea Corp., Cambridge, MA (US)

( * ) Notice: Subject to any disclaimer, the term of this patent is extended or adjusted under 35 U.S.C. 154(b) by 504 days.

(21) Appl. No.: 11/340,079

(22) Filed: Jan. 25, 2006

(65) Prior Publication Data

US 2006/0205737 A1    Sep. 14, 2006

Related U.S. Application Data

(60) Provisional application No. 60/701,853, filed on Jul. 22, 2005, provisional application No. 60/646,957, filed on Jan. 25, 2005.

(51) Int. Cl.
*C07D 295/135* (2006.01)
*A61K 31/451* (2006.01)

(52) U.S. Cl. ............ 514/218; 514/252.12; 514/254.11; 514/255.03; 540/575; 544/395; 544/398; 544/402

(58) Field of Classification Search .................. None
See application file for complete search history.

(56) References Cited

U.S. PATENT DOCUMENTS

| | | | |
|---|---|---|---|
| 3,236,891 A * | 2/1966 | Seemuller | 564/367 |
| 5,332,739 A | 7/1994 | Katakami et al. | |
| 5,627,077 A | 5/1997 | Dyllick-Brenzinger et al. | |
| 5,888,941 A | 3/1999 | Bartroli et al. | |
| 6,391,871 B1 | 5/2002 | Olney et al. | |
| 6,455,544 B1 | 9/2002 | Friedhoff et al. | |
| 6,579,870 B2 * | 6/2003 | Jacobsen et al. | 514/218 |
| 6,608,088 B1 | 8/2003 | Nicolodi et al. | |
| 6,610,713 B2 | 8/2003 | Tracey | |
| 6,972,287 B1 | 12/2005 | Augelli-Szafran et al. | |
| 7,030,240 B2 | 4/2006 | Dhanoa et al. | |
| 7,105,540 B2 | 9/2006 | Friedhoff et al. | |
| 7,153,858 B2 | 12/2006 | Dhanoa et al. | |
| 7,407,966 B2 | 8/2008 | Dhanoa et al. | |
| 2003/0095958 A1 * | 5/2003 | Bhisetti et al. | 424/94.1 |
| 2004/0076648 A1 | 4/2004 | Williams et al. | |
| 2004/0122090 A1 | 6/2004 | Lipton | |
| 2004/0220235 A1 | 11/2004 | Augelli-Szafran et al. | |
| 2005/0143350 A1 | 6/2005 | Seed | |
| 2005/0209218 A1 | 9/2005 | Meyerson et al. | |
| 2005/0222093 A1 | 10/2005 | Pearlman et al. | |
| 2005/0222175 A1 | 10/2005 | Dhanoa et al. | |
| 2005/0222176 A1 | 10/2005 | Dhanoa et al. | |
| 2005/0256153 A1 | 11/2005 | Dhanoa et al. | |
| 2006/0018839 A1 | 1/2006 | Ieni et al. | |
| 2006/0063810 A1 | 3/2006 | Vergez et al. | |
| 2006/0069094 A1 | 3/2006 | Bonhaus et al. | |
| 2006/0079547 A1 | 4/2006 | Dhanoa et al. | |
| 2006/0084805 A1 | 4/2006 | Dhanoa et al. | |
| 2006/0148721 A1 | 7/2006 | Erondu | |
| 2006/0183733 A1 | 8/2006 | Wills | |
| 2006/0194723 A1 | 8/2006 | Rabinoff | |
| 2006/0234998 A1 | 10/2006 | Dhanoa et al. | |
| 2006/0240043 A1 | 10/2006 | Meyerson et al. | |
| 2006/0270647 A1 | 11/2006 | Coric et al. | |
| 2006/0270650 A1 | 11/2006 | MacNeil et al. | |
| 2007/0004742 A1 | 1/2007 | Dhanoa et al. | |
| 2007/0173487 A1 | 7/2007 | Saha et al. | |
| 2008/0015177 A1 | 1/2008 | Saha et al. | |
| 2008/0027036 A1 | 1/2008 | Burli et al. | |
| 2008/0027066 A1 | 1/2008 | Dhanoa et al. | |
| 2008/0176854 A1 * | 7/2008 | Aschenbrenner et al. | 514/252.02 |
| 2009/0042904 A1 * | 2/2009 | Aschenbrenner et al. | 514/254.05 |

FOREIGN PATENT DOCUMENTS

| | | | |
|---|---|---|---|
| CA | 2512243 | * | 9/2004 |
| WO | WO-00/40554 | | 7/2000 |
| WO | WO 00/78728 | | 12/2000 |
| WO | 0198279 A2 | | 12/2001 |
| WO | WO 01/98279 | | 12/2001 |
| WO | WO 02/092585 | | 11/2002 |
| WO | WO 2003/024448 | * | 3/2003 |
| WO | WO 03/080060 | * | 10/2003 |
| WO | WO 2004/009600 | | 1/2004 |
| WO | WO 2004/078732 | | 9/2004 |
| WO | WO 2005/013977 | | 2/2005 |
| WO | 2005116025 A2 | | 12/2005 |

(Continued)

OTHER PUBLICATIONS

Zotova et al., Russian Journal of Organic Chemistry, 41(2), 214-217, 2005.*
Machii et al., Chemical Abstracts, 139:307788, 2003.*
Watanabe et al., Chemical Abstracts, 124:202301, 1996.*
Ye et al., Bioorganic and Medicinal Chemistry Letters, 14, 761-765, 2004.*
Bentley, J.C., et al., "5-$HT_6$ Antisense Oligonucleotide I.C.V. Affects Rat Performance in the Water Maze and Feeding," J. Psychopharmacol. Suppl. A64, p. 255.
Bentley, J.C., et al., "Effect of the 5-$HT_6$ Antagonist, Ro 04-6790 On Food Consumption in Rats Trained to a Fixed Feeding Regime," (1999) Br J Pharmac. Suppl. 126 p. 66.

(Continued)

*Primary Examiner* — Fiona T Powers

(74) *Attorney, Agent, or Firm* — Lando & Anastasi, LLP

(57) ABSTRACT

The invention relates to 5-$HT_6$ receptor antagonists. Novel arylamine compounds and use of these compounds and their pharmaceutical compositions, e.g., in the treatment, modulation and/or prevention of physiological conditions associated with serotonin action, such as in treating obesity, and obesity-related disorders, e.g., cardiovascular disease, digestive disease, respiratory disease, cancer and type II diabetes; and psychological disorders such as schizophrenia, are disclosed.

60 Claims, 6 Drawing Sheets

FOREIGN PATENT DOCUMENTS

| WO | WO 2005/116025 | 12/2005 |
|---|---|---|
| WO | WO-2006/071960 | 7/2006 |

OTHER PUBLICATIONS

Database Registry [Online] Chemical Abstracts Service, Columbus, OH, US; Chemical Library; Supplier: TimTec, Inc., Jul. 29, 2004, XP002383373.

Database Registry [Online], Chemical Abstracts Service, Columbus, Ohio, US; Chemical Library; Supplier: TOSLab, Jun. 14, 2002, XP002383407.

Database Registry [Online], Chemical Abstracts Service, Columbus, Ohio, US; Chemical Library; Supplier: TimeTec, Inc., Sep. 28, 2001, XP002383408.

Database Registry [Online], Chemical Abstracts Service, Columbus, Ohio, US; Chemical Library; Supplier: Chem Bridge Corp., Sep. 28, 2001, XP002383409.

Database Registry [Online], Chemical Abstracts Service, Columbus, Ohio, US; Chemical Library; Supplier: MicroChemistry Ltd., Jul. 22, 2001, XP002383410.

Database Registry [Online] Chemical Abstracts Service, Columbus, Ohio, US; Chemical Library; Supplier: MicroChemistry Ltd. Jul. 22, 2001, XP 002385315.

Database Registry [Online], Chemical Abstracts Service, Columbus, Ohio, US; Chemical Library; Supplier: Interbioscreen Ltd., Jul. 22, 2001, XP002383411.

Database Registry [Online], Chemical Abstracts Service, Columbus, Ohio, US; Chemical Library; Supplier: Scientific Exchange, Jul. 19, 2001, XP002383412.

Database Registry [Online], Chemical Abstracts Service, Columbus, Ohio, US; Chemical Library; Supplier: MicroChemistry Ltd. Apr. 5, 2001, XP002383413.

Database Registry [Online], Chemical Abstracts Service, Columbus, Ohio, US; Chemical Library; Supplier: ChemDiv., Inc., Jan. 3, 2001, XP002383414.

Holenz, Jorg, et al., "Medicinal Chemistry Driven Approaches Toward Novel and Selective Serotonin 5-$HT_6$ Receptor Ligants," J Med Chem. 2005, 48, 1781-1795.

Isaac, Methvin, et al., "6-Bicyclopiperazinyl-1-arylsulfonylindoles and 6-Bicyclopiperidinyl-1-Arylsulfonylindoles Derivatives as Novel, Potent, and Selective 5-$HT_6$ Receptor Antagonists," (2000) Bioorganic & Medicinal Chemistry Letters 10: 1719-1721.

Ruat, M., et al. "A Novel Rat Serotinin (5-$HT_6$) Receptor: Molecular Cloning, Localization and Stimulation of $_c$AMP Accumulation," (1993) Biochem Biophys. Res. Commun. 193: 268-276.

Sebben, Michele, et al., "5-$HT_6$ Receptors Positively Coupled to Adenylyl Cyclase in Striatal Neurones in Culture," (1994) NeuroReport 5: 2553-2557.

International Search Report, International Application No. PCT/US2006/002718, mailed Jul. 5, 2006.

PCT International Preliminary Report on Patentability, International Application No. PCT/US2006/002718, issued Jul. 31, 2007.

\* cited by examiner

SUBSTITUTED ARYLAMINE COMPOUNDS AND METHODS OF TREATMENT

RELATED APPLICATIONS

This application claims the benefit of priority under 35 U.S.C. 119(e) to pending U.S. Patent Application Nos. 60/646,957, filed on Jan. 25, 2005; and 60/701,853, filed Jul. 22, 2005, each of which is incorporated by reference in its entirety.

FIELD OF THE INVENTION

The invention generally relates to the field of serotonin (5-hydroxytryptamine, or 5-HT) receptor modulators, e.g., $5\text{-HT}_6$ antagonists, agonists, inverse agonists, or partial agonists, and more particularly to new substituted arylamine compounds, the synthesis and use of these compounds and their pharmaceutical compositions, e.g., in the treatment, modulation and/or prevention of physiological or psychological conditions.

BACKGROUND OF THE INVENTION

The serotonergic neural system of the brain has been shown to influence a variety of physiologic functions which manifest themselves in a variety of disorders such as Alzheimer's disease, cognition disorders, irritable bowel syndrome, nausea, emesis, vomiting, prokinesia, gastroesophageal reflux disease, nonulcer dyspepsia, depression, anxiety, urinary incontinence, migraine, arrhythmia, atrial fibrillation, ischemic stroke, gastritis, gastric emptying disorders, feeding disorders, gastrointestinal disorders, constipation, erectile dysfunction, and respiratory depression.

Obesity is a condition characterized by an increase in body fat content resulting in excess body weight above accepted norms. Obesity is the most important nutritional disorder in the western world and represents a major health problem in all industrialized countries. This disorder leads to increased mortality due to increased incidences of diseases such as cardiovascular disease, digestive disease, respiratory disease, cancer and type II diabetes. One area of obesity research has been investigating the activation of serotonergic systems, either by direct activation of serotonin receptor subtypes or by inhibiting serotonin reuptake.

Multiple serotonin (5-hydroxytryptamine or 5-HT) serotonin receptor subtypes have been identified and cloned. One of these, the $5\text{-HT}_6$ receptor, has been cloned by several groups (see, e.g., Ruat, M. et al. (1993) *Biochem. Biophys. Res. Commun.* 193: 268-276; Sebben, M. et al. (1994) *NeuroReport* 5: 2553-2557). The $5\text{-HT}_6$ receptor (5-HT6R) is positively coupled to adenylyl cyclase and regulates several neurotransmitter systems including glutamate, aspartate and acetylcholine. 5-HT6Rs have been mainly localized in olfactory tubercles, striatum, nucleus accumbens, and hippocampus with lower levels also found in amygdala and hypothalamus. Recent reports demonstrated a hypophagic effect for 5-HT6 antagonists in rats that was associated with an enhancement of the satiety sequence. The effect of $5\text{-HT}_6$ antagonists and $5\text{-HT}_6$ antisense oligonucleotides to reduce food intake in rats has been reported (Bentley, J. C. et al. (1999) *Br J Pharmac. Suppl.* 126. P66; Bentley, J. C. et al. (1997) *J. Psychopharmacol. Suppl. A*64, 2155). Compounds with enhanced affinity and selectivity for the $5\text{-HT}_6$ receptor have been identified in a number of studies, e.g., by Isaac, M. et al. (2000) *Bioorganic & Medicinal Chemistry Letters* 10: 1719-1721); and in patent publications such as WO 00/34242, WO99/37623, WO 99/42465, and WO 99/02502. $5\text{-HT}_6$ mRNA appears to be almost exclusively present in the brain with little evidence for its presence in peripheral tissues. Therefore, $5\text{-HT}_6$ antagonism has been proposed as a promising approach for treating cognitive impairment associated with neuropsychiatric disorders (e.g., Alzheimer.s disease, schizophrenia) without having potential peripheral side effects.

$5\text{-HT}_6\text{R}$ is associated with schizophrenia, bipolar affective disorders, Parkinson's and Alzheimer's disease. Furthermore, this receptor displays affinity for antidepressants such as clozapine. 5-HT is thought to be involved in schizophrenia because hallucinogens are induced by LSD, a known $5\text{-HT}_{2A}$ agonist. Clozapine blocks the $5\text{-HT}_2$ subtype of serotonin receptor. It has been found that in schizophrenia, there is a reduced number of $5\text{-HT}_{2A}$ receptors and an increase in the number of $5\text{-HT}_{1A}$ receptors in the frontal cortex.

The dopamine $D_3$ receptor is abundant in the mesolimbic and mesocortical dopamine terminal areas that are known to play a role in learning and memory. Polymorphism of the receptor has been associated with a small increase in vulnerability to schizophrenia. Moreover, there is increasingly strong evidence that $D_3$ receptor antagonists will be effective antipsychotic agents, mainly by ameliorating the negative and cognitive symptoms of schizophrenia. Selective $D_3$ receptor antagonists, such as nafadotride, reverse a scopolamine-induced deficit in both the passive avoidance paradigm and a spatial learning task in a water maze labyrinth in the rat, without having any detrimental effect on memory in non-impaired rats. The dopamine $D_3$ receptor is therefore also considered to a potential therapeutic target for improving the cognitive impairments frequently seen in schizophrenia. The effect of combined blockade of $5\text{-HT}_6$ and dopamine $D_3$ receptors has not been evaluated yet because of the lack of selective HT6/D3 antagonists.

"Typical" antipsychotics (sometimes referred to as conventional antipsychotics or conventional neuroleptics) include molindone, perphenazine, pimozide, thioridazine, thiothixene, trifluoperazine, chlorpromazine, fluphenazine, haloperidol, loxapine, and mesoridazine. Disadvantages with typical antipsychotics are well-known, e.g., 30-40% of patients do not respond during an acute schizophrenic episode; they are largely ineffective against the negative symptoms of schizophrenia; they are associated with medication compliance problems; up to 40% of patients will relapse within two years despite prophylaxis; and up to 75% of patients will experience extrapyramidal side-effects (EPSE); 5% of patients per year will develop tardive dyskinesia. Typical antipsychotics are generally being replaced by atypical antipsychotics (also known as second generation antipsychotics.)) The Atypical drugs include: aripiprazole, clozapine, olanzapine, quetiapine, risperidone, and ziprasidone. These drugs are generally better tolerated than conventional drug therapy; have a lower observed rate of EPSE; are at least as clinically effective as conventional drug therapy; and have the potential to influence negative symptoms. Also, some studies indicate a modest improvement in cognition. But while the atypical drugs are an improvement over conventional antispsychotics, they are not without side effects, which include: drowsiness and weight gain; possible increase in the risk of type II diabetes and high levels of triglycerides in the blood; muscle tremor, uncontrolled movements of the face and arms (tardive dyskinesia), and muscle damage. Newer antipsychotics are less likely to cause tremor, muscle stiffness, uncontrolled movements, and fever and muscle damage. Clozapine (CLOZARIL) can cause bone marrow suppression, reduced white blood cell count, and seizures, though it is often effective in people who are not responsive to other drugs.

Clozapine and Olanzapine (ZYPREXA) are most likely to cause weight gain; Ziprasidone (GEODON) does not appear to cause weight gain, but may lead to abnormalities on electrocardiogram.

Cognitive impairment is a debilitating feature of schizophrenia. 5-$HT_6$ antagonists have positive effects on cognition; whereas current therapies for schizophrenia (see the drugs noted above) have variable effects on cognition. 30-70% of patients receiving second-generation drugs have improvement on neuropsychological tests of cognition (particularly attention and short-term memory); improvement in these functions is seen in only 30% of patients receiving first-generation drugs. It has also been noted that 5-$HT_6$ mRNA is decreased in hippocampus of post-mortem schizophrenia patients; atypical anti-psychotics (e.g., olanzapine) have high affinity for 5-$HT_6$; 5-$HT_6$ is highly expressed in dopamine-rich areas (striatum, nucleus accumbens); and 5-$HT_6$ is localized on striatal gamma-amino butyric acid (GABA)-ergic interneurons, which also receive dopaminergic input.

Targeting 5-$HT_6$R is further believed to attenuate dopamine activity (striatal) responsible for the extrapyramidal side effects of older anti-psychotics; a positive genetic association was found between the C267T polymorphism in 5-$HT_6$ and the effectiveness of clozapine in patients refractory to treatment. Thus, high affinity compounds to 5-$HT_6$R represent a real potential for treating cognitive dysfunction, e.g., in schizophrenia. A 5-$HT_6$ receptor antagonist may be used as an add-on or combination therapy with other atypical drugs (e.g., clozapine) to treat the positive, negative and cognitive symptoms of schizophrenia with no side effect such as weight gain.

SUMMARY OF THE INVENTION

The present invention relates to the discovery of new compounds which are 5-$HT_6$ modulators, e.g., agonists, inverse agonists, or partial agonists, that can be used for treating, preventing or curing 5-HT-related conditions. Compounds according to the invention have 5-$HT_6$ receptor antagonist activity and are believed to be of use in treating or preventing obesity and type II diabetes, as well as in the treatment or prophylaxis of central nervous system disorders such as anxiety, depression, panic attacks, memory disorders, sleep disorders, binge disorders, migraine, anorexia, bulimia, obsessive compulsive disorders, psychoses, Alzheimer's disease, Parkinson's disease, Huntington's chorea and/or schizophrenia, drug abuse, and Attention Deficit/Hyperactive Disorders (ADHD). Body weight and body weight gain reduction, e.g., treating body weight disorders, is achieved by, e.g., reducing food intake.

In particular, it has been found that certain compounds are effective 5-$HT_6$ receptor modulators, e.g., antagonists and/or partial and/or full agonists. In an embodiment, such compounds include arylamines having the formula

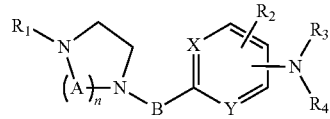

(I)

and pharmaceutically acceptable salts and/or esters thereof. n may be 0, 1, 2, 3, or 4; A, and when present (i.e., n>0) may be a lower alkyl, e.g., —$CH_2$—$CH_2$ to form a piperazine, or —$CH_2$—$CH_2$—$CH_2$— to form an azapine ring. $R_1$ may be hydrogen or substituted or unsubstituted alkyl (e.g., lower alkyl) or aryl; $R_2$ may be hydrogen; halo; nitro; cyano, lower alkoxy; carboxylate salt acid or alkyl (e.g., lower alkyl) ester thereof, e.g., $COR_5$ where $R_5$ may be unsubstituted or mono-, di- or trisubstituted phenyl, biphenyl, heterocyclic, or a fused aromatic or heterocyclic ring, e.g., naphthyl or tetrahydronaphthyl; a sulfone (e.g., $SO_2R_6$ where $R_6$ may be, e.g., substituted or unsubstituted alkyl, haloalkyl, aryl, or heteroaryl); haloalkyl or haloalkoxy, e.g., mono-, di, or trifluoromethyl or methoxy; alkylamide; acetaldehyde; carboxamide; carbomyl; alkoxyaminocarbonyl; or substituted arylalkylamino; and $R_3$ and $R_4$ may independently be hydrogen, substituted or unsubstituted alkyl (e.g., lower alkyl), aryl (substituted or unsubstituted), alkylaryl, heteroaryl or alkylheteroaryl, or, taken together, $R_3$ and $R_4$ may form a substituted or unsubstituted aryl, alkylaryl, heteroaryl or alkylheteroaryl group, e.g., unsubstituted or mono-, di- or trisubstituted phenyl, biphenyl, or a fused aromatic or heterocyclic ring, e.g., naphthyl, tetrahydronaphthyl or benzothiophene; B may be absent or present, and when present may be a lower alkyl, e.g., methylene or a carbonyl group; and X and Y may each independently be C or N; and pharmaceutically acceptable salts and/or esters thereof. When two substituents are present on adjacent carbon atoms, the substituents, e.g., on an aryl ring, taken with the aryl ring to which they are attached, may form a five to seven membered heterocyclic ring (for example, when the substituents are methoxy, a dioxane or dioxolane ring may be formed.

Compounds of the above formula also include those where $R_1$ may be, e.g., H, $CH_3$, n-propyl, c-propyl, i-butyl, t-butyl, cyclohexyl, cyclohexylmethyl, phenyl or benzyl; A may be $CH_2$, (—$CH_2$—$CH_2$—), or ($CH_2$—$CH_2$—$CH_2$—); n may be 0, 1, 2, 3, or 4; B is absent; $R_2$ may be hydrogen; nitro; lower alkoxy; a sulfone (e.g., $SO_2R_6$ where $R_6$ may be, e.g., substituted or unsubstituted alkyl, haloalkyl, aryl, or heteroaryl); haloalkyl or haloalkoxy, e.g., mono-, di, or trifluoromethyl or methoxy; alkylamide; $R_3$ and $R_4$ independently may be lower alkyl or aryl or alkylaryl; and X and Y are both C.

In another embodiment, compounds of the invention include those of the formula

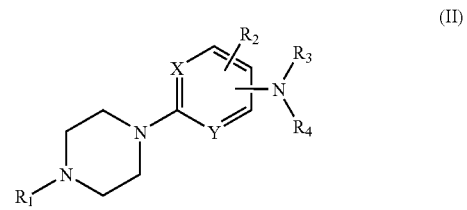

(II)

and pharmaceutically acceptable salts and/or esters thereof. $R_1$ may be hydrogen or substituted or unsubstituted alkyl (e.g., lower alkyl); $R_2$ may be hydrogen; halo; nitro; cyano, lower alkoxy; carboxylate salt acid or alkyl (e.g., lower alkyl) ester thereof; a sulfone (e.g., $SO_2R_6$ where $R_6$ may be, e.g., substituted or unsubstituted alkyl, haloalkyl, aryl, or heteroaryl); haloalkyl or haloalkoxy, e.g., mono-, di, or trifluoromethyl or methoxy; alkylamide; acetaldehyde; carboxamide; carbornyl; alkoxyaminocarbonyl; or substituted arylalkylamino; and $R_3$ and $R_4$ may independently be hydrogen, substituted or unsubstituted alkyl (e.g., lower alkyl) aryl (substituted or unsubstituted), alkylaryl, heteroaryl or alkylheteroaryl, or, taken together, $R_3$ and $R_4$ may form a substituted or unsubstituted aryl, alkylaryl, heteroaryl or alkylheteroaryl group. When two substituents are present on adjacent carbon atoms, the substituents, e.g., on an aryl ring, taken with the aryl ring to which they are attached, may form a five to seven membered heterocyclic ring (for example, when the substituents are methoxy, a dioxane or dioxolane ring may be formed.

Advantageously, compounds of the invention include N-benzyl-3-piperazinyl benzenamine compounds of the formula

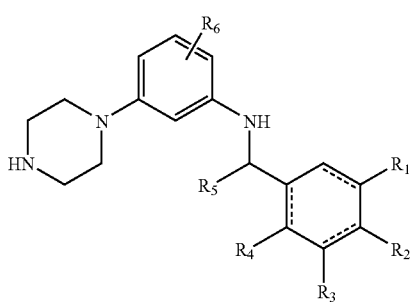

(III)

and pharmaceutically acceptable salts and/or esters thereof. $R_1$, $R_2$, $R_3$ and $R_4$ may independently be hydrogen, halo or lower alkoxy, or two adjoining $R_1$, $R_2$, $R_3$ or $R_4$ lower alkoxy groups may, taken with the benzyl ring to which they are attached, combine to form a heterocyclic ring; $R_5$ may be hydrogen or lower alkoxy; and $R_6$ may be a sulfone (e.g., $SO_2R$ where R may be, e.g., substituted or unsubstituted alkyl, haloalkyl, aryl, or heteroaryl); $NO_2$, or $COCF_3$. When two substituents are present on adjacent carbon atoms, the substituents, e.g., on an aromatic or carbocyclic ring, taken with the ring to which they are attached, may form a five to seven membered ring (for example, when the substituents are methoxy, a dioxane or dioxolane ring may be formed. Taken together, the two substituents may thus form, e.g., a substituted or unsubstituted aryl, alkylaryl, heteroaryl or alkylheteroaryl group such as unsubstituted or mono-, di- or trisubstituted phenyl, biphenyl, or a fused aromatic or heterocyclic rings, e.g., naphthyl or tetrahydronaphthyl or benzothiophene.

The invention further includes N-benzyl-3-piperazinyl compounds of the formula

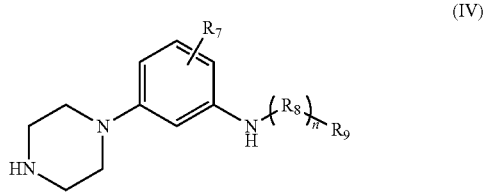

(IV)

and pharmaceutically acceptable salts and/or esters thereof. $R_7$ may be nitro; lower alkoxy, e.g., methyl; trihalo (e.g., trifluoro) methanone; sulfonyl; or alkyl (e.g., lower alkyl) sulfonyl. $R_8$ may be straight or branched $C_1$, $C_2$ or $C_3$ lower alkylene, and n is 0, 1 or 2. $R_9$ is a single or conjugated cyclic ring, e.g., substituted or unsubstituted aryl, naphthyl, or chroman. Substituents on $R_9$ may include lower alkoxy, e.g., $C_1$, $C_2$ or $C_3$; halo; lower alkyl, e.g., $C_1$, $C_2$ or $C_3$. $R_9$ may have more than one substituent, e.g., one, two, three or four. When two substituents are present on adjacent carbon atoms, the substituents, e.g., on an aromatic or carbocyclic ring, taken with the ring to which they are attached, may form a five to seven membered ring (for example, when the substituents are methoxy, a dioxane or dioxolane ring may be formed. Taken together, the two substituents may thus form, e.g., a substituted or unsubstituted aryl, alkylaryl, heteroaryl or alkylheteroaryl group such as unsubstituted or mono-, di- or trisubstituted phenyl, biphenyl, or a fused aromatic or heterocyclic rings, e.g., naphthyl or tetrahydronaphthyl or benzothiophene.

Compounds of the invention may also be 5-HT receptor modulators, e.g., 5-$HT_6$ receptor agonists, partial agonists, inverse agonists and/or antagonists.

In another embodiment compounds of the invention may also be 5-HT receptor antagonists, e.g., 5-$HT_6$ receptor antagonists.

Another aspect of the invention is a pharmaceutical composition comprising an amount of a compound according to Formula I, II, III or IV effective to treat diseases such as obesity, and obesity-related disorders, e.g., cardiovascular disease, digestive disease, respiratory disease, cancer and type II diabetes, and a pharmaceutically acceptable carrier.

Another aspect of the invention is a method for treating diseases such as obesity, and obesity-related disorders, e.g., cardiovascular disease, digestive disease, respiratory disease, cancer and type II diabetes, in a mammal such as a human comprising administering a therapeutically effective amount of a compound of Formula I, II, III or IV.

Compounds of the invention may also be 5-HT receptor modulators, e.g., 5-$HT_6$ receptor agonists, partial agonists, inverse agonists and/or antagonists.

DETAILED DESCRIPTION OF THE INVENTION

Figure 1A:
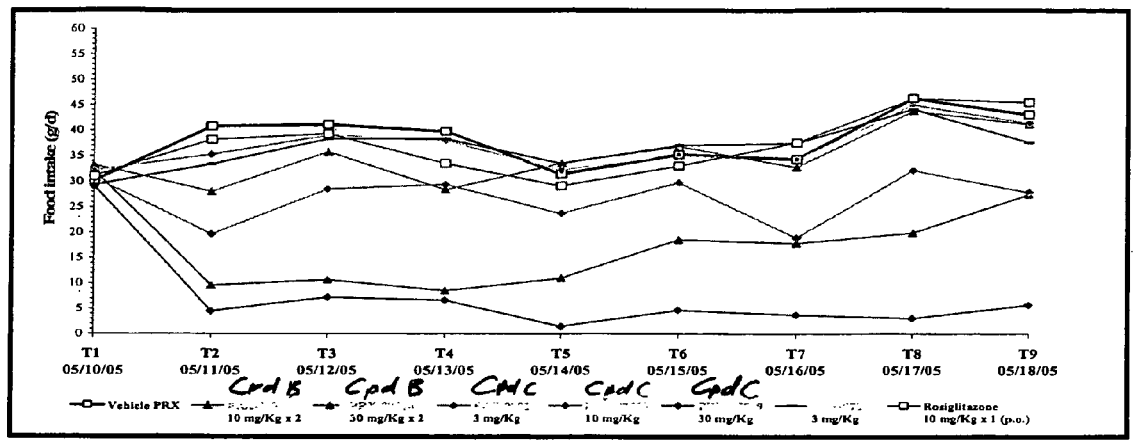
FIG. 1 shows the effect of two compounds of the invention, Compound B and Compound C, on food intake (FIG. 1A) and body weight (FIG. 1B) in ob/ob Mice.
Figure 1B:
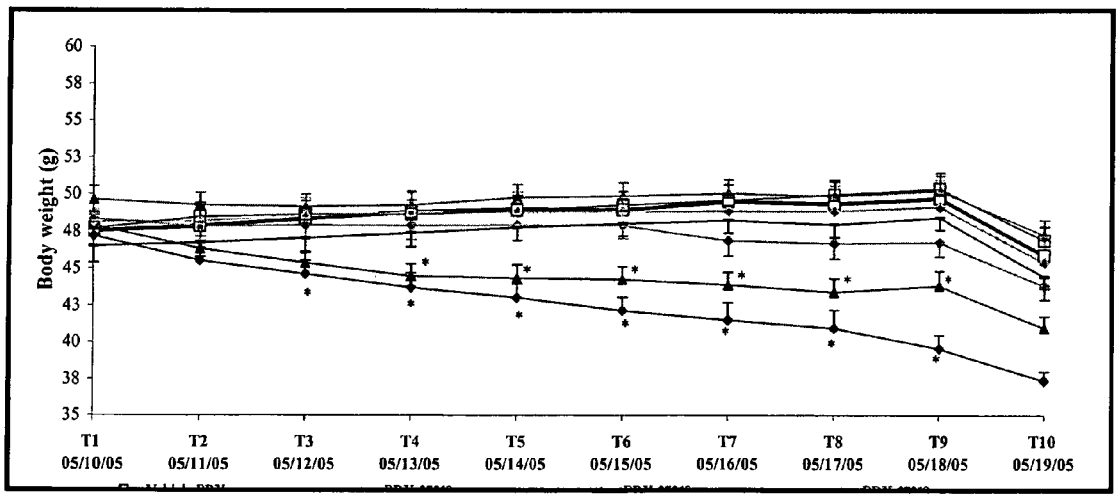

The features and other details of the invention will now be more particularly described with reference to the accompanying drawings and pointed out in the claims. It will be understood that particular embodiments described herein are shown by way of illustration and not as limitations of the invention. The principal features of this invention can be employed in various embodiments without departing from the scope of the invention. All parts and percentages are by weight unless otherwise specified.

Definitions

For convenience, certain terms used in the specification, examples, and appended claims are collected here.

"5-HT receptor modulator" or "5-HT modulator" includes compounds having effect at the $5\text{-}HT_1$, $5\text{-}HT_2$, $5\text{-}HT_3$, $5\text{-}HT_4$, $5\text{-}HT_5$, $5\text{-}HT_6$ or $5\text{-}HT_7$ receptors, including the subtypes of each receptor type, such as $5\text{-}HT_{1A,\ B,\ C,\ D,\ E\ or\ F}$; $5\text{-}HT_{2A,\ B\ or\ C}$; $h5\text{-}HT_{4a,\ b,\ c,\ d\ or\ e}$; and $5\text{-}HT_{5A\ or\ B}$. 5-HT modulators may be agonists, partial agonists, inverse agonists, or antagonists.

"Treating", includes any effect, e.g., lessening, reducing, modulating, or eliminating, that results in the improvement of the condition, disease, disorder, etc.

"Body weight disorders" includes disorders caused by an imbalance between energy intake and energy expenditure, resulting in abnormal (high) body weight, such as obesity.

"Alkyl" includes saturated aliphatic groups, including straight-chain alkyl groups (e.g., methyl, ethyl, propyl, butyl, pentyl, hexyl, heptyl, octyl, nonyl, decyl), branched-chain alkyl groups (e.g., isopropyl, tert-butyl, isobutyl), cycloalkyl (e.g., alicyclic) groups (e.g., cyclopropyl, cyclopentyl, cyclohexyl, cycloheptyl, cyclooctyl), alkyl substituted cycloalkyl groups, and cycloalkyl substituted alkyl groups. "Alkyl" further includes alkyl groups which have oxygen, nitrogen, sulfur or phosphorous atoms replacing one or more hydrocarbon backbone carbon atoms. In certain embodiments, a straight chain or branched chain alkyl has six or fewer carbon atoms in its backbone (e.g., $C_1$-$C_6$ for straight chain, $C_3$-$C_6$ for branched chain), and more preferably four or fewer. Likewise, preferred cycloalkyls have from three to eight carbon atoms in their ring structure, and more preferably have five or six carbons in the ring structure. "$C_1$-$C_6$" includes alkyl groups containing one to six carbon atoms.

The term "alkyl" also includes both "unsubstituted alkyls" and "substituted alkyls", the latter of which refers to alkyl moieties having substituents replacing a hydrogen on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)). "Alkyl" also includes the side chains of natural and unnatural amino acids.

"Aryl" includes groups with aromaticity, including 5- and 6-membered "unconjugated", or single-ring, aromatic groups that may include from zero to four heteroatoms, as well as "conjugated", or multicyclic, systems with at least one aromatic ring. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a multicyclic system (e.g., tetralin, methylenedioxyphenyl).

"Alkenyl" includes unsaturated aliphatic groups analogous in length and possible substitution to the alkyls described above, but that contain at least one double bond. For example, the term "alkenyl" includes straight-chain alkenyl groups (e.g., ethenyl, propenyl, butenyl, pentenyl, hexenyl, heptenyl, octenyl, nonenyl, decenyl), branched-chain alkenyl groups, cycloalkenyl (e.g., alicyclic) groups (e.g., cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term "alkenyl" further includes alkenyl groups which include oxygen, nitrogen, sulfur or phosphorous atoms replacing one or more hydrocarbon backbone carbons. In certain embodiments, a straight chain or branched chain alkenyl group has six or fewer carbon atoms in its backbone (e.g., $C_2$-$C_6$ for straight chain, $C_3$-$C_6$ for branched chain.) Likewise, cycloalkenyl groups may have from three to eight carbon atoms in their ring structure, and more preferably have five or six carbons in the ring structure. The term "$C_2$-$C_6$" includes alkenyl groups containing two to six carbon atoms.

The term "alkenyl" also includes both "unsubstituted alkenyls" and "substituted alkenyls", the latter of which refers to alkenyl moieties having substituents replacing a hydrogen on one or more hydrocarbon backbone carbon atoms. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Alkynyl" includes unsaturated aliphatic groups analogous in length and possible substitution to the alkyls described above, but which contain at least one triple bond. For example, "alkynyl" includes straight-chain alkynyl groups (e.g., ethynyl, propynyl, butynyl, pentynyl, hexynyl, heptynyl, octynyl, nonynyl, decynyl), branched-chain alkynyl groups, and cycloalkyl or cycloalkenyl substituted alkynyl groups. The term "alkynyl" further includes alkynyl groups having oxygen, nitrogen, sulfur or phosphorous atoms replacing one or more hydrocarbon backbone carbons. In certain embodiments, a straight chain or branched chain alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms.

The term "alkynyl" also includes both "unsubstituted alkynyls" and "substituted alkynyls", the latter of which refers to alkynyl moieties having substituents replacing a hydrogen on one or more hydrocarbon backbone carbon atoms. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, "lower alkyl" includes an alkyl group, as defined above, but having from one to ten, more preferably from one to six, carbon atoms in its backbone structure. "Lower alkenyl" and "lower alkynyl" have chain lengths of, for example, 2-5 carbon atoms.

"Acyl" includes compounds and moieties which contain the acyl radical ($CH_3CO$—) or a carbonyl group. "Substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Acylamino" includes moieties wherein an acyl moiety is bonded to an amino group. For example, the term includes alkylcarbonylamino, arylcarbonylamino, carbamoyl and ureido groups.

"Alkoxyalkyl", "alkylaminoalkyl" and "thioalkoxyalkyl" include alkyl groups, as described above, which further include oxygen, nitrogen or sulfur atoms replacing one or more hydrocarbon backbone carbon atoms, e.g., oxygen, nitrogen or sulfur atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, and trichloromethoxy.

The terms "heterocyclyl" or "heterocyclic group" include closed ring structures, e.g., 3- to 10-, or 4- to 7-membered rings, which include one or more heteroatoms. Heterocyclyl groups can be saturated or unsaturated and include pyrrolidine, oxolane, thiolane, piperidine, piperizine, morpholine, lactones, lactams such as azetidinones and pyrrolidinones, sultams, sultones, and the like. The heterocyclic ring can be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety.

The term "thiocarbonyl" or "thiocarboxy" includes compounds and moieties which contain a carbon connected with a double bond to a sulfur atom.

The term "ether" includes compounds or moieties which contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "ester" includes compounds and moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "thioether" includes compounds and moieties which contain a sulfur atom bonded to two different carbon or heteroatoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom which is bonded to an alkyl group. Similarly, the term "alkthioalkenyls" and alkthioalkynyls" refer to compounds or moieties wherein an alkyl, alkenyl, or alkynyl group is bonded to a sulfur atom which is covalently bonded to an alkynyl group.

The term "hydroxy" or "hydroxyl" includes groups with an —OH or —O$^-$.

The term "halogen" includes fluorine, bromine, chlorine, iodine, etc. The term "perhalogenated" generally refers to a moiety wherein all hydrogens are replaced by halogen atoms.

"Heteroatom" includes atoms of any element other than carbon or hydrogen. Examples of heteroatoms include nitrogen, oxygen, sulfur and phosphorus.

The present invention relates to the discovery of new compounds which are $5\text{-}HT_6$ modulators, e.g., agonists, inverse agonists, or partial agonists, that can be used for treating, preventing or curing 5-HT-related conditions. Compounds according to the invention have $5\text{-}HT_6$ receptor antagonist activity and are believed to be of use in treating or preventing obesity and type II diabetes, as well as in the treatment or prophylaxis of central nervous system disorders such as anxiety, depression, panic attacks, memory disorders, sleep disorders, binge disorders, migraine, anorexia, bulimia, obsessive compulsive disorders, psychoses, Alzheimer's disease, Parkinson's disease, Huntington's chorea and/or schizophrenia, drug abuse, and Attention Deficit/Hyperactive Disorders (ADHD). Body weight and body weight gain reduction, e.g., treating body weight disorders, is achieved by, e.g., reducing food intake.

In particular, it has been found that certain compounds are effective $5\text{-}HT_6$ receptor modulators, e.g., antagonists and/or partial and/or full agonists. In an embodiment, such compounds include arylamines having the formula

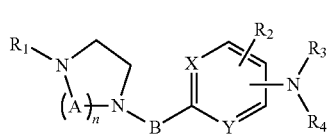

(I)

and pharmaceutically acceptable salts and/or esters thereof. n may be 0, 1, 2, 3, or 4; A, and when present (i.e., n>0) may be a lower alkyl, e.g., —$CH_2$—$CH_2$ to form a piperazine, or —$CH_2$—$CH_2$—$CH_2$— to form an azapine ring. $R_1$ may be hydrogen or substituted or unsubstituted alkyl (e.g., lower alkyl) or aryl; $R_2$ may be hydrogen; halo; nitro; cyano, lower alkoxy; carboxylate salt acid or alkyl (e.g., lower alkyl) ester thereof, e.g., $COR_5$ where $R_5$ may be unsubstituted or mono-, di- or trisubstituted phenyl, biphenyl, heterocyclic, or a fused aromatic or heterocyclic ring, e.g., naphthyl or tetrahydronaphthyl; a sulfone (e.g., $SO_2R_6$ where $R_6$ may be, e.g., substituted or unsubstituted alkyl, haloalkyl, aryl, or heteroaryl); haloalkyl or haloalkoxy, e.g., mono-, di, or trifluoromethyl or methoxy; alkylamide; acetaldehyde; carboxamide; carbornyl; alkoxyaminocarbonyl; or substituted arylalkylamino; and $R_3$ and $R_4$ may independently be hydrogen, substituted or unsubstituted alkyl (e.g., lower alkyl), aryl (substituted or unsubstituted), alkylaryl, heteroaryl or alkylheteroaryl, or, taken together, $R_3$ and $R_4$ may form a substituted or unsubstituted aryl, alkylaryl, heteroaryl or alkylheteroaryl group, e.g., unsubstituted or mono-, di- or trisubstituted phenyl, biphenyl, or a fused aromatic or heterocyclic ring, e.g., naphthyl, tetrahydronaphthyl or benzothiophene; B may be absent or present, and when present may be a lower alkyl, e.g., methylene or a carbonyl group; and X and Y may each independently be C or N; and pharmaceutically acceptable salts and/or esters thereof. When two substituents are present on adjacent carbon atoms, the substituents, e.g., on an aryl ring, taken with the aryl ring to which they are attached, may form a five to seven membered heterocyclic ring (for example, when the substituents are methoxy, a dioxane or dioxolane ring may be formed.

Compounds of the above formula also include those where $R_1$ may be, e.g., H, $CH_3$, n-propyl, c-propyl, i-butyl, t-butyl, cyclohexyl, cyclohexylmethyl, phenyl or benzyl; A may be $CH_2$, (—$CH_2$—$CH_2$—), or (—$CH_2$—$CH_2$—$CH_2$—); n may be 0, 1, 2, 3, or 4; B is absent; $R_2$ may be hydrogen; nitro; lower alkoxy; a sulfone (e.g., $SO_2R_6$ where $R_6$ may be, e.g., substituted or unsubstituted alkyl, haloalkyl, aryl, or heteroaryl); haloalkyl or haloalkoxy, e.g., mono-, di, or trifluoromethyl or methoxy; alkylamide; $R_3$ and $R_4$ independently may be lower alkyl or aryl or alkylaryl; and X and Y are both C.

and pharmaceutically acceptable salts and/or esters thereof. $R_1$ may be hydrogen or substituted or unsubstituted alkyl (e.g., lower alkyl); $R_2$ may be hydrogen; halo; nitro; cyano, lower alkoxy; carboxylate salt acid or alkyl (e.g., lower alkyl) ester thereof; a sulfone (e.g., $SO_2R_6$ where $R_6$ may be, e.g., substituted or unsubstituted alkyl, haloalkyl, aryl, or heteroaryl); haloalkyl or haloalkoxy, e.g., mono-, di, or trifluoromethyl or methoxy; alkylamide; acetaldehyde; carboxamide; carbomyl; alkoxyaminocarbonyl; or substituted arylalkylamino; and $R_3$ and $R_4$ may independently be hydrogen, substituted or unsubstituted alkyl (e.g., lower alkyl) aryl (substituted or unsubstituted), alkylaryl, heteroaryl or alkylheteroaryl, or, taken together, $R_3$ and $R_4$ may form a substituted or unsubstituted aryl, alkylaryl, heteroaryl or alkylheteroaryl group. When two substituents are present on adjacent carbon atoms, the substituents, e.g., on an aryl ring, taken with the aryl ring to which they are attached, may form a five to seven membered heterocyclic ring (for example, when the substituents are methoxy, a dioxane or dioxolane ring may be formed.

Advantageously, compounds of the invention include N-benzyl-3-piperazinyl benzenamine compounds of the formula

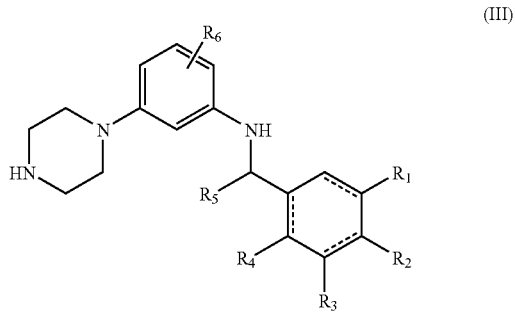

(III)

and pharmaceutically acceptable salts and/or esters thereof. $R_1$, $R_2$, $R_3$ and $R_4$ may independently be hydrogen, halo or lower alkoxy, or two adjoining $R_1$, $R_2$, $R_3$ or $R_4$ lower alkoxy groups may, taken with the benzyl ring to which they are attached, combine to form a heterocyclic ring; $R_5$ may be hydrogen or lower alkoxy; and $R_6$ may be a sulfone (e.g., $SO_2R$ where R may be, e.g., substituted or unsubstituted alkyl, haloalkyl, aryl, or heteroaryl); $NO_2$, or $COCF_3$. When two substituents are present on adjacent carbon atoms, the substituents, e.g., on an aromatic or carbocyclic ring, taken with the ring to which they are attached, may form a five to seven membered ring (for example, when the substituents are methoxy, a dioxane or dioxolane ring may be formed. Taken together, the two substituents may thus form, e.g., a substituted or unsubstituted aryl, alkylaryl, heteroaryl or alkylheteroaryl group such as unsubstituted or mono-, di- or trisubstituted phenyl, biphenyl, or a fused aromatic or heterocyclic rings, e.g., naphthyl or tetrahydronaphthyl or benzothiophene.

The invention further includes N-benzyl-3-piperazinyl compounds of the formula

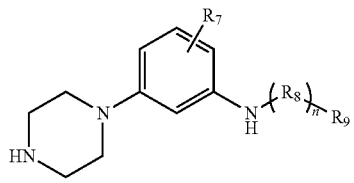

(IV)

and pharmaceutically acceptable salts and/or esters thereof. $R_7$ may be nitro; lower alkoxy, e.g., methyl; trihalo (e.g., trifluoro) methanone; sulfonyl; or alkyl (e.g., lower alkyl) sulfonyl. $R_8$ may be straight or branched $C_1$, $C_2$ or $C_3$ lower alkylene, and n is 0, 1 or 2. $R_9$ is a single or conjugated cyclic ring, e.g., substituted or unsubstituted aryl, naphthyl, or chroman. Substituents on $R_9$ may include lower alkoxy, e.g., $C_1$, $C_2$ or $C_3$; halo; lower alkyl, e.g., $C_1$, $C_2$ or $C_3$. $R_9$ may have more than one substituent, e.g., one, two, three or four. When two substituents are present on adjacent carbon atoms, the substituents, e.g., on an aromatic or carbocyclic ring, taken with the ring to which they are attached, may form a five to seven membered ring (for example, when the substituents are methoxy, a dioxane or dioxolane ring may be formed. Taken together, the two substituents may thus form, e.g., a substituted or unsubstituted aryl, alkylaryl, heteroaryl or alkylheteroaryl group such as unsubstituted or mono-, di- or trisubstituted phenyl, biphenyl, or a fused aromatic or heterocyclic rings, e.g., naphthyl or tetrahydronaphthyl or benzothiophene.

Compounds of the invention may also be 5-HT receptor modulators, e.g., 5-$HT_6$ receptor agonists, partial agonists, inverse agonists and/or antagonists.

In another embodiment compounds of the invention may also be 5-HT receptor antagonists, e.g., 5-$HT_6$ receptor antagonists.

Another aspect of the invention is a pharmaceutical composition comprising an amount of a compound according to Formula I, II, III or IV effective to treat diseases such as obesity, and obesity-related disorders, e.g., cardiovascular disease, digestive disease, respiratory disease, cancer and type II diabetes, and a pharmaceutically acceptable carrier.

Another aspect of the invention is a method for treating diseases such as obesity, and obesity-related disorders, e.g., cardiovascular disease, digestive disease, respiratory disease, cancer and type II diabetes, in a mammal such as a human comprising administering a therapeutically effective amount of a compound of Formula I, II, III or IV.

Compounds of the invention may also be 5-HT receptor modulators, e.g., 5-$HT_6$ receptor agonists, partial agonists, inverse agonists and/or antagonists.

It has surprisingly been found that compounds of the invention show affinity for the 5-$HT_6$ receptor as antagonists at low nanomolar range. Compounds of the invention and salts and/or esters thereof have 5-$HT_6$ receptor activity and are believed to be useful for treating or preventing obesity, e.g., as an appetite suppressant; and diabetes, e.g., type II diabetes; and gastrointestinal disorders such as irritable bowel syndrome (IBS); as well as treating or preventing CNS disorders such as anxiety, depression, epilepsy, panic attacks, memory disorders, sleep disorders, migraine, anorexia, bulimia, binge disorders, obsessive-compulsive disorders, psychoses, Alzheimer's disease, Parkinson's disease, Huntington's chorea and/or schizophrenia, attention deficit disorder/hyperactive disorder (ADD/HD); disorders associated with spinal trauma and/or head injury such as hydrocephalus; drug abuse withdrawal, e.g., from cocaine, nicotine, benzodiazepines; and schizophrenia.

It will be noted that the structure of some of the compounds of the invention includes asymmetric carbon atoms. It is to be understood accordingly that the isomers arising from such asymmetry (e.g., all enantiomers and diastereomers) are included within the scope of the invention, unless indicated otherwise. Such isomers can be obtained in substantially pure form by classical separation techniques and by stereochemically controlled synthesis. Furthermore, the structures and other compounds and moieties discussed in this application also include all tautomers thereof. Alkenes can include either the E- or Z-geometry, where appropriate.

"Combination therapy" (or "co-therapy") includes the administration of a 5-HT modulator of the invention and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may, but generally is not, intended to encompass the administration of two or more of these therapeutic agents as part of separate monotherapy regimens that incidentally and arbitrarily result in the combinations of the present invention. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical. "Combination therapy" also can embrace the administration of the therapeutic agents as described above in further combination with other biologically active ingredients and non-drug therapies (e.g., surgery or radiation treatment.) Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

An "anionic group," as used herein, refers to a group that is negatively charged at physiological pH. Preferred anionic groups include carboxylate, sulfate, sulfonate, sulfinate, sulfamate, tetrazolyl, phosphate, phosphonate, phosphinate, or phosphorothioate or functional equivalents thereof. "Functional equivalents" of anionic groups are intended to include bioisosteres, e.g., bioisosteres of a carboxylate group. Bioisosteres encompass both classical bioisosteric equivalents and non-classical bioisosteric equivalents. Classical and non-classical bioisosteres are known in the art (see, e.g., Silverman, R. B. *The Organic Chemistry of Drug Design and Drug Action*, Academic Press, Inc.: San Diego, Calif., 1992, pp. 19-23). A particularly preferred anionic group is a carboxylate. In one embodiment of the invention, for example, the nitrogen-containing heterocyclic group may have certain bioisosteric forms which may not necessarily include two nitrogen atoms within a single ring, or feature a ring itself; for example, 3-aminopyrrolidino

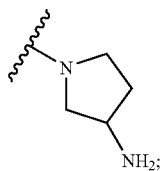

N',N'-dimethyl-3-aminopyrrolidino

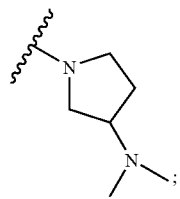

N,N',N'-trimethylethylenediamino

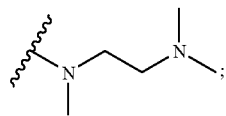

or N',N'-dimethyl-4-aminopiperidino

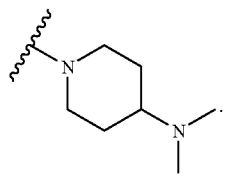

The term "heterocyclic group" is intended to include closed ring structures in which one or more of the atoms in the ring is an element other than carbon, for example, nitrogen, or oxygen or sulfur. Heterocyclic groups can be saturated or unsaturated and heterocyclic groups such as pyrrole and furan can have aromatic character. They include fused ring structures such as quinoline and isoquinoline. Other examples of heterocyclic groups include pyridine and purine. Heterocyclic groups can also be substituted at one or more constituent atoms with, for example, a halogen, a lower alkyl, a lower alkenyl, a lower alkoxy, a lower alkylthio, a lower alkylamino, a lower alkylcarboxyl, a nitro, a hydroxyl, —$CF_3$, —CN, or the like.

The compounds of the invention are valuable for treating a wide variety of clinical conditions which are characterized by serotonin excess or absence, e.g., serotonergic hypofunction or hyperfunction. Such conditions include schizophrenia and other psychotic disorders, for example, schizophrenic disorders, schizoaffective disorders, delusional disorders, brief psychotic disorders, shared psychotic disorders and psychotic disorders with delusions or hallucinations; gastrointestinal disorders like Crohn's disease, eating disorders, neuralgia, and addiction disorders; obsessive compulsive disorders, panic disorders, sexual dysfunctions caused by the central nervous system and disturbances in sleep and the absorption of food, alcoholism, pain, memory deficits, unipolar depression, dysthymia, bipolar depression, treatment-resistant depression, depression in the medically ill, panic disorder, obsessive-compulsive disorder, eating disorders, social phobia, premenstrual dysphoric disorder, mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder; anxiety disorders, such as panic disorder with or without agoraphobia, agoraphobia without history of panic disorder, specific phobias, e.g., specific animal phobias, social phobias, stress disorders including post-traumatic stress disorder and acute stress disorder, and generalized anxiety disorders; delirium, dementia, and amnestic and other cognitive or neurodegenerative disorders, such as Alzheimer's disease, senile dementia, dementia of the Alzheimer's type, vascular dementia, and other dementias, for example, due to HIV disease, head trauma, Parkinson's disease, Huntington's disease, Pick's disease, Creutzfeldt-Jakob disease, or due to multiple etiologies; Parkinson's disease and other extra-pyramidal movement disorders such as medication-induced movement disorders, for example, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor; substance-related disorders arising from the use of alcohol, amphetamines (or amphetamine-like substances) caffeine, cannabis, cocaine, hallucinogens, inhalants and aerosol propellants, nicotine, opioids, phenylglycidine derivatives, sedatives, hypnotics, and anxiolytics, which substance-related disorders include dependence and abuse, intoxication, withdrawal, intoxication delirium, withdrawal delirium, persisting dementia, psychotic disorders, mood disorders, anxiety disorders, sexual dysfunction and sleep disorders; epilepsy; Down's syndrome; demyelinating diseases such as MS and ALS and other neuropathological disorders such as peripheral neuropathy, for example, diabetic and chemotherapy-induced neuropathy, and postherpetic neuralgia, trigeminal neuralgia, segmental or intercostal neuralgia and other neuralgias; and cerebral vascular disorders due to acute or chronic cerebrovascular damage such as cerebral infarction, subarachnoid hemorrhage or cerebral edema.

Compounds of the invention may be used for the treatment of the above conditions, as well as for neuropathological disorders including Parkinson's disease and Alzheimer's disease; and for the control of disorders of the intestinal tract which are characterized by disturbances of the serotoninergic system and also by disturbances of the carbohydrate metabolism. For treating certain conditions it may be desirable to employ the compounds of the invention in conjunction with another pharmacologically active agent. The compounds of the invention may be presented together with another therapeutic agent as a combined preparation for simultaneous, separate or sequential use. Such combined preparations may be, for example, in the form of a twin pack.

The invention also provides methods for treating or preventing physiological disorders associated with serotonin excess or absence, e.g., serotonergic hypofunction or hyperfunction, which method comprises administration to a patient in need thereof of an effective amount of a compound of the invention or a composition comprising a compound of the invention.

The compounds of the invention and the other pharmacologically active agent may be administered to a patient simultaneously, sequentially or in combination. It will be appreciated that when using a combination of the invention, the compound of the invention and the other pharmacologically active agent may be in the same pharmaceutically acceptable carrier and therefore administered simultaneously. They may be in separate pharmaceutical carriers such as conventional oral dosage forms which are taken simultaneously. The term "combination" further refers to the case where the compounds are provided in separate dosage forms and are administered sequentially.

The compounds of the invention may be administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician.

In the treatment of a condition associated with a serotonin excess or absence, e.g., serotonergic hypofunction or hyperfunction, an appropriate dosage level will generally be about 0.001 to 50 mg per kg patient body weight per day, which may be administered in single or multiple doses. Preferably, the dosage level will be about 0.01 to about 25 mg/kg per day; more preferably about 0.05 to about 10 mg/kg per day. For example, in the treatment or prevention of a disorder of the central nervous system, a suitable dosage level is about 0.001 to 10 mg/kg per day, preferably about 0.005 to 5 mg/kg per day, and especially about 0.01 to 1 mg/kg per day. The compounds may be administered on a regimen of 1 to 4 times per day, preferably once or twice per day.

It will be appreciated that the amount of the compound of the invention required for use in any treatment will vary not only with the particular compounds or composition selected but also with the route of administration, the nature of the condition being treated, and the age and condition of the patient, and will ultimately be at the discretion of the attendant physician.

The compositions and combination therapies of the invention may be administered in combination with a variety of pharmaceutical excipients, including stabilizing agents, carriers and/or encapsulation formulations as described herein.

Aqueous compositions of the present invention comprise an effective amount of the peptides of the invention, dissolved or dispersed in a pharmaceutically acceptable carrier or aqueous medium.

"Pharmaceutically or pharmacologically acceptable" include molecular entities and compositions that do not produce an adverse, allergic or other untoward reaction when administered to an animal, or a human, as appropriate. "Pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For human administration, preparations should meet sterility, pyrogenicity, general safety and purity standards as required by FDA Office of Biologics standards.

The pharmaceutical compositions of this invention may be used in the form of a pharmaceutical preparation, for example, in solid, semisolid or liquid form, which contains one or more of the compound of the invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The active object compound is included in the pharmaceutical composition in an amount sufficient to produce the desired effect upon the process or condition of the disease.

For preparing solid compositions such as tablets, the principal active ingredient is mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compositions of the invention may be incorporated for administration orally or by injection include aqueous solution, suitably flavored syrups, aqueous or oil suspensions, and emulsions with acceptable oils such as cottonseed oil, sesame oil, coconut oil or peanut oil, or with a solubilizing or emulsifying agent suitable for intravenous use, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulized by use of inert gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices which deliver the formulation in an appropriate manner.

For treating clinical conditions and diseases noted above, the compound of this invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

The preparation of an aqueous composition that contains a composition of the invention or an active component or ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

Pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Solutions of active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

Pharmaceutically acceptable salts include acid addition salts and which are formed with inorganic acids such as, for example, hydrochloric, hydrobromic, boric, phosphoric, sulfuric acids or phosphoric acids, or such organic acids as acetic, oxalic, tartaric, maleic, fumaric, citric, succinic, mesylic, mandelic, succinic, benzoic, ascorbic, methanesulphonic, a-keto glutaric, a-glycerophosphoric, glucose-1-phosphoric acids and the like. Salts formed with the free carboxyl groups can also be derived from inorganic bases such as, for example, sodium, potassium, ammonium, calcium, magnesium, or ferric hydroxides, and such organic bases as isopropylamine, trimethylamine, histidine, procaine and the like. Other examples of pharmaceutically acceptable salts include quaternary derivatives of the compounds of Formulae I, II, III or IV such as the compounds quaternized by compounds $R_x$-T wherein $R_x$ is $C_{1-6}$ alkyl, phenyl-$C_{1-6}$ alkyl or $C_{5-7}$ cycloalkyl, and T is a radical corresponding to an anion of an acid. Suitable examples of $R_x$ include methyl, ethyl and n- and iso-propyl; and benzyl and phenethyl. Suitable examples of T include halide, e.g., chloride, bromide or iodide. Yet other examples of pharmaceutically acceptable salts also include internal salts such as N-oxides.

Therapeutic or pharmacological compositions of the present invention will generally comprise an effective amount of the component(s) of the combination therapy, dissolved or dispersed in a pharmaceutically acceptable medium. Pharmaceutically acceptable media or carriers include any and all solvents, dispersion media, coatings, antibacterial and antifungal agents, isotonic and absorption delaying agents and the like. The use of such media and agents for pharmaceutical active substances is well known in the art. Supplementary active ingredients can also be incorporated into the therapeutic compositions of the present invention.

The preparation of pharmaceutical or pharmacological compositions will be known to those of skill in the art in light of the present disclosure. Typically, such compositions may be prepared as injectables, either as liquid solutions or suspensions; solid forms suitable for solution in, or suspension in, liquid prior to injection; as tablets or other solids for oral administration; as time release capsules; or in any other form currently used, including cremes, lotions, mouthwashes, inhalants and the like.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze drying techniques which yield a powder of the active ingredient plus any additional desired ingredient from a previously sterile-filtered solution thereof.

The preparation of more, or highly, concentrated solutions for direct injection is also contemplated, where the use of DMSO as solvent is envisioned to result in extremely rapid penetration, delivering high concentrations of the active agents to a small area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure.

In addition to the compounds formulated for parenteral administration, such as intravenous or intramuscular injection, other pharmaceutically acceptable forms include, e.g., tablets or other solids for oral administration; liposomal formulations; time-release capsules; and any other form currently used, including creams.

The use of sterile formulations, such as saline-based washes, by surgeons, physicians or health care workers to cleanse a particular area in the operating field may also be particularly useful. Therapeutic formulations in accordance with the present invention may also be reconstituted in the form of mouthwashes, or in conjunction with antifungal reagents. Inhalant forms are also envisioned. The therapeutic formulations of the invention may also be prepared in forms suitable for topical administration, such as in cremes and lotions.

Suitable preservatives for use in such a solution include benzalkonium chloride, benzethonium chloride, chlorobutanol, thimerosal and the like. Suitable buffers include boric acid, sodium and potassium bicarbonate, sodium and potassium borates, sodium and potassium carbonate, sodium acetate, sodium biphosphate and the like, in amounts sufficient to maintain the pH at between about pH 6 and pH 8, and preferably, between about pH 7 and pH 7.5. Suitable tonicity agents are dextran 40, dextran 70, dextrose, glycerin, potassium chloride, propylene glycol, sodium chloride, and the like, such that the sodium chloride equivalent of the ophthalmic solution is in the range 0.9 plus or minus 0.2%. Suitable antioxidants and stabilizers include sodium bisulfite, sodium metabisulfite, sodium thiosulfite, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxmethylpropylcellulose, lanolin, methylcellulose, petrolatum, polyethylene glycol, polyvinyl alcohol, polyvinylpyrrolidone, carboxymethylcellulose and the like.

Upon formulation, therapeutics will be administered in a manner compatible with the dosage formulation, and in such amount as is pharmacologically effective. The formulations are easily administered in a variety of dosage forms, such as the type of injectable solutions described above, but drug release capsules and the like can also be employed.

In this context, the quantity of active ingredient and volume of composition to be administered depends on the host animal to be treated. Precise amounts of active compound required for administration depend on the judgment of the practitioner and are peculiar to each individual.

A minimal volume of a composition required to disperse the active compounds is typically utilized. Suitable regimes for administration are also variable, but would be typified by initially administering the compound and monitoring the results and then giving further controlled doses at further intervals. For example, for parenteral administration, a suitably buffered, and if necessary, isotonic aqueous solution would be prepared and used for intravenous, intramuscular, subcutaneous or even intraperitoneal administration. One dosage could be dissolved in 1 ml of isotonic NaCl solution and either added to 1000 ml of hypodermolysis fluid or injected at the proposed site of infusion, (see for example, *Remington's Pharmaceutical Sciences* 15th Edition, pages 1035-1038 and 1570-1580).

In certain embodiments, active compounds may be administered orally. This is contemplated for agents which are generally resistant, or have been rendered resistant, to proteolysis by digestive enzymes. Such compounds are contemplated to include chemically designed or modified agents; dextrorotatory peptides; and peptide and liposomal formulations in time release capsules to avoid peptidase and lipase degradation.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Additional formulations suitable for other modes of administration include suppositories. For suppositories, traditional binders and carriers may include, for example, polyalkylene glycols or triglycerides; such suppositories may be formed from mixtures containing the active ingredient in the range of 0.5% to 10%, preferably 1%-2%.

Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders.

In certain defined embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25-60%. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor.

Methods for preparing the compounds of this invention are illustrated in the following synthetic schemes and example(s). The following schemes, examples and biological data are given for the purpose of illustrating the invention, but not for limiting the scope or spirit of the invention.

SCHEME 1: GENERAL SYNTHETIC ROUTE

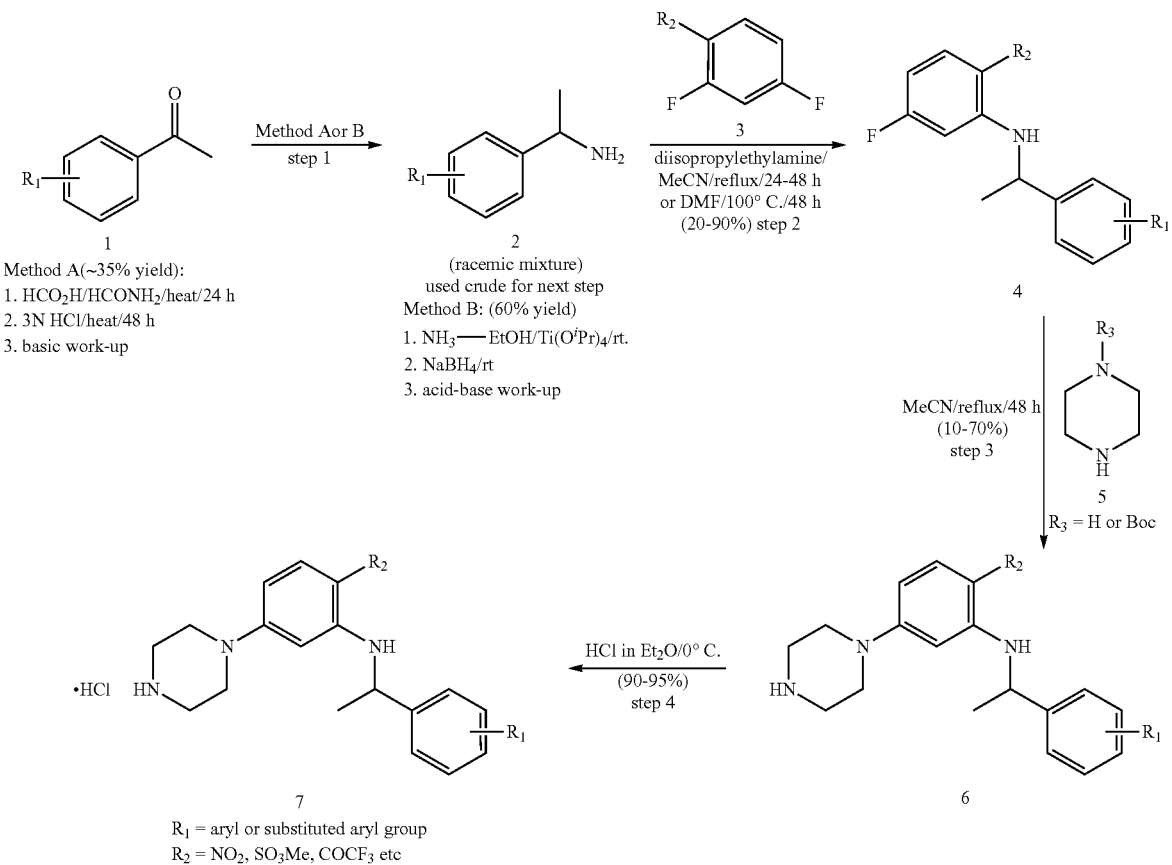

$R_1$ = aryl or substituted aryl group
$R_2 = NO_2, SO_3Me, COCF_3$ etc

EXAMPLE 1

N-(3-Chlorobenzyl)-2-nitro-5-(piperazin-1-yl)benzenamine hydrochloride

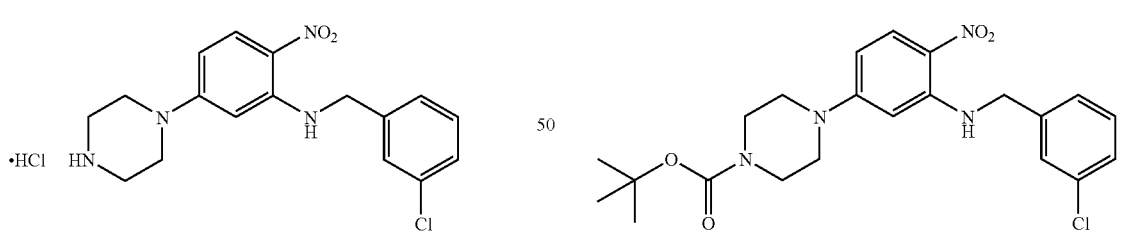

To a solution of t-butyl 4-(3-(3-chlorobenzylamino)-4-nitrophenyl)piperazine-1-carboxylate (104 mg, 0.23 mmol) in dry dichloromethane (1.0 mL) was added a saturated solution of HCl in diethyl ether (15 mL). The reaction mixture was stirred for 4 hours. The solvent was evaporated and the precipitate was recrystallized from methanol (0.3 mL), dichloromethane (0.5 mL) and diethyl ether (5 mL). The product was collected by filtration and dried in vacuo to afford the title compound (35.0 mg, 39% yield after recrystallization). $^1$H NMR (400 MHz, CD$_3$OD): δ 8.07 (d, 1H), 7.42 (s, 1H), 7.33 (m, 2H), 7.28 (m, 1H), 6.40 (d, 1H), 6.03 (s, 1H), 4.61 (s, 1H), 3.56 (m, 4H), 3.27 (m, 4H); MS (ESI) m/z: Calculated for $C_{17}H_{20}ClN_4O_2$: 347.13; Observed: 347.5 (M$^+$+1) [corresponding to the free base].

t-Butyl 4-(3-(3-chlorobenzylamino)-4-nitrophenyl)piperazine-1-carboxylate

N-(3-Chlorobenzyl)-5-fluoro-2-nitrobenzenamine (624 mg, 2.2 mmol), t-butyl piperazine-1-carboxylate (414 mg, 2.2 mmol), N,N-diisopropylethylamine (287 mg, 2.2 mmol) were stirred at 80° C. in dry acetonitrile (10 mL) for 16 h. The solvent was evaporated and the residue was dissolved in dichloromethane and washed with water. The dichloromethane was evaporated and the crude compound was purified by silica chromatography using 25% ethyl acetate in hexanes to afford the title compound (316 mg, 32% yield). $^1$H NMR (400 MHz, CDCl$_3$): δ 8.77 (s, 1H), 8.05 (d, 1H), 7.32-7.21 (m, 4H), 6.18 (d, 1H), 5.72 (s, 1H), 4.46 (d, 2H), 3.49 (m, 4H), 3.27 (m, 4H), 1.45 (s, 9H); MS (ESI) m/z: Calculated for $C_{22}H_{27}ClN_4O_4$: 446.17; Observed: 469.4 (M$^+$+Na).

N-(3-Chlorobenzyl)-5-fluoro-2-nitrobenzenamine

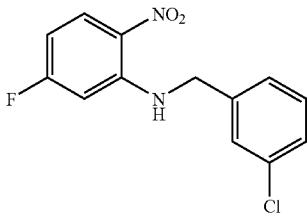

2,4-Difluoronitrobenzene (2.9 g, 18.1 mmol), 3-chlorobenzylamine (2.6 g, 18.1 mmol) and N,N-diisopropylethylamine (2.4 g, 18.1 mmol) were stirred in acetonitrile (25 mL) at room temperature for 2 hours. The solvent was evaporated and the crude mixture was dissolved in dichloromethane and washed with water. The dichloromethane was evaporated in vacuo to collect the title compound (4.8 g, 95% yield). $^1$H NMR (400 MHz, CDCl$_3$): δ 8.55 (s, 1H), 8.25 (dd, 1H), 7.32-7.21 (m, 4H), 6.41 (m, 2H), 4.50 (d, 2H).

EXAMPLE 2

N-(3-Chlorobenzyl)-4-nitro-3-(piperazin-1-yl)benzenamine hydrochloride

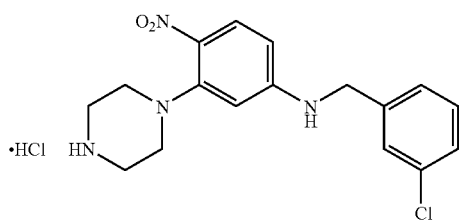

To a solution of N-(3-chlorobenzyl)-4-nitro-3-(piperazin-1-yl)benzenamine (77 mg, 0.17 mmol) in dry dichloromethane (1.0 mL) was added a saturated solution of HCl in diethyl ether (15 mL). The reaction mixture was stirred for 4 hours. The solvent was evaporated and the precipitate was recrystallized from methanol (0.3 mL), dichloromethane (0.5 mL) and diethyl ether (5 mL). The product was collected by filtration and dried in vacuo to afford the title compound (54 mg, 82% yield after recrystallization). $^1$H NMR (400 MHz, CD$_3$OD): δ 8.01 (d, 1H), 7.37-7.27 (m, 4H), 6.39 (d, 1H), 6.25 (s, 1H), 4.45 (s, 2H), 3.36 (m, 4H), 3.23 (m, 4H); MS (ESI) m/z: Calculated for C$_{17}$H$_{20}$ClN$_4$O$_2$: 347.13; Observed: 347.4 (M$^+$+1) [corresponding to the free base].

t-Butyl 4-(5-(3-chlorobenzylamino)-2-nitrophenyl)piperazine-1-carboxylate

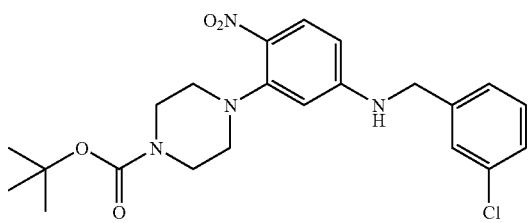

t-Butyl 4-(5-fluoro-2-nitrophenyl)piperazine-1-carboxylate (431 mg, 1.3 mmol), 3-chlorobenzylamine (187 mg, 1.3 mmol), N,N-diisopropylethylamine (342 mg, 1.3 mmol) were stirred at 80° C. in dry acetonitrile (25 mL) for 72 h. The solvent was evaporated and the residue was dissolved in dichloromethane and washed with water. The dichloromethane was evaporated and the crude compound was purified by silica chromatography using 25% ethyl acetate in hexanes to afford the title compound (277 mg, 48% yield). $^1$H NMR (400 MHz, CD$_3$OD): δ 7.96 (d, 1H), 7.37-7.26 (m, 4H), 6.29 (d, 1H), 6.18 (s, 1H), 4.42 (s, 2H), 3.55 (m, 4H), 2.92 (m, 4H), 1.47 (s, 9H); MS (ESI) m/z: Calculated for C$_{22}$H$_{27}$ClN$_4$O$_4$: 446.17; Observed: 469.2 (M$^+$+Na).

t-Butyl 4-(5-fluoro-2-nitrophenyl)piperazine-1-carboxylate

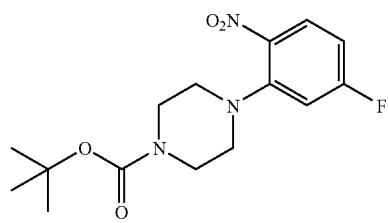

2,4-Difluoronitrobenzene (10.0 g, 62.9 mmol), t-butyl piperazine-1-carboxylate (11.7 g, 62.9 mmol) and N,N-diisopropylethylamine (8.10 g, 62.9 mmol) were stirred at room temperature in dry acetonitrile (100 mL) for 16 h. The solvent was removed by rotary evaporation and the residue was dissolved in dichloromethane and washed with water. The dichloromethane was removed by rotary evaporation to collect the title compound (19.0 g, 93%). $^1$H NMR (400 MHz, CDCl$_3$): δ 7.91 (dd, 1H), 6.75 (m, 2H), 3.60 (m, 4H), 3.03 (m, 4H), 1.48 (s, 9H); MS (ESI) m/z: Calculated for C$_{15}$H$_{20}$FN$_3$O$_4$: 325.14; Observed: 348.1 (M$^+$+Na).

EXAMPLE 3

1-(2-(1-(3,5-Dimethoxyphenyl)ethylamino)-4-(piperazin-1-yl)phenyl)-2,2,2-trifluoroethanone hydrochloride

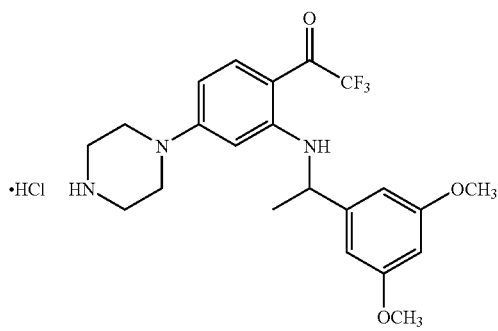

To a solution of t-butyl 4-(3-(1-(3,5-dimethoxyphenyl)ethylamino)-4-(2,2,2-trifluoroacetyl)phenyl)piperazine-1-carboxylate (231 mg, 0.43 mmol) in dichloromethane (2.0 mL) and methanol (0.5 mL) was added a saturated solution of HCl in diethyl ether (20 mL). The reaction mixture was stirred for 3 hours. The solvent was removed by rotary evaporation to afford the title compound (198 mg, 97% yield). $^1$H NMR (400

MHz, CD₃OD): δ 7.62 (m, 1H), 6.52 (s, 2H), 6.36 (m, 2H), 5.49 (s, 1H), 4.66 (m, 1H), 3.57 (m, 2H), 3.50 (m, 2H), 3.21 (m, 4H), 1.58 (d, 3H); MS (ESI) m/z: Calculated for $C_{22}H_{27}F_3N_3O_3$: 438.2; Observed: 439.5 (M⁺+1) [corresponding to the free base].

t-Butyl 4-(3-(1-(3,5-dimethoxyphenyl)ethylamino)-4-(2,2,2-trifluoroacetyl)phenyl)piperazine-1-carboxylate

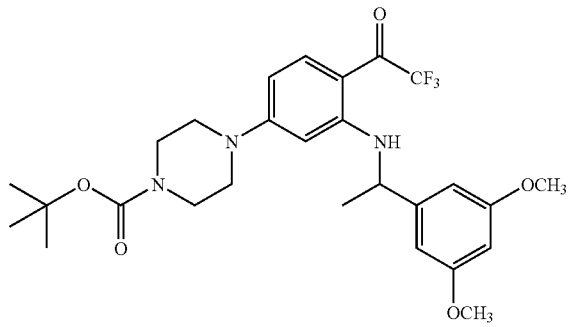

1-(2-(1-(3,5-Dimethoxyphenyl)ethylamino)-4-fluorophenyl)-2,2,2-trifluoroethanone (600 mg, 1.62 mmol), t-butyl piperazine-1-carboxylate (300 mg, 1.62 mmol), N,N-diisopropylethylamine (418 mg, 3.24 mmol) were stirred at 80° C. in dry acetonitrile (25 mL) for 21 h. The solvent was evaporated and the residue was dissolved in dichloromethane and washed with water. The dichloromethane was evaporated and the crude compound was purified by silica chromatography using 20% ethyl acetate in hexanes to afford the title compound (231 mg, 27% yield). ¹H NMR (400 MHz, CDCl₃): δ 9.30 (d, 1H), 7.59 (d, 1H), 6.48 (s, 2H), 6.33 (s, 1H), 6.13 (d, 1H), 5.68 (s, 1H), 4.44 (m, 1H), 3.43 (m, 4H), 3.25 (m, 2H), 3.20 (m, 2H), 1.59 (d, 3H), 1.46 (s, 9H); MS (ESI) m/z: Calculated for $C_{27}H_{34}F_3N_3O_5$: 537.25; Observed: 560.3 (M⁺+Na).

1-(2-(1-(3,5-Dimethoxyphenyl)ethylamino)-4-fluorophenyl)-2,2,2-trifluoroethanone

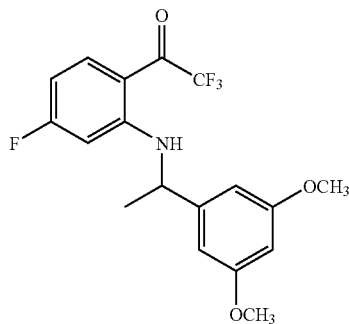

2,2,2-Trifluoro-1-(2,4-difluorophenyl)ethanone (1.0 g, 4.8 mmol), 1-(3,5-dimethoxyphenyl)ethanamine (0.95 g, 5.2 mmol) and N,N-diisopropylethylamine (1.2 g, 9.6 mmol) were stirred at 60° C. in dry acetonitrile (50 mL) for 16 h. The solvent was evaporated and the residue was dissolved in dichloromethane and washed with water. The dichloromethane was evaporated and purified by silica chromatography in 20% ethyl acetate in hexanes to collect the title compound (600 mg, 34% yield). ¹H NMR (400 MHz, CDCl₃): δ 9.27 (s, 1H), 7.79 (t, 1H), 6.44 (s, 2H), 6.35 (m, 2H), 6.23 (d, 1H), 4.48 (m, 1H), 3.77 (s, 6H), 1.61 (d, 3H).

EXAMPLE 4

N-(1-(3-Chlorophenyl)ethyl)-2-nitro-5-(piperazin-1-yl)benzenamine hydrochloride

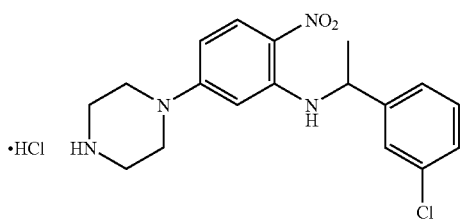

To a solution of t-butyl 4-(3-(1-(3-chlorophenyl)ethylamino)-4-nitrophenyl)piperazine-1-carboxylate (97 mg, 0.21 mmol) in dry dichloromethane (2.0 mL) was added a saturated solution of HCl in diethyl ether (15 mL). The reaction mixture was stirred for 4 hours. The product was collected by filtration and dried in vacuo to afford the title compound (58.0 mg, 70% yield). ¹H NMR (400 MHz, CD₃OD): δ 8.06 (d, 1H), 7.43 (s, 1H), 7.33 (m, 2H), 7.26 (m, 1H), 6.38 (d, 1H), 5.88 (s, 1H), 4.80 (m, 1H), 3.54-3.43 (m, 4H), 3.22 (m, 4H), 1.62 (d, 3H); MS (ESI) m/z: Calculated for $C_{18}H_{22}ClN_4O_2$: 360.14; Observed: 361.5 (M⁺+1) [corresponding to the free base].

t-Butyl 4-(3-(1-(3-chlorophenyl)ethylamino)-4-nitrophenyl)piperazine-1-carboxylate

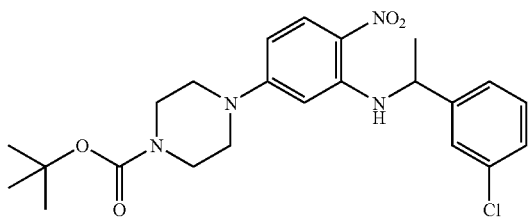

N-(1-(3-Chlorophenyl)ethyl)-5-fluoro-2-nitrobenzenamine (522 mg, 1.8 mmol), t-butyl piperazine-1-carboxylate (329 mg, 1.8 mmol), N,N-diisopropylethylamine (457 mg, 3.5 mmol) were stirred at 90° C. in dry acetonitrile (50 mL) for 24 h. The solvent was evaporated and the residue was dissolved in dichloromethane and washed with water. The dichloromethane was evaporated and the crude compound was purified by silica chromatography using 25% ethyl acetate in hexanes to afford the title compound (95 mg, 12% yield). ¹H NMR (400 MHz, CDCl₃): δ 8.70 (s, 1H), 8.06 (d, 1H), 7.33-7.21 (m, 4H), 6.15 (d, 1H), 5.58 (s, 1H), 4.53 (m, 1H), 3.43 (m, 4H), 3.21 (m, 2H), 3.13 (m, 2H), 1.63 (d, 3H), 1.46 (s, 9H); MS (ESI) m/z: Calculated for $C_{23}H_{29}ClN_4O_4$: 460.19; Observed: 483.3 (M⁺+Na).

N-(1-(3-Chlorophenyl)ethyl)-5-fluoro-2-nitrobenzenamine

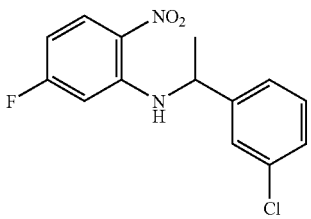

1-(3-Chlorophenyl)ethanamine (553 mg, 3.55 mmol), 2,4-difluoronitrobenzene (565 mg, 3.55 mmol) and N,N-diisopropylethylamine (918 mg, 7.10 mmol) were stirred at room temperature in dry acetonitrile (20 mL) for 6 h. The solvent was evaporated and the residue was dissolved in dichloromethane and washed with water. The dichloromethane was evaporated to collect the title compound (600 mg, 57% yield). $^1$H NMR (400 MHz, CDCl$_3$): δ 8.49 (s, 1H), 8.23 (m, 1H), 7.04 (m, 4H), 6.36 (t, 1H), 6.22 (d, 1H), 4.56 (m, 1H), 1.64 (d, 3H); MS (ESI) m/z: Calculated for C$_{14}$H$_{13}$ClFN$_2$O$_2$: 295.06; Observed: 295.0 (M$^+$+1).

1-(3-Chlorophenyl)ethanamine

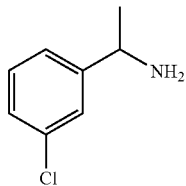

1-(3-Chlorophenyl)ethanone (11.9 g, 77.5 mmol) and formic acid (3.72 g, 77.5 mmol) were heated in formamide (10 mL) at 170-180° C. for 20 h. The mixture was cooled to room temperature, diluted with water and extracted with benzene. After removal of benzene by rotary evaporation the crude mixture was heated under reflux conditions in 3M HCl for 30 h. After cooling, the reaction was added to ether and extracted. The aqueous layer was basified with NaOH to pH 9 and extracted with dichloromethane. The dichloromethane was evaporated to collect the title compound (3.93 g, 33%). $^1$H NMR (400 MHz, CDCl$_3$): δ 7.34 (s, 1H), 7.21 (m, 3H), 4.07 (m, 1H), 1.35 (d, 3H); MS (ESI) m/z: Calculated for C$_8$H$_{11}$ClN: 156.06; Observed: 156.0 (M$^+$+1).

EXAMPLE 5

N-(1-(3,5-Dimethoxyphenyl)ethyl)-2-nitro-5-(piperazin-1-yl)benzenamine hydrochloride

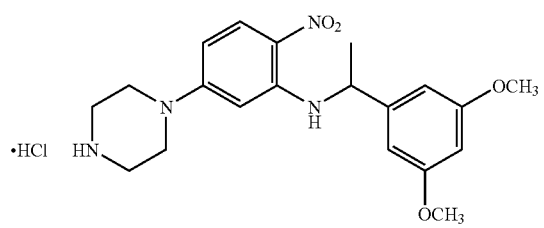

To a solution of t-butyl 4-(3-(1-(3,5-dimethoxyphenyl)ethylamino)-4-nitrophenyl)piperazine-1-carboxylate (327 mg, 0.67 mmol) in dry dichloromethane (2.0 mL) was added a saturated solution of HCl in diethyl ether (15 mL). The reaction mixture was stirred for 4 hours. The product was collected by filtration and dried in vacuo to afford the title compound (216 mg, 76% yield). $^1$H NMR (400 MHz, CD$_3$OD): δ 8.03 (d, 1H), 6.55 (s, 2H), 6.36 (m, 2H), 5.95 (s, 1H), 4.67 (m, 1H), 3.73 (s, 6H), 3.49 (m, 4H), 3.29 (m, 4H), 1.60 (d, 3H); MS (ESI) m/z: Calculated for C$_{20}$H$_{27}$N$_4$O$_4$: 387.2; Observed: 387.3 (M$^+$+1) [corresponding to the free base].

t-Butyl 4-(3-(1-(3,5-dimethoxyphenyl)ethylamino)-4-nitrophenyl)piperazine-1-carboxylate

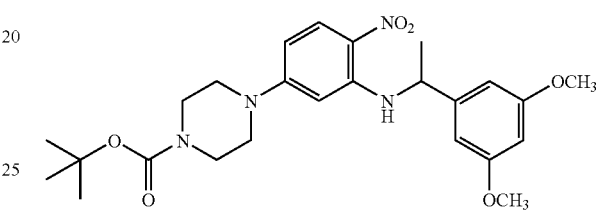

5-Fluoro-N-(1-(3,5-dimethoxyphenyl)ethyl)-2-nitrobenzenamine (762 mg, 2.4 mmol), t-butyl piperazine-1-carboxylate (443 mg, 2.4 mmol), N,N-diisopropylethylamine (614 mg, 4.8 mmol) were stirred at 80° C. in dry acetonitrile (50 mL) for 48 h. The solvent was evaporated and the residue was dissolved in dichloromethane and washed with water. The dichloromethane was evaporated and the crude compound was purified by silica chromatography using 25% ethyl acetate in hexanes to afford the title compound (469 mg, 41% yield). $^1$H NMR (400 MHz, CDCl$_3$): δ 8.68 (s, 1H), 8.05 (d, 1H), 6.49 (s, 2H), 6.33 (s, 1H), 6.14 (d, 1H), 5.70 (s, 1H), 4.47 (m, 1H), 3.76 (s, 6H), 3.43 (m, 4H), 3.23 (m, 2H), 3.15 (m, 2H), 1.62 (d, 3H), 1.46 (s, 9H); MS (ESI) m/z: Calculated for C$_{25}$H$_{34}$N$_4$O$_6$: 486.25; Observed: 509.3 (M$^+$+Na).

5-Fluoro-N-(1-(3,5-dimethoxyphenyl)ethyl)-2-nitrobenzenamine

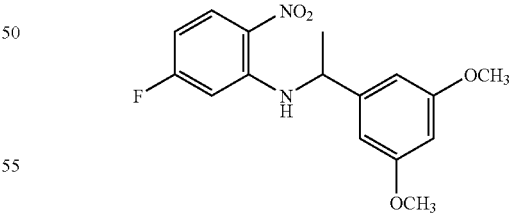

1-(3,5-Dimethoxyphenyl)ethanamine (670 mg, 4.2 mmol), 2,4-difluoronitrobenzene (764 mg, 4.2 mmol) and N,N-diisopropylethylamine (1.08 mg, 8.4 mmol) were stirred at room temperature in dry acetonitrile (50 mL) for 6 h. The solvent was evaporated and the residue was dissolved in dichloromethane and washed with water. The dichloromethane was evaporated to collect the title compound (820 mg, 61% yield). $^1$H NMR (400 MHz, CDCl$_3$): δ 8.49 (s, 1H), 8.19 (m, 1H), 6.45 (s, 2H), 6.30 (m, 3H), 4.48 (m, 1H), 3.76

(s, 6H), 1.62 (d, 3H); MS (ESI) m/z: Calculated for $C_{16}H_{17}FN_2O_4$: 320.12; Observed: 343.2 (M$^+$+1).

EXAMPLE 6

1-(2-(1-Phenylethylamino)-4-(piperazin-1-yl)phenyl)-2,2,2-trifluoroethanone hydrochloride

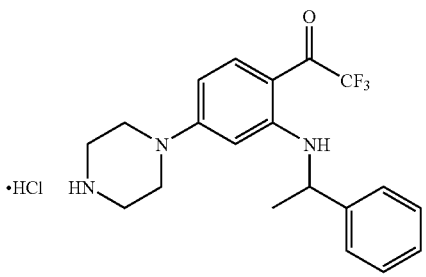

To a solution of t-butyl 4-(3-(1-phenylethylamino)-4-(2,2,2-trifluoroacetyl)phenyl)piperazine-1-carboxylate (50 mg, 0.1 mmol) in dry dichloromethane (1.0 mL) was added a saturated solution of HCl in diethyl ether (20 mL). The reaction mixture was stirred for 2 hours. The solvent was removed by rotary evaporation to afford the title compound (31 mg, 72% yield). $^1$H NMR (400 MHz, CD$_3$OD): δ 7.63 (d, 1H), 7.36 (m, 5H), 6.36 (d, 1H), 5.86 (s, 1H), 4.75 (m, 1H), 3.52 (m, 2H), 3.45 (m, 2H), 3.17 (m, 4H), 1.60 (d, 3H); MS (ESI) m/z: Calculated for $C_{20}H_{23}F_3N_3O$: 378.18; Observed: 378.5 (M$^+$+1) [corresponding to the free base].

t-Butyl 4-(3-(1-phenylethylamino)-4-(2,2,2-trifluoroacetyl)phenyl)piperazine-1-carboxylate

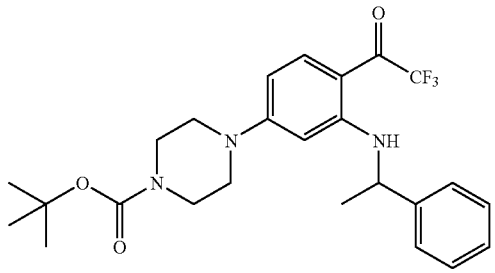

1-(2-(1-Phenylethylamino)-4-fluorophenyl)-2,2,2-trifluoroethanone (150 mg, 0.48 mmol), t-butyl piperazine-1-carboxylate (98.7 mg, 0.53 mmol), N,N-diisopropylethylamine (124 mg, 0.96 mmol) were stirred at 80° C. in dry acetonitrile (25 mL) for 21 h. The solvent was evaporated and the residue was dissolved in dichloromethane and washed with water. The dichloromethane was evaporated and the crude compound was purified by silica chromatography using 25% ethyl acetate in hexanes to afford the title compound (70 mg, 30% yield). $^1$H NMR (400 MHz, CDCl$_3$): δ 9.36 (d, 1H), 7.60 (d, 1H), 7.32 (m, 4H), 7.24 (m, 1H), 6.13 (d, 1H), 5.61 (s, 1H), 4.55 (m, 1H), 3.41 (m, 4H), 3.25 (m, 2H), 3.14 (m, 2H), 1.61 (d, 3H), 1.46 (s, 9H); MS (ESI) m/z: Calculated for $C_{25}H_{30}F_3N_3O_3$: 477.22; Observed: 500.3 (M$^+$+Na).

1-(2-(1-Phenylethylamino)-4-fluorophenyl)-2,2,2-trifluoroethanone

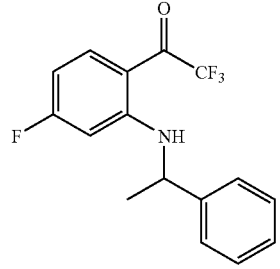

2,2,2-Trifluoro-1-(2,4-difluorophenyl)ethanone (1.59 g, 7.57 mmol), 1-phenylethanamine (0.92 g, 7.57 mmol) and N,N-diisopropylethylamine (1.95 g, 15.1 mmol) were stirred at room temperature in dry acetonitrile (50 mL) for 20 h. The solvent was evaporated and the residue was dissolved in dichloromethane and washed with water. The dichloromethane was evaporated and purified by silica chromatography in 20% ethyl acetate in hexanes to collect the title compound (0.28 mg, 12% yield). $^1$H NMR (400 MHz, CDCl$_3$): δ 9.32 (s, 1H), 7.80 (t, 1H), 7.31 (m, 5H), 6.33 (t, 1H), 6.22 (d, 1H), 4.58 (m, 1H), 1.62 (d, 3H).

EXAMPLE 7

1-(2-(1-(3,5-Dimethoxyphenyl)ethylamino)-4-(piperazin-1-yl)phenyl)-2,2,2-trifluoroethanone hydrochloride

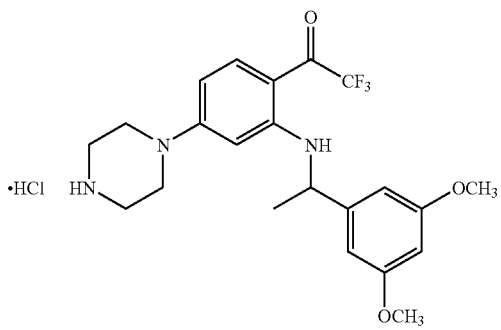

To a solution of t-butyl 4-(3-(1-(3,5-dimethoxyphenyl)ethylamino)-4-(2,2,2-trifluoroacetyl)phenyl)piperazine-1-carboxylate (231 mg, 0.43 mmol) in dichloromethane (2.0 mL) and methanol (0.5 mL) was added a saturated solution of HCl in diethyl ether (20 mL). The reaction mixture was stirred for 3 hours. The solvent was removed by rotary evaporation to afford the title compound (198 mg, 97% yield). $^1$H NMR (400 MHz, CD$_3$OD): δ 7.62 (m, 1H), 6.52 (s, 2H), 6.36 (m, 2H), 5.49 (s, 1H), 4.66 (m, 1H), 3.57 (m, 2H), 3.50 (m, 2H), 3.21

(m, 4H), 1.58 (d, 3H); MS (ESI) m/z: Calculated for $C_{22}H_{27}F_3N_3O_3$: 438.2; Observed: 439.5 (M$^+$+1) [corresponding to the free base].

t-Butyl 4-(3-(1-(3,5-dimethoxyphenyl)ethylamino)-4-(2,2,2-trifluoroacetyl)phenyl)piperazine-1-carboxylate

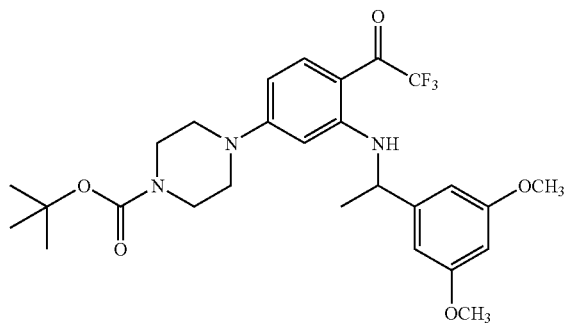

1-(2-(1-(3,5-Dimethoxyphenyl)ethylamino)-4-fluorophenyl)-2,2,2-trifluoroethanone (600 mg, 1.62 mmol), t-butyl piperazine-1-carboxylate (300 mg, 1.62 mmol), N,N-diisopropylethylamine (418 mg, 3.24 mmol) were stirred at 80° C. in dry acetonitrile (25 mL) for 21 h. The solvent was evaporated and the residue was dissolved in dichloromethane and washed with water. The dichloromethane was evaporated and the crude compound was purified by silica chromatography using 20% ethyl acetate in hexanes to afford the title compound (231 mg, 27% yield). $^1$H NMR (400 MHz, CDCl$_3$): δ 9.30 (d, 1H), 7.59 (d, 1H), 6.48 (s, 2H), 6.33 (s, 1H), 6.13 (d, 1H), 5.68 (s, 1H), 4.44 (m, 1H), 3.43 (m, 4H), 3.25 (m, 2H), 3.20 (m, 2H), 1.59 (d, 3H), 1.46 (s, 9H); MS (ESI) m/z: Calculated for $C_{27}H_{34}F_3N_3O_5$: 537.25; Observed: 560.3 (M$^+$+Na).

1-(2-(1-(3,5-Dimethoxyphenyl)ethylamino)-4-fluorophenyl)-2,2,2-trifluoroethanone

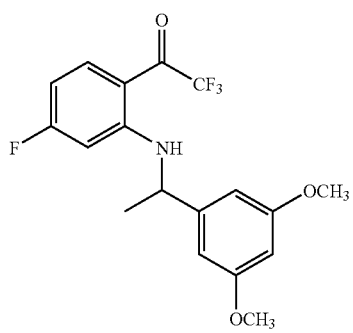

2,2,2-Trifluoro-1-(2,4-difluorophenyl)ethanone (1.0 g, 4.8 mmol), 1-(3,5-dimethoxyphenyl)ethanamine (0.95 g, 5.2 mmol) and N,N-diisopropylethylamine (1.2 g, 9.6 mmol) were stirred at 60° C. in dry acetonitrile (50 mL) for 16 h. The solvent was evaporated and the residue was dissolved in dichloromethane and washed with water. The dichloromethane was evaporated and purified by silica chromatography in 20% ethyl acetate in hexanes to collect the title compound (600 mg, 34% yield). $^1$H NMR (400 MHz, CDCl$_3$): δ 9.27 (s, 1H), 7.79 (t, 1H), 6.44 (s, 2H), 6.35 (m, 2H), 6.23 (d, 1H), 4.48 (m, 1H), 3.77 (s, 6H), 1.61 (d, 3H).

EXAMPLE 8

1-(2-(1-(3,5-Dichlorophenyl)ethylamino)-4-(piperazin-1-yl)phenyl)-2,2,2-trifluoroethanone hydrochloride

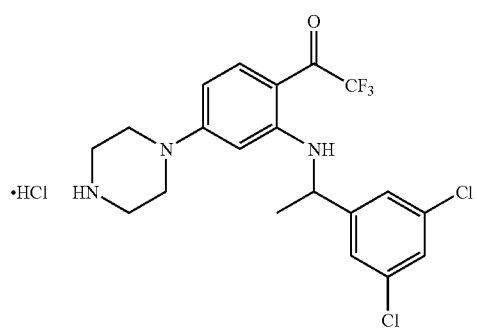

To a solution of t-butyl 4-(3-(1-(3,5-dichlorophenyl)ethylamino)-4-(2,2,2-trifluoroacetyl)phenyl)piperazine-1-carboxylate (50.1 mg, 0.09 mmol) in dichloromethane (2.0 mL) was added a saturated solution of HCl in diethyl ether (15 mL). The reaction mixture was stirred for 2 hours. The solvent was removed by rotary evaporation to afford the title compound (42.0 mg, 95% yield). $^1$H NMR (400 MHz, CD$_3$OD): δ 7.67 (d, 1H), 7.37 (s, 2H), 7.35 (s, 1H), 6.41 (d, 1H), 5.84 (s, 1H), 4.79 (m, 1H), 3.57 (m, 4H), 3.25 (m, 4H), 1.61 (d, 3H); MS (ESI) m/z: Calculated for $C_{20}H_{21}Cl_2F_3N_3O$: 446.1; Observed: 446.5 (M$^+$+1) [corresponding to the free base].

t-Butyl 4-(3-(1-(3,5-dichlorophenyl)ethylamino)-4-(2,2,2-trifluoroacetyl)phenyl)piperazine-1-carboxylate

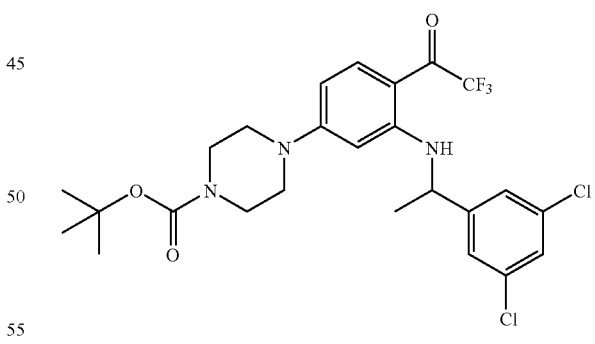

1-(2-(1-(3,5-Dichlorophenyl)ethylamino)-4-fluorophenyl)-2,2,2-trifluoroethanone (600 mg, 1.62 mmol), t-butyl piperazine-1-carboxylate (110 mg, 0.29 mmol), N,N-diisopropylethylamine (74.6 mg, 0.58 mmol) were stirred at 60° C. in dry acetonitrile (20 mL) for 3 days. The solvent was evaporated and the residue was dissolved in dichloromethane and washed with water. The dichloromethane was evaporated and the crude compound was purified by silica chromatography using 20% ethyl acetate in hexanes to afford the title compound (77.0 mg, 49% yield). $^1$H NMR (400 MHz, CDCl$_3$): δ 9.31 (d, 1H), 7.63 (d, 1H), 7.25 (s, 1H), 7.22 (s, 2H), 6.18 (d, 1H), 5.53 (s, 1H), 4.48 (m, 1H), 3.48 (m, 4H), 3.25 (m, 4H), 1.60 (d, 3H), 1.47 (s, 9H); MS (ESI) m/z: Calculated for $C_{25}H_{28}Cl_2F_3N_3O_3$: 545.15; Observed: 568.4 (M$^+$+Na).

1-(2-(1-(3,5-Dichlorophenyl)ethylamino)-4-fluorophenyl)-2,2,2-trifluoroethanone

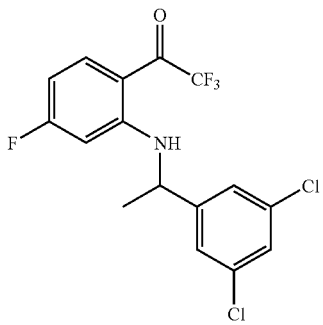

2,2,2-Trifluoro-1-(2,4-difluorophenyl)ethanone (0.66 g, 3.13 mmol), 1-(3,5-dichlorophenyl)ethanamine (0.59 g, 3.13 mmol) and N,N-diisopropylethylamine (0.81 g, 6.3 mmol) were stirred at 45° C. in dry acetonitrile (25 mL) for 16 h. The solvent was evaporated and the residue was dissolved in dichloromethane and washed with water. The dichloromethane was evaporated and purified by silica chromatography in 20% ethyl acetate in hexanes to collect the title compound (0.11 mg, 9% yield). $^1$H NMR (400 MHz, CDCl$_3$): δ 9.23 (s, 1H), 7.87 (t, 1H), 7.28 (s, 1H), 7.19 (s, 2H), 6.41 (t, 1H), 6.11 (d, 1H), 4.51 (m, 1H), 1.62 (d, 3H).

EXAMPLE 9

N-(1-(5-Chloro-2-methoxyphenyl)ethyl)-2-(methylsulfonyl)-5-(piperazin-1-yl)benzenamine hydrochloride

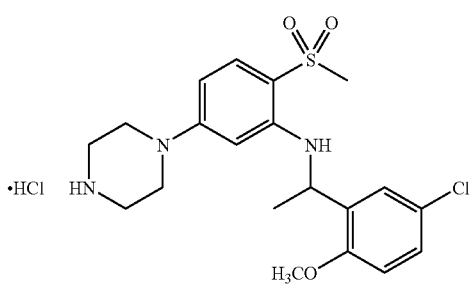

To a solution of N-(1-(5-chloro-2-methoxyphenyl)ethyl)-2-(methylsulfonyl)-5-(piperazin-1-yl)benzenamine (15.0 mg, 0.04 mmol) in dichloromethane (1 mL) was added 10 mL of 1 M HCl in ether. The solution was allowed to stir for 1 h after which a precipitate formed. The solvent was removed by rotary evaporation to collect the title compound (16.0 mg, 0.04 mmol) in 100% yield. $^1$H NMR (400 MHz, CD$_3$OD): δ 8.10 (s, 1H), 7.55 (s, 1H), 7.30 (d, 1H), 7.21 (q, 1H), 7.02 (d, 1H), 6.39 (d, 1H), 4.66 (m, 1H), 3.92 (s, 3H), 3.40 (m, 4H), 3.26 (m, 4H), 1.53 (d, 3H); MS (ESI) m/z: Calculated for $C_{20}H_{27}ClN_3O_3S$: 424.15; Observed: (M$^+$+1) [corresponding to the free base].

N-(1-(5-Chloro-2-methoxyphenyl)ethyl)-2-(methylsulfonyl)-5-(piperazin-1-yl)benzenamine

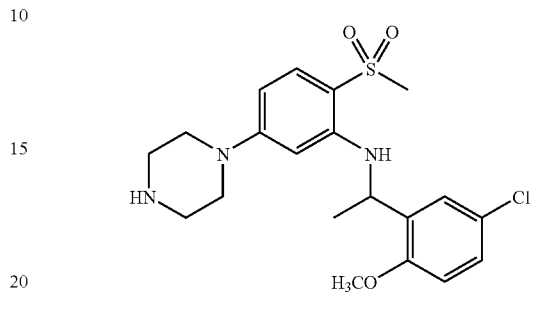

N-(1-(5-Chloro-2-methoxyphenyl)ethyl)-5-fluoro-2-(methylsulfonyl)benzenamine (50.0 mg, 0.14 mmol), piperazine (36.0 mg, 0.42 mmol), N,N-diisopropylethylamine (36.0 mg, 0.28 mmol) were stirred at 80° C. in dry acetonitrile (5 mL) for 48 h. The solvent was evaporated and the residue was dissolved in dichloromethane and washed with water. The dichloromethane was evaporated and the crude compound was purified by silica chromatography using 15% methanol in dichloromethane to afford the title compound (15.0 mg, 25% yield). $^1$H NMR (400 MHz, CDCl$_3$): δ 7.55 (d, 1H), 7.16 (d, 1H), 6.81 (d, 1H), 6.58 (d, 1H), 6.22 (d, 1H), 5.83 (s, 1H), 5.30 (s, 1H), 4.85 (m, 1H), 3.87 (s, 3H), 3.11 (m, 4H), 2.91 (m, 4H), 1.51 (d, 3H); MS (ESI) m/z: Calculated for $C_{20}H_{27}ClN_3O_3S$: 424.15; Observed: 424.4 (M$^+$).

N-(1-(5-Chloro-2-methoxyphenyl)ethyl)-5-fluoro-2-(methylsulfonyl)benzenamine

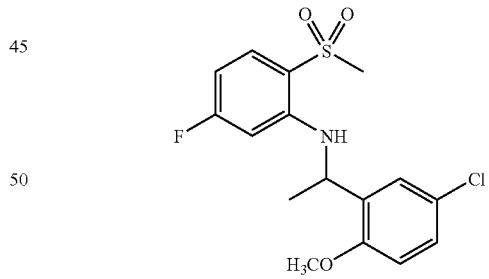

2,4-Difluoro-1-(methylsulfonyl)benzene (0.55 g, 2.9 mmol), 1-(5-chloro-2-methoxyphenyl)ethanamine (0.57 g, 2.9 mmol) and N,N-diisopropylethylamine (0.77 g, 5.9 mmol) were stirred at 65° C. in dry acetonitrile (20 mL) for 24 h. The solvent was evaporated and the residue was dissolved in dichloromethane and washed with water. The dichloromethane was evaporated and purified by silica chromatography in 20% ethyl acetate in hexanes to collect the title compound (0.36 mg, 35% yield). $^1$H NMR (400 MHz, CDCl$_3$): δ 7.74 (q, 1H), 7.18 (m, 2H), 6.84 (d, 1H), 6.79 (d, 1H), 6.42 (t, 1H), 6.17 (d, 1H), 4.78 (m, 1H), 3.91 (s, 3H), 3.08 (s, 3H), 1.52 (d, 3H).

1-(5-Chloro-2-methoxyphenyl)ethanamine

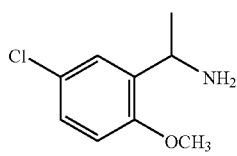

1-(5-Chloro-2-methoxyphenyl)ethanone (6.7 g, 36.3 mmol) and formic acid (1.74 g, 27.7 mmol) were heated in formamide (10 mL) at 170° C. for 20 h. The mixture was cooled to room temperature, diluted with water and extracted with benzene. After removal of benzene by rotary evaporation the crude mixture was heated under reflux conditions in 3M HCl for 30 h. After cooling, the reaction was added to ether and extracted. The aqueous layer was basified with NaOH to pH 9 and extracted with dichloromethane. The dichloromethane was evaporated to collect the title compound (2.7 g, 40%). $^1$H NMR (400 MHz, CDCl$_3$): δ 7.39 (d, 1H), 7.26 (q, 1H), 6.81 (d, 1H), 4.62 (m, 1H), 3.84 (s, 3H), 1.69 (d, 3H).

EXAMPLE 10

N-(2-Methyl-1-phenylpropyl)-2-nitro-5-(piperazin-1-yl)benzenamine hydrochloride

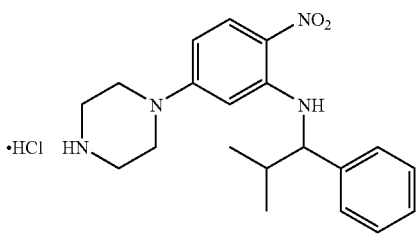

A saturated solution of HCl gas in anhydrous diethyl ether was added portion wise to a solution of tert-butyl 4-(3-(2-methyl-1-phenylpropylamino)-4-nitrophenyl)piperazine-1-carboxylate (145 mg, 0.32 mmol) in anhydrous dichloromethane (0.5 mL). The resulting mixture was allowed to stand at room temperature for 30 min, and conversion was monitored by LCMS. The solvent was concentrated down in vacuo and co-evaporated with diethyl ether to yield 60 mg (53%) of the title compound: $^1$H NMR (400 MHz, CD$_3$OD): δ 8.04 (dd, 1H), 7.36-7.32 (m, 4H), 7.28-7.24 (m, 1H), 6.34 (br d, 1H), 5.89 (br s, 1H), 4.45 (br d, 1H), 3.50-3.20 (m, 8H), 2.18 (m, 1H), 1.09 (d, 3H), 0.98 (d, 3H). MS (ESI) m/z: Calculated: 354.26; Observed: 355.6 (M$^+$+1) [corresponding to the free base].

t-Butyl 4-(3-(2-methyl-1-phenylpropylamino)-4-nitrophenyl)piperazine-1-carboxylate

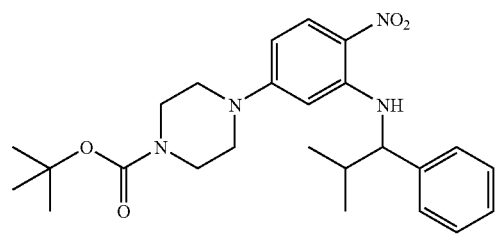

A solution of 5-fluoro-N-(2-methyl-1-phenylpropyl)-2-nitrobenzenamine (1.79 g, 6.2 mmol), N-Boc-piperazine (1.16 g, 6.2 mmol) and N,N-diisopropylethylamine (2.2 mL, 12.4 mmol) in acetonitrile was stirred at reflux for 24 h. The reaction mixture was cooled down and concentrated under reduced pressure. The residue was taken up in dichloromethane, washed with water, dried and concentrated in vacuo to yield 2.45 g of the crude aniline. The crude product was purified by PTLC (15% ethyl acetate in hexanes) to yield 1.75 g (62%) of tert-butyl 4-(3-(2-methyl-1-phenylpropylamino)-4-nitrophenyl)piperazine-1-carboxylate: $^1$H NMR (400 MHz, CD$_3$OD): δ 9.01 (br d, 1H), 7.96 (dd, 1H), 7.33-7.32 (m, 4H), 7.25-7.24 (m, 1H), 6.27 (br d, 1H), 5.72 (s, 1H), 4.40 (t, 1H), 3.42-3.34 (m, 4H), 3.27-3.23 (m, 2H), 3.16-3.11 (m, 2H), 2.13 (m, 1H), 1.07 (d, 3H), 0.96 (d, 3H). MS (ESI) m/z: Calculated: 454.26; Observed: 477.3 (M$^+$+Na).

5-Fluoro-N-(2-methyl-1-phenylpropyl)-2-nitrobenzenamine

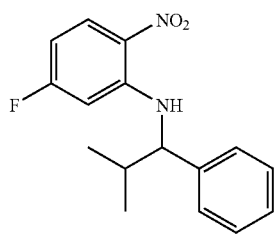

A solution of 2-methyl-1-phenylpropan-1-amine (1.0 g, 6.7 mmol), 2,4-difluoronitrobenzene (0.74 mL, 6.7 mmol) and N,N-diisopropylethylamine (2.3 mL, 13.4 mmol) in acetonitrile was stirred at room temperature for 32 h. The solvent was concentrated in vacuo, the residue was taken up in dichloromethane and washed with water, dried, and concentrated under reduced pressure to yield 1.79 g (93%) of the desired aniline: $^1$H NMR (400 MHz, CDCl$_3$): δ 8.78 (br d, 1H), 8.21 (dd, 1H), 7.37-7.31 (m, 4H), 7.28-7.24 (m, 1H), 6.44-6.35 (m, 2H), 4.43 (t, 1H), 2.18 (m, 1H), 1.06 (d, 3H), 0.97 (d, 3H).

2-Methyl-1-phenylpropan-1-amine

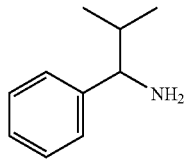

A solution of isobutyrophenone (5.1 mL, 33.7 mmol) and formic acid (1.3 mL, 33.7 mmol) in formamide was stirred at 165-180° C. for 20 h. The mixture was cooled, diluted with water, and extracted with benzene. The benzene was concentrated down and the residue was boiled in 3 M HCl (10 mL) for 48 h. The cooled reaction mixture was added to diethyl ether and extracted with water. The combined water extracts were basified with 20% NaOH, and extracted with dichloromethane. The combined extracts were washed with brine, dried (Na$_2$SO$_4$) and concentrated in vacuo to yield 3.09 g (61%) of the desired amine: $^1$H NMR (400 MHz, CD$_3$OD): δ 7.33-7.23 (m, 4H), 7.22-7.20 (m, 1H), 3.49 (d, 1H), 1.87 (m, 1H), 1.00 (d, 3H), 0.73 (d, 3H). MS (ESI) m/z: Calculated: 149.12; Observed: 149.9 (M⁺+1).

EXAMPLE 11

1-(2-(3,5-Dimethoxybenzylamino)-4-(piperazin-1-yl)phenyl)-2,2,2-trifluoroethanone hydrochloride

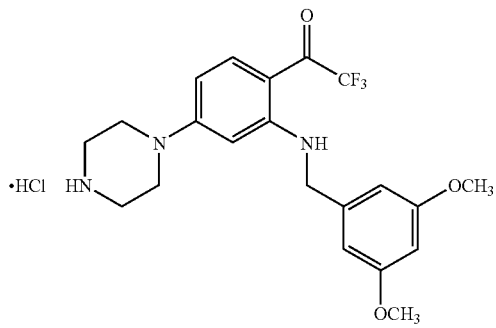

A saturated solution of HCl gas in anhydrous diethyl ether was added portion wise to a solution of tert-butyl 4-(3-(3,5-dimethoxybenzylamino)-4-(2,2,2-trifluoroacetyl)-phenyl)piperazine-1-carboxylate (230 mg, 0.44 mmol) in anhydrous dichloromethane (1.5 mL). The resulting mixture was allowed to stand at room temperature for 30 min, and conversion was monitored by LCMS. The supernatant was pipetted out and the residue was concentrated down in vacuo and co-evaporated with diethyl ether to yield 150 mg (81%) of the title compound: ¹H NMR (400 MHz, CD₃OD): δ 7.65 (dd, 1H), 6.54 (d, 2H), 6.42-6.39 (m, 2H), 6.07 (d, 1H), 4.48 (br s, 2H), 3.76 (s, 6H), 3.63-3.60 (m, 4H), 3.30-3.25 (m, 4H). MS (ESI) m/z: Calculated: 423.18; Observed: 847.4 (2M⁺+1)

t-Butyl 4-(3-(3,5-dimethoxybenzylamino)-4-(2,2,2-trifluoroacetyl)phenyl)-piperazine-1-carboxylate

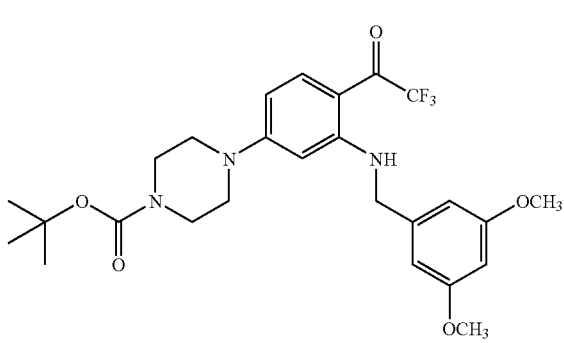

A solution of 1-(2-(3,5-dimethoxybenzylamino)-4-fluorophenyl)-2,2,2-trifluoroethanone (527 mg, 1.47 mmol), N-Boc-piperazine (296 mg, 1.62 mmol) and N,N-diisopropylethylamine (0.51 mL, 2.94 mmol) in acetonitrile was stirred at reflux for 48 h. The reaction mixture was cooled down and concentrated under reduced pressure. The residue was taken up in dichloromethane, washed with water, dried and concentrated in vacuo to yield 1.04 g of the crude aniline. The crude product was purified by PTLC (20% ethyl acetate in hexanes) to yield 230 mg (30%) of tert-butyl 4-(3-(3,5-dimethoxybenzylamino)-4-(2,2,2-trifluoroacetyl)phenyl)piperazine-1-carboxylate: ¹H NMR (400 MHz, CD₃OD): δ 9.32 (br t, 1H), 7.63 (dd, 1H), 6.50 (d, 2H), 6.37 (t, 1H), 6.19 (dd, 1H), 5.81 (d, 1H), 4.39 (d, 2H), 3.77 (s, 6H), 3.52-3.49 (m, 4H), 3.35-3.32 (m, 4H), 1.48 (s, 9H). MS (ESI) m/z: Calculated: 523.23; Observed: 546.3 (M⁺+23).

1-(2-(3,5-Dimethoxybenzylamino)-4-fluorophenyl)-2,2,2-trifluoroethanone

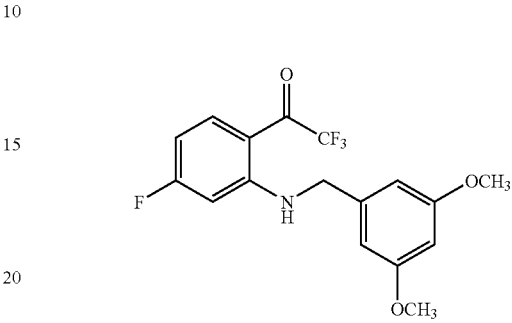

A solution of (3,5-dimethoxyphenyl)methanamine (0.88 g, 5.20 mmol), 2,2,2-trifluoro-1-(2,4-difluorophenyl)ethanone (1.0 g, 4.80 mmol) and diisopropylethylamine (1.6 mL, 9.6 mmol) in acetonitrile was stirred at 40° C. for 48 h. The solvent was concentrated in vacuo, the residue was taken up in dichloromethane and washed with water and brine, dried, and concentrated under reduced pressure to yield 1.73 g of a yellow oil. The residue was purified by PTLC (20% ethyl acetate in hexanes) to give 527 mg (35%) of the desired aniline: ¹H NMR (400 MHz, CDCl₃) δ 9.27 (br t, 1H), 7.83 (br s, 1H), 6.47-6.40 (m, 5H), 4.42 (d, 2H), 3.79 (s, 6H).

EXAMPLE 12

N-(1-(3-Bromophenyl)ethyl)-2-nitro-5-(piperazin-1-yl)benzenamine hydrochloride

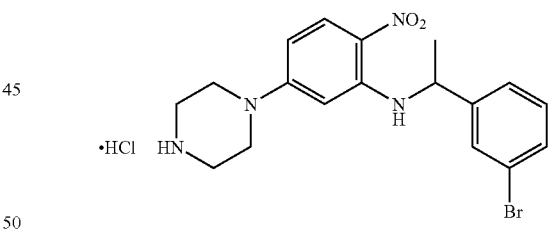

A mixture of tert-butyl 4-(3-(1-(3-bromophenyl)ethylamino)-4-nitrophenyl)piperazine-1-carboxylate (0.45 g, 0.9 mmol), 2N HCl in ether (10 mL, 20.0 mmol) and dichloromethane (5 mL) was stirred for 18 h and concentrated in vacuo. The residue was dissolved in dichloromethane; this solution was washed with aqueous NaHCO₃ solution, dried over Na₂SO₄ and concentrated in vacuo. The yellow solid residue was dissolved in dichloromethane (0.5 mL) and reacted with 1N HCl in ether (1 mL). The resulting precipitates were collected by vacuum filtration, washed with ether and air dried to yield the title compounds as a yellow solid (0.13 g, 33%). ¹H NMR (400 MHz, CDCl₃): δ 8.71 (d, 1H), 8.05 (d, 1H), 7.50 (s, 1H), 7.39 (m, 1H), 7.23 (m, 2H), 6.19 (dd, 1H), 5.60 (d, 1H), 4.53 (m, 1H), 3.21 (m, 2H), 3.13 (m, 2H), 2.88 (m, 4H), 1.63 (d, 3H). MS (ESI) m/z: Calculated: 404; Observed: 405 (M+H⁺).

t-Butyl 4-(3-(1-(3-bromophenyl)ethylamino)-4-nitrophenyl)piperazine-1-carboxylate

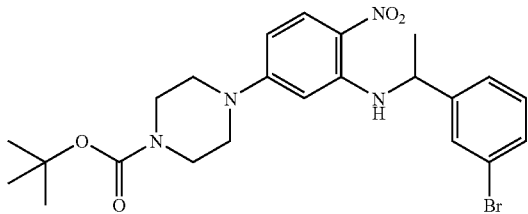

A mixture of N-(1-(3-bromophenyl)ethyl)-5-fluoro-2-nitrobenzenamine (1.25 g, 3.7 mmol), tert-butyl piperazine-1-carboxylate (0.7 g, 3.7 mmol), diisopropylethylamine (1.0 mL, 5.7 mmol) and acetonitrile (20 mL) was heated at reflux for 18 h, cooled to room temperature and concentrated in vacuo. The residue was dissolved in ethyl acetate; this solution was washed with water, dried over $Na_2SO_4$ and concentrated in vacuo. The residue was purified by flash column chromatography on silica gel using 10%-15% ethyl acetate in hexanes as eluent to yield the title compounds as a yellow solid (0.45 g, 24%). $^1$H NMR (400 MHz, $CDCl_3$): δ 8.72 (d, 1 H), 8.10 (d, 1H), 7.51 (s, 1H), 7.40 (m, 1H), 7.24 (m, 2H), 6.17 (dd, 1H), 5.60 (d, 1H), 4.52 (m, 1H), 3.48 (m, 4H), 3.26 (m, 2H), 3.13 (m, 2H), 1.63 (d, 3H), 1.44 (s, 9H). MS (ESI) m/z: Calculated: 504; Observed: 505 (M+H$^+$).

N-(1-(3-Bromophenyl)ethyl)-5-fluoro-2-nitrobenzenamine

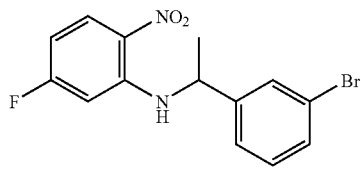

A mixture of 1-(3-bromophenyl)ethanamine (1.0 g, 5.0 mmol), 2,4-difluoro-1-nitrobenzene (0.8 g, 5.0 mmol), N,N-diisopropylethylamine (1.7 mL, 10.0 mmol) and acetonitrile (20 mL) was stirred for 18 h and concentrated in vacuo. The residue was dissolved in ethyl acetate; this solution was washed with water, dried over $Na_2SO_4$ and concentrated in vacuo to yield the title compounds as a yellow oil (1.25 g, 74%). $^1$H NMR (400 MHz, $CDCl_3$): δ 8.51 (d, 1H), 8.25 (m, 1H), 7.48 (s, 1H), 7.41 (m, 1H), 7.25 (m, 2H), 6.36 (m, 1H), 6.24 (m, 1H), 4.55 (m, 1H), 1.63 (d, 3H). MS (ESI) m/z: Calculated: 338; Observed: 339 (M+H$^+$).

1-(3-Bromophenyl)ethanamine

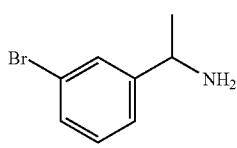

A mixture of 3-bromoacetophenone (10.0 g, 50 mmol), formic acid (12.0 g, 250 mmol) and formamide (50 mL) was heated at 165-180° C. with stirring for 24 h. The reaction mixture was cooled to room temperature and extracted with toluene; the extract was concentrated in vacuo. The residue was mixed with 3N hydrochloric acid (20 mL) and heated at reflux for 48 h, cooled to room temperature, washed with ether and neutralized with 20% aqueous NaOH solution. The neutralized solution was extracted with ether; the extract was dried over solid KOH and concentrated in vacuo to provide the title compounds as a light brown oil (5.7 g, 57%). $^1$H NMR (400 MHz, $CDCl_3$): δ 7.53 (s, 1H), 7.37 (d, 1H), 7.29 (d, 1H), 7.21 (t, 1H), 4.14 (br d, 3H), 1.39 (d, 3H). MS (ESI) m/z: Calculated: 199; Observed: 200 (M+H$^+$).

EXAMPLE 13

1-(2-(3,5-Dichlorobenzylamino)-4-(piperazin-1-yl)phenyl)-2,2,2-trifluoroethanone hydrochloride

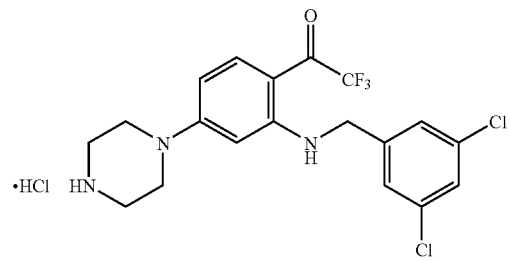

A mixture of tert-butyl 4-(3-(3,5-dichlorobenzylamino)-4-(2,2,2-trifluoroacetyl)phenyl)-piperazine-1-carboxylate (0.25 g, 0.5 mmol), trifluoroacetic acid (5 mL) and dichloromethane (10 mL) was stirred for 3 h and concentrated in vacuo. The residue was dissolved in dichloromethane; this solution was washed with aqueous $NaHCO_3$ solution, dried over $Na_2SO_4$ and concentrated in vacuo. The yellow solid residue was dissolved in dichloromethane (1 mL), reacted with 1 N HCl in ether (1 mL) and concentrated in vacuo to yield the title compounds as a yellow solid (0.16 g, 73%). $^1$H NMR (400 MHz, $CDCl_3$): δ 9.37 (br, 1H), 7.62 (d, 1H), 7.28 (s, 1H), 7.22 (s, 2H), 6.24 (dd, 1H), 5.71 (d, 1H), 4.43 (d, 2H), 3.30 (m, 4H), 2.93 (m, 4H). MS (ESI) m/z: Calculated: 431; Observed: 432 (M+H$^+$).

t-Butyl 4-(3-(3,5-dichlorobenzylamino)-4-(2,2,2-trifluoroacetyl)phenyl)piperazine-1-carboxylate

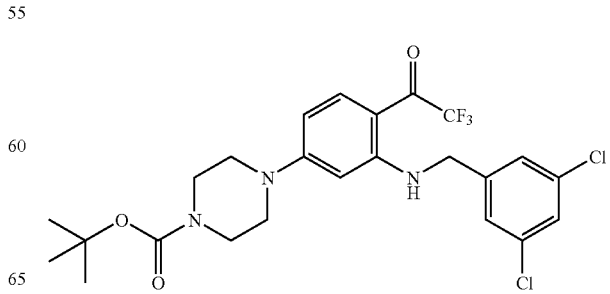

A mixture of 1-(2-(3,5-dichlorobenzylamino)-4-fluorophenyl)-2,2,2-trifluoroethanone (0.78 g, 2.1 mmol), t-butyl piperazine-1-carboxylate (0.41 g, 2.2 mmol), N,N-diisopropylethylamine (0.8 mL, 4.4 mmol) and acetonitrile (10 mL) was heated at reflux for 18 h, cooled to room temperature and concentrated in vacuo. The residue was dissolved in ethyl acetate; this solution was washed with water, dried over $Na_2SO_4$ and concentrated in vacuo. The residue was purified by flash column chromatography on silica gel using 10% ethyl acetate in hexanes as eluent to yield the title compounds as a yellow solid (0.31 g, 28%). $^1H$ NMR (400 MHz, $CDCl_3$): δ 9.38 (br, 1H), 7.67 (d, 1H), 7.31 (s, 1H), 7.21 (s, 2H), 6.13 (dd, 1H), 5.70 (d, 1H), 4.42 (d, 2H), 3.54 (m, 4H), 3.38 (m, 4H), 1.49 (s, 9H). MS (ESI) m/z: Calculated: 531; Observed: 532 ($M+H^+$).

1-(2-(3,5-Dichlorobenzylamino)-4-fluorophenyl)-2,2,2-trifluoroethanone

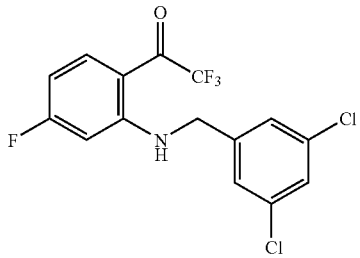

A mixture of 2,2,2,2',4'-pentafluoroacetophenone (1.05 g, 5.0 mmol), 3,5-dichlorobenzylamine (0.88 g, 5.0 mmol), N,N-diisopropylethylamine (1.7 mL, 10.0 mmol) and acetonitrile (25 mL) was heated at reflux for 18 h, cooled and concentrated in vacuo. The residue was dissolved in ethyl acetate; this solution was washed with water, dried over $Na_2SO_4$ and concentrated in vacuo. The residue was purified by flash column chromatography on silica gel using 5% ethyl acetate in hexanes as eluent to yield the title compounds as a yellowish solid (0.78 g, 43%). $^1H$ NMR (400 MHz, $CDCl_3$): δ 9.28 (br s, 1H), 7.88 (m, 1H), 7.34 (s, 1H), 7.22 (s, 2H), 6.44 (m, 1H), 6.30 (dd, 1H), 4.43 (d, 2H).

EXAMPLE 14

4-Methoxy-N-(1-phenyl)ethyl)-3-(piperazin-1-yl)benzenamine hydrochloride

The title compound has the following formula.

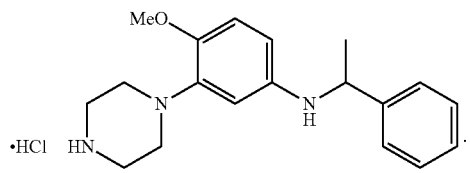

EXAMPLE 15

N-(3-Bromobenzyl)-2-nitro-5-(piperazin-1-yl)benzenamine dihydrochloride

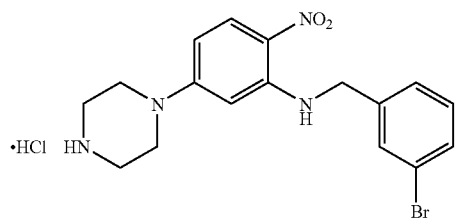

To a solution of t-butyl 4-(3-(3-bromobenzylamino)-4-nitrophenyl)piperazine-1-carboxylate (104 mg, 0.23 mmol) in dry dichloromethane (1.0 mL) was added a saturated solution of HCl in diethyl ether (15 mL). The reaction mixture was stirred for 4 hours. The solvent was evaporated and the precipitate was recrystallized from methanol (0.3 mL), dichloromethane (0.5 mL) and diethyl ether (5 mL). The product was collected by filtration and dried in vacuo to afford the title compound (35.0 mg, 39% yield after recrystallization). $^1H$ NMR (400 MHz, $CD_3OD$): δ 8.07 (d, 1H), 7.42 (s, 1H), 7.33 (m, 2H), 7.28 (m, 1H), 6.40 (d, 1H), 6.03 (s, 1H), 4.61 (s, 1H), 3.56 (m, 4H), 3.27 (m, 4H); MS (ESI) m/z: Calculated for $C_{17}H_{20}ClN_4O_2$: 347.13; Observed: 347.5 ($M^++1$).

t-Butyl 4-(3-(3-bromobenzylamino)-4-nitrophenyl)piperazine-1-carboxylate

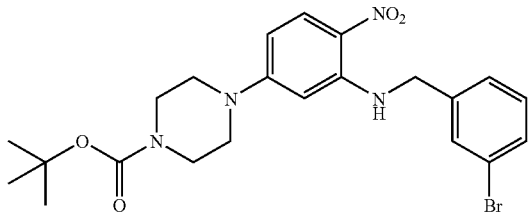

N-(3-Bromobenzyl)-5-fluoro-2-nitrobenzenamine (624 mg, 2.2 mmol), t-butyl piperazine-1-carboxylate (414 mg, 2.2 mmol), N,N-diisopropylethylamine (287 mg, 2.2 mmol) were stirred at 80° C. in dry acetonitrile (10 mL) for 16 h. The solvent was evaporated and the residue was dissolved in dichloromethane and washed with water. The dichloromethane was evaporated and the crude compound was purified by silica chromatography using 25% ethyl acetate in hexanes to afford the title compound (316 mg, 32% yield). $^1H$ NMR (400 MHz, $CDCl_3$): δ 8.77 (s, 1H), 8.05 (d, 1H), 7.32-7.21 (m, 4H), 6.18 (d, 1H), 5.72 (s, 1H), 4.46 (d, 2H), 3.49 (m, 4H), 3.27 (m, 4H), 1.45 (s, 9H); MS (ESI) m/z: Calculated for $C_{22}H_{27}ClN_4O_4Na$ 469.16; Observed: 469.4 ($M^++Na$).

N-(3-Bromobenzyl)-5-fluoro-2-nitrobenzenamine

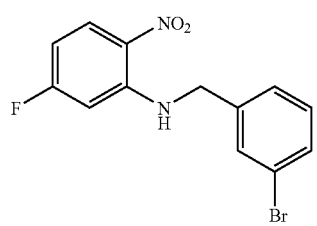

2,4-Difluoronitrobenzene (2.9 g, 18.1 mmol), 3-Bromobenzylamine (2.6 g, 18.1 mmol) and N,N-diisopropylethylamine (2.4 g, 18.1 mmol) were stirred in acetonitrile (25 mL) at room temperature for 2 hours. The solvent was evaporated and the crude mixture was dissolved in dichloromethane and washed with water. The dichloromethane was evaporated in vacuo to collect the title compound (4.8 g, 95% yield). $^1$H NMR (400 MHz, CDCl$_3$): δ 8.55 (s, 1H), 8.25 (dd, 1H), 7.32-7.21 (m, 4H), 6.41 (m, 2H), 4.50 (d, 2H).

EXAMPLE 16

N-(1-(3,5-Dimethyl[[y]]phenyl)ethyl)-2-nitro-5-(piperazin-1-yl)benzenamine hydrochloride

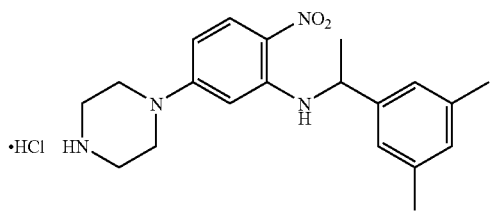

To a solution of t-butyl 4-(3-(1-(3,5-dimethylphenyl)ethylamino)-4-nitrophenyl)piperazine-1-carboxylate (327 mg, 0.67 mmol) in dry dichloromethane (2.0 mL) was added a saturated solution of HCl in diethyl ether (15 mL). The reaction mixture was stirred for 4 hours. The product was collected by filtration and dried in vacuo to afford the title compound (216 mg, 76% yield). $^1$H NMR (400 MHz, CD$_3$OD): δ 8.03 (d, 1H), 6.55 (s, 2H), 6.36 (m, 2H), 5.95 (s, 1H), 4.67 (m, 1H), 3.73 (s, 6H), 3.49 (m, 4H), 3.29 (m, 4H), 1.60 (d, 3H).

t-Butyl 4-(3-(1-(3,5-dimethylphenyl)ethylamino)-4-nitrophenyl)piperazine-1-carboxylate

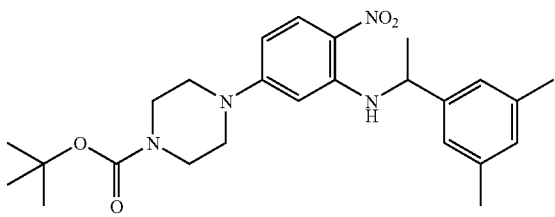

5-fluoro-N-(1-(3,5-dimethylphenyl)ethyl)-2-nitrobenzenamine (762 mg, 2.4 mmol), t-butyl piperazine-1-carboxylate (443 mg, 2.4 mmol), N,N-diisopropylethylamine (614 mg, 4.8 mmol) were stirred at 80° C. in dry acetonitrile (50 mL) for 48 h. The solvent was evaporated and the residue was dissolved in dichloromethane and washed with water. The dichloromethane was evaporated and the crude compound was purified by silica chromatography using 25% ethyl acetate in hexanes to afford the title compound (469 mg, 41% yield). $^1$H NMR (400 MHz, CDCl$_3$): δ 8.68 (s, 1H), 8.05 (d, 1H), 6.49 (s, 2H), 6.33 (s, 1H), 6.14 (d, 1H), 5.70 (s, 1H), 4.47 (m, 1H), 3.76 (s, 6H), 3.43 (m, 4H), 3.23 (m, 2H), 3.15 (m, 2H), 1.62 (d, 3H), 1.46 (s, 9H).

5-Fluoro-N-(1-(3,5-dimethylphenyl)ethyl)-2-nitrobenzenamine

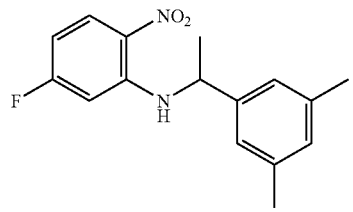

1-(3,5-Dimethylphenyl)ethanamine (670 mg, 4.2 mmol), 2,4-difluoronitrobenzene (764 mg, 4.2 mmol) and N,N-diisopropylethylamine (1.08 mg, 8.4 mmol) were stirred at room temperature in dry acetonitrile (50 mL) for 6 h. The solvent was evaporated and the residue was dissolved in dichloromethane and washed with water. The dichloromethane was evaporated to collect the title compound (820 mg, 61% yield). $^1$H NMR (400 MHz, CDCl$_3$): δ 8.49 (s, 1H), 8.19 (m, 1H), 6.45 (s, 2H), 6.30 (m, 3H), 4.48 (m, 1H), 3.76 (s, 6H), 1.62 (d, 3H).

EXAMPLE 17

1-(2-(3-Bromobenzylamino)-4-(piperazin-1-yl)phenyl)-2,2,2-trifluoroethanone hydrochloride The title compound has the following formula.

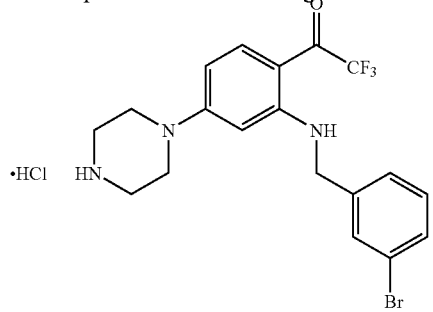

EXAMPLE 18

N-[[(1-]](3-Bromobenzyl)[[ethyl]]-2-(methylsulfonyl)-5-(piperazin-1-yl)[[phenyl)]]-benzeneamine hydrochloride The title compound has the following formula.

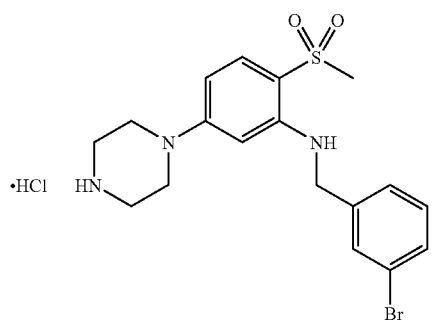

EXAMPLE 19

N-(1-(3-Chloro-4,5-dimethoxyphenyl)ethyl-2-(methylsulfonyl)-5-(piperazin-1-yl)-benzeneamine hydrochloride The title compound has the following formula.

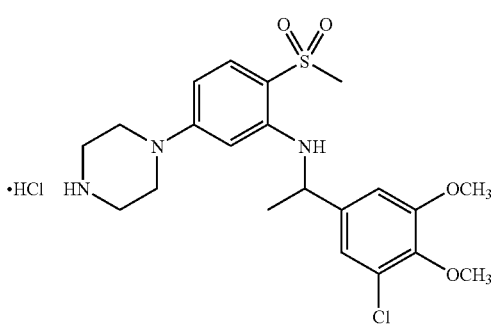

EXAMPLE 20

N-(1-(3-Chloro-5-methoxyphenyl)ethyl-2-(methylsulfonyl)-5-(piperazin-1-yl)-benzeneamine hydrochloride The title compound has the following formula.

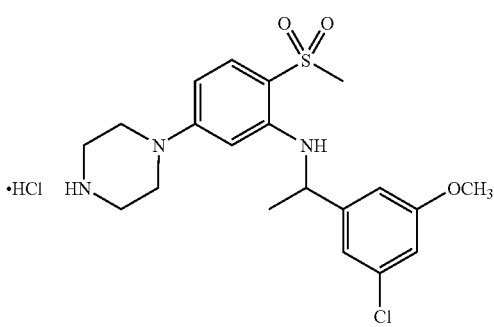

EXAMPLE 21

N-(1-(3-Trifluoromethylphenyl)ethyl-2-(methylsulfonyl)-5-(piperazin-1-yl)-benzeneamine hydrochloride The title compound has the following formula.

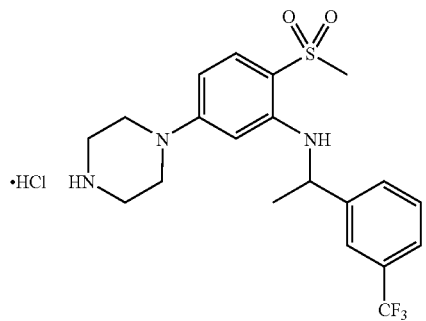

EXAMPLE 22

(S)-1-(2-(1-Phenylethylamino)-4-(piperazin-1-yl)phenyl)-2,2,2-trifluoroethanone hydrochloride

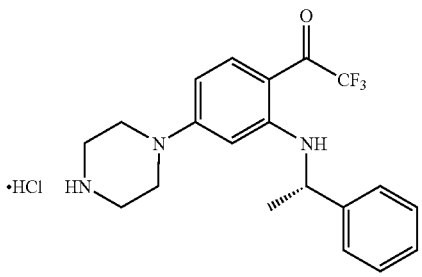

To a solution of t-butyl 4-(3-(1-phenylethylamino)-4-(2,2,2-trifluoroacetyl)phenyl)piperazine-1-carboxylate (50 mg, 0.1 mmol) in dry dichloromethane (1.0 mL) was added a saturated solution of HCl in diethyl ether (20 mL). The reaction mixture was stirred for 2 h. The solvent was removed by rotary evaporation to afford the title compound (31 mg, 72% yield). $^1$H NMR (400 MHz, CD$_3$OD): δ 7.63 (d, 1H), 7.36 (m, 5H), 6.36 (d, 1H), 5.86 (s, 1H), 4.75 (m, 1H), 3.52 (m, 2H), 3.45 (m, 2H), 3.17 (m, 4H), 1.60 (d, 3H); MS (ESI) m/z: Calculated for C$_{20}$H$_{23}$F$_3$N$_3$O: 378.18; Observed: 378.5 (M$^+$+1).

EXAMPLE 23

(R)-1-(2-(1-Phenylethylamino)-4-(piperazin-1-yl)phenyl)-2,2,2-trifluoroethanone hydrochloride

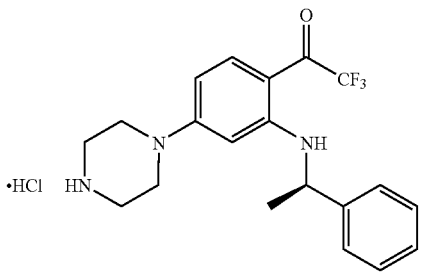

To a solution of t-butyl 4-(3-(1-phenylethylamino)-4-(2,2,2-trifluoroacetyl)phenyl)piperazine-1-carboxylate (50 mg, 0.1 mmol) in dry dichloromethane (1.0 mL) was added a saturated solution of HCl in diethyl ether (20 mL). The reaction mixture was stirred for 2 h. The solvent was removed by rotary evaporation to afford the title compound (31 mg, 72% yield). $^1$H NMR (400 MHz, CD$_3$OD): δ 7.63 (d, 1H), 7.36 (m, 5H), 6.36 (d, 1H), 5.86 (s, 1H), 4.75 (m, 1H), 3.52 (m, 2H), 3.45 (m, 2H), 3.17 (m, 4H), 1.60 (d, 3H); MS (ESI) m/z: Calculated for C$_{20}$H$_{23}$F$_3$N$_3$O: 378.18; Observed: 378.5 (M$^+$+1).

EXAMPLE 24

N-(1-(3,5-Dimethoxyphenyl)ethyl-2-(methylsulfonyl)-5-(piperazin-1-yl)-benzeneamine hydrochloride

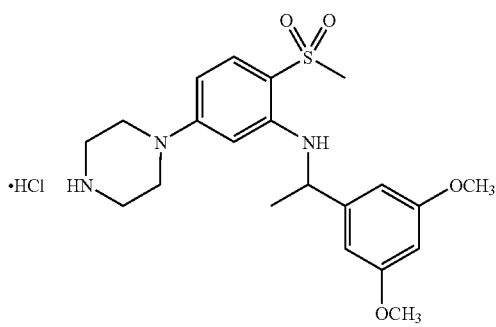

To a solution of N-(1-(3,5-dimethoxyphenyl)ethyl-2-(methylsulfonyl)-5-(piperazin-1-yl)-benzeneamine (500 mg, 1.19 mmol) in dichloromethane (5.0 mL) was added 1M solution of HCl in diethyl ether (25 mL). The reaction mixture was stirred for 3 h. The solvent was removed by rotary evaporation to afford the title compound (521 mg, 96% yield). $^1$H NMR (400 MHz, CD$_3$OD): δ 7.55 (m, 1H), 6.57 (s, 3H), 6.36 (m, 1H), 5.49 (s, 1H), 4.61 (m, 1H), 3.75 (s, 6H), 3.41 (m, 4H), 3.25 (m, 4H), 3.18 (m, 2H), 3.21 (s, 3H), 1.55 (d, 3H); MS (ESI) m/z: Calculated for C$_{21}$H$_{30}$ClN$_3$O$_4$S: 455.16; Observed: 456.2 (M$^+$+1).

N-(1-(3,5-Dimethoxyphenyl)ethyl-2-(methylsulfonyl)-5-(piperazin-1-yl)-benzeneamine

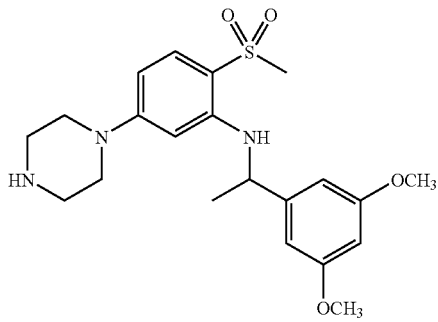

A mixture of 5-fluoro-N-(3,5-dimethoxyphenyl)ethyl)-2-(methylsulfonyl)benzeneamine (883 mg, 2.5 mmol) and piperazine (861 mg, 10.0 mmol) in dry acetonitrile (5 mL) were refluxed for 48 h. The solvent was evaporated and the residue was dissolved in dichloromethane and washed with water. The dichloromethane was evaporated and the crude compound was purified by silica chromatography using 2% methanol in dichloromethane to afford the title compound (702 mg, 67% yield). $^1$H NMR (400 MHz, CDCl$_3$): δ 7.56 (d, 1H), 6.51 (m, 3H), 6.32 (m, 1H), 6.22 (dd, 1H), 5.87 (m, 1H), 4.44 (m, 1H), 3.75 (s, 6H), 3.22 (m, 4H), 3.14 (m, 3H), 2.95 (m, 4H), 1.56 (d, 3H); MS (ESI) m/z: Calculated for C$_{21}$H$_{29}$N$_3$O$_4$S: 419.54; Observed: 420.2 (M$^+$+1).

5-Fluoro-N-(3,5-dimethoxyphenyl)ethyl)-2-(methylsulfonyl)benzeneamine has the following formula

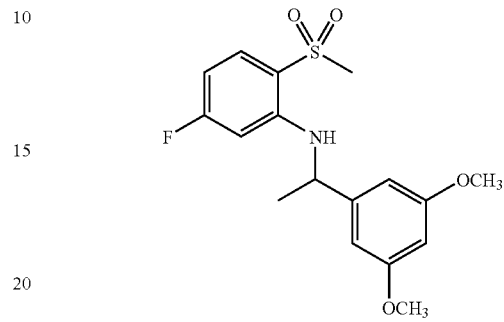

EXAMPLE 25

[1-(5-Chloro-2,3-dimethoxy-phenyl)-ethyl]-(2-methanesulfonyl-5-piperazin-1-yl-phenyl)-amine hydrochloride

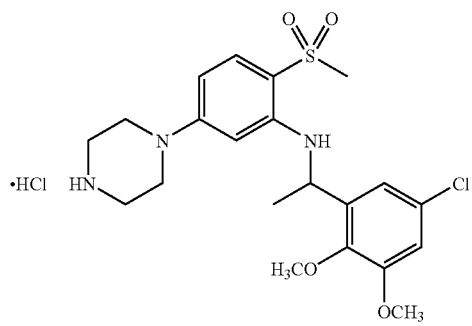

[1-(5-Chloro-2,3-dimethoxy-phenyl)-ethyl]-(2-methanesulfonyl-5-piperazin-1-yl-phenyl)-amine (10 mg, 0.022 mmol) was dissolved in dichloromethane (1.5 mL) and ether (1.5 mL). The solution was cooled in a bath with dry ice and methanol. Hydrochloric acid (0.5 mL, 2.0 M in ether) was added slowly. The mixture was warmed to room temperature. The solvents were concentrated down in vacuo and co-evaporated with diethyl ether gave [1-(5-chloro-2,3-dimethoxyphenyl)-ethyl]-(2-methanesulfonyl-5-piperazin-1-yl-phenyl)-amine hydrochloride salt as a white solid (10.6 mg): $^1$H NMR (400 MHz, CD$_3$OD): $^1$H NMR (400 MHz, CD$_3$OD): δ 7.51 (d, 1H), 6.92 (m, 2H), 6.37 (dd, 1H), 6.09 (d, 1H), 4.93 (m, 1H), 3.90 (s, 3H), 3.86 (s, 3H), 3.48 (m, 4H), 3.24 (m, 4H), 3.05 (s, 3H), 1.49 (d, 3H). MS (ESI) m/z: Calculated: 453.98 free base; Observed: 454.4 (M+H$^+$); 476.4 (M+Na$^+$); 930.8 (2M+Na$^+$). Salt: Mol. Wt.: 490.44 (C$_{21}$H$_{29}$Cl$_2$N$_3$O$_4$S).

[1-(5-Chloro-2,3-dimethoxy-phenyl)-ethyl]-(2-methanesulfonyl-5-piperazin-1-yl-phenyl)-amine

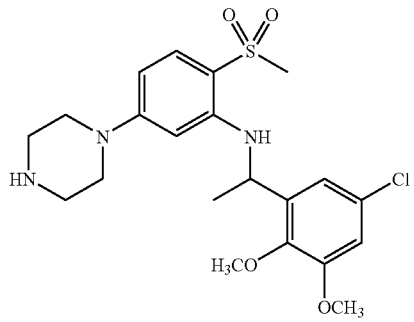

A solution of [1-(5-chloro-2,3-dimethoxy-phenyl)-ethyl]-(5-fluoro-2-methanesulfonyl-phenyl)-amine (0.52 g, 1.34 mmol), piperazine (0.23 g, 2.68 mmol) and N,N-diisopropylethylamine (0.47 mL, 2.68 mmol) in acetonitrile was stirred at 80° C. for 24 h. The reaction mixture was cooled down and concentrated under reduced pressure. The residue was taken up in dichloromethane, washed with water, dried and concentrated in vacuo to yield the crude residue which was purified by preparative TLC (0.5% $NH_4OH$/9.5% methanol/dichloromethane) to afford [1-(5-chloro-2,3-dimethoxy-phenyl)-ethyl]-(2-methanesulfonyl-5-piperazin-1-yl-phenyl)-amine (17 mg, 3%). $^1$H NMR (400 MHz, $CD_3OD$): δ 7.42 (d, 1H), 6.87 (m, 2H), 6.25 (dd, 1H), 5.90 (s, 1H), 4.87 (m, 1H), 3.85 (s, 1H), 3.81 (s, 1H), 3.05-3.2 (m, 4H), 3.78 (m, 4H), 1.49 (d, 3H). MS (ESI) m/z: Calculated: 453.98; Observed: 454.4 $(M+H^+)$; 476.4 $(M+Na^+)$; 930.8 $(2M+Na^+)$. Mol. Wt.: 453.98 $(C_{21}H_{28}ClN_3O_4S)$.

[1-(5-Chloro-2,3-dimethoxy-phenyl)-ethyl]-(5-fluoro-2-methanesulfonyl-phenyl)-amine

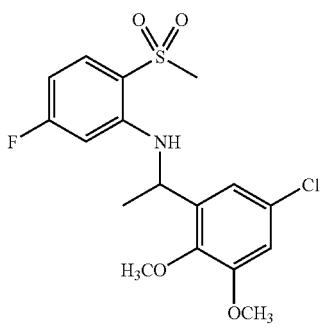

A solution of 1-(5-chloro-2,3-dimethoxy-phenyl)-ethyl amine (1.27 g, 5.89 mmol), 2,4-difluoro-1-methanesulfonyl-benzene (1.25 g, 6.48 mmol) and N,N-diisopropylethylamine (2.1 mL, 11.78 mmol) in acetonitrile was stirred at 80° C. for 48 h. The solvent was concentrated in vacuo, the residue was taken up in dichloromethane and washed with water, dried, and concentrated under reduced pressure to the crude compound which was purified by silica gel column (20% ethyl acetate in hexanes) to afford [1-(5-chloro-2,3-dimethoxy-phenyl)-ethyl]-(5-fluoro-2-methanesulfonyl-phenyl)-amine (700 mg, 32%): $^1$H NMR (400 MHz, $CDCl_3$): δ 7.74 (dd, 1H), 6.82 (m, 2H), 6.73 (dd, 1H), 6.42 (dd, 1H), 6.24 (dd, 1H), 4.82 (m, 1H), 3.95 (s 3 H), 3.88 (s, 3H), 3.27 (3, 3H), 1.58 (s, 3H).

1-(5-Chloro-2,3-dimethoxy-phenyl)-ethyl amine

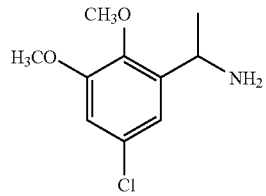

To a stirred solution of 1-(5-chloro-2,3-dimethoxy-phenyl)-ethanone (3.6 g, 16.8 mmol) and ammonium acetate (12.9 g, 168 mmol) in absolute methanol (50 mL) was added sodium cyanoborohydride (0.738 g, 11.8 mmol) in one portion. The resulting solution was stirred at room temperature for 36 h. Concentrated HCl was added until pH<2. The methanol was then evaporated, and the resulting white residue was dissolved in $H_2O$ (50 mL) and washed with diethyl ether (2×50 mL). The aqueous phase was then basified with powdered KOH to pH>10, saturated with NaCl, and extracted with dichloromethane (4×10 mL). The combined dichloromethane extracts were dried over $Na_2SO_4$, filtered, and evaporated to the crude compound which was purified by silica gel column (1% $NH_4OH$/8% methanol/dichloromethane) to afford 1-(5-chloro-2,3-dimethoxy-phenyl)-ethyl amine (1.43 g, 40%): $^1$H NMR (400 MHz, $CDCl_3$): δ 6.98 (d, 1H), 6.78 (d, 1H), 4.39 (m, 1H), 3.86 (s, 3H), 3.83 (s, 3 H), 1.35 (d, 3H).

1-(5-Chloro-2,3-dimethoxy-phenyl)-ethanone

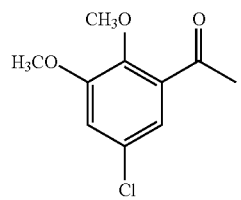

To a solution of 1-(5-chloro-2,3-dimethoxy-phenyl)-ethanol (5.67 g, 26.8 mmol) in acetone (200 mL) at room temperature was added a previously prepared solution of Jones Reagent ($H_2O$—$H_2SO_4$—$CrO_3$, 100 mL/22 mL/20 g) (100 mL, dropwise). The reaction was stirred for 3 h, and then concentrated. The mixture was dissolved in ethyl acetate (200 mL) and washed with 3.0 N aqueous NaOH and brine. The organic phase was dried over $Na_2SO_4$, filtered over silica gel, and concentrated to the crude compound which was purified by silica gel column (20% ethyl acetate in hexanes) to afford 1-(5-chloro-2,3-dimethoxy-phenyl)-ethanone (3.65 g, 63%): $^1$H NMR (400 MHz, $CDCl_3$): δ 7.20 (d, 1H), 7.00 (d, 1H), 3.89 (s, 6H), 2.62 (d, 3H).

1-(5-Chloro-2,3-dimethoxy-phenyl)-ethanol

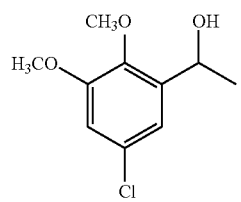

To a stirred solution of 5-chloro-2,3-dimethoxy-benzaldehyde (7.0 g, 34.90 mmol) in dry diethyl ether (500 mL) at 0° C. was added methylmagnesium bromide of 3.0 M in diethyl ether (29 mL, 87.22 mmol). The reaction mixture was brought to room temperature and stirred for 30 min; refluxed for 3 h; then cooled to 0° C. and quenched by adding saturated aqueous NH₄Cl. The two liquid layers were separated. The aqueous layer was extracted with diethyl ether. The combined organic layers were washed with water, dried, and concentrated to the crude compound which was purified by silica gel column (10-25% ethyl acetate in hexanes) to afford 1-(5-chloro-2,3-dimethoxy-phenyl)-ethanol (5.67 g, 75%): $^1$H NMR (400 MHz, CDCl$_3$): δ 7.00 (d, 1H), 6.81 (d, 1H), 5.11 (m, 1H), 3.86 (s, 6H), 2.30 (d, 1H), 1.48 (d, 3H).

EXAMPLE 26

N-(2-(Methylsulfonyl)-5-(piperazin-1-yl)phenyl)naphthalen-1-amine hydrochloride

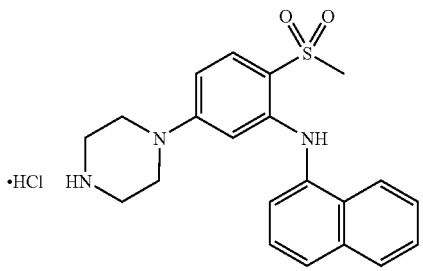

To a solution of N-(2-(methylsulfonyl)-5-(piperazin-1-yl)phenyl)naphthalen-1-amine (120.0 mg, 0.31 mmol) in dichloromethane (2 mL) was added 0.4 mL of 1 M HCl in diethyl ether. The solution was allowed to stir for 1 h, after which a precipitate formed. The solvent was removed by rotary evaporation to collect the title compound (122.0 mg, 0.29 mmol) in 94% yield. $^1$H NMR (400 MHz, CD$_3$OD): δ 7.94 (d, 1H), 7.91 (d, 1H), 7.84 (d, 1H), 7.73 (d, 1H), 7.50 (m, 4H), 6.60 (d, 1H), 6.29 (s, 1H), 3.47 (m, 4H), 3.21 (m, 4H), 3.19 (s, 3H); MS (ESI) m/z: Calculated for C$_{21}$H$_{24}$N$_3$O$_2$S: 382.2; Observed: 382.4 (M$^+$+1).

N-(2-(Methylsulfonyl)-5-(piperazin-1-yl)phenyl)naphthalen-1-amine

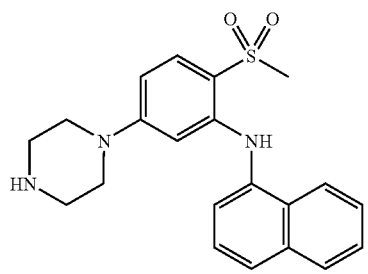

N-(5-Fluoro-2-(methylsulfonyl)phenyl)naphthalen-1-amine (0.56 g, 1.7 mmol), piperazine (0.46 g, 5.3 mmol), N,N-diisopropylethylamine (0.89 g, 6.8 mmol) were stirred at 80° C. in dry acetonitrile (5 mL) for 48 h. The solvent was evaporated and the residue was dissolved in dichloromethane and washed with water. The dichloromethane was evaporated and the crude compound was purified by silica chromatography using 10% methanol in dichloromethane to afford the title compound (120 mg, 18% yield). $^1$H NMR (400 MHz, CDCl$_3$): δ 8.10 (s, 1H), 7.89 (d, 1H), 7.83 (d, 1H), 7.66 (d, 1H), 7.62 (m, 1H), 7.39 (m, 4H), 6.35 (d, 1H), 6.26 (s, 1H), 3.09 (s, 3H), 2.98 (m, 4H), 2.79 (m, 4H); MS (ESI) m/z: Calculated for C$_{21}$H$_{24}$N$_3$O$_2$S: 382.2; Observed: 382.4 (M$^+$).

N-(5-Fluoro-2-(methylsulfonyl)phenyl)naphthalen-1-amine

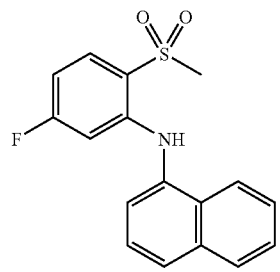

Naphthalen-1-amine (0.89 g, 4.7 mmol) and 60% NaH in oil (0.24 g, 6.1 mmol) were stirred in N,N-dimethylformamide (5 mL) for 15 min. at 0° C. and for 30 min. at room temperature. 2,4-Difluoro-1-(methylsulfonyl)benzene (0.67 g, 4.7 mmol), was added to the reaction as a solid. The reaction was allowed to stir at room temperature for 16 h. The reaction was poured in water and extracted with ether. After removal of solvent the crude was purified on silica chromatography in 10% ethyl acetate in hexanes to obtain 0.56 g of product (0.36 mg, 38% yield). $^1$H NMR (400 MHz, CDCl$_3$): δ 8.30 (s, 1H), 7.89 (m, 3H), 7.54 (m, 5H), 6.79 (t, 1H), 6.48 (d, 1H), 3.22 (s, 3H).

EXAMPLE 27

1,2,3,4-Tetrahydro-N-(2-(methylsulfonyl)-5-(piperazin-1-yl)phenyl)naphthalen-1-amine hydrochloride

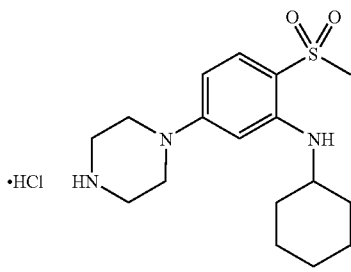

A solution of 1,2,3,4-tetrahydro-N-(2-(methylsulfonyl)-5-(piperazin-1-yl)phenyl)naphthalen-1-amine (57 mg, 0.18 mmol) in anhydrous dichloromethane (1 mL) was cooled to 0° C. and HCl (0.18 mL of a 1M solution in diethyl ether, 0.18 mmol) were added. The mixture was allowed to warm up to rt for 15 min, diethyl ether was added and a white solid was formed. The supernatant was removed, and the solid rinsed with diethyl ether, the remaining solvent was removed by rotary evaporation to yield 47 mg (75%) of 1,2,3,4-tetrahydro-N-(2-(methylsulfonyl)-5-(piperazin-1-yl)phenyl)naphthalen-1-amine: $^1$H NMR (400 MHz, CD$_3$OD): δ 7.58 (d, 1H), 7.28 (d, 1H), 7.20-7.14 (m, 3H), 6.45-6.43 (m, 2H), 4.85 (dd, 1H), 3.60-3.54 (m, 4H), 3.38-3.30 (m, 4H), 2.93 (s, 3H), 2.90-2.74 (m, 2H), 2.06-2.00 (m, 2H), 1.94-1.85 (m, 2H). MS (ESI) m/z: Calculated: 385.52; Observed: 386.4 (M$^+$+1).

1,2,3,4-Tetrahydro-N-(2-(methylsulfonyl)-5-(piperazin-1-yl)phenyl)naphthalen-1-amine

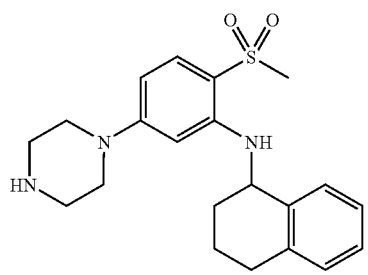

A solution of N-(5-fluoro-2-(methylsulfonyl)phenyl)-1,2,3,4-tetrahydronaphthalen-1-amine (720 mg, 2.26 mmol), piperazine (583 mg, 6.77 mmol) and N,N-diisopropylethylamine (1.2 mL, 6.77 mmol) in acetonitrile (10 mL) was stirred at reflux for 16 h. The reaction mixture was cooled down and concentrated under reduced pressure. The residue was taken up in dichloromethane, washed with water, dried and concentrated in vacuo to yield 1.04 g of the crude aniline. The crude product was purified by PTLC (20% ethyl acetate in hexanes) to yield 257 mg (30%) of 1,2,3,4-tetrahydro-N-(2-(methylsulfonyl)-5-(piperazin-1-yl)phenyl)naphthalen-1-amine: $^1$H NMR (400 MHz, CD$_3$OD): δ 7.60 (d, 1H), 7.30 (d, 1H), 7.20-7.10 (m, 2H), 6.32-6.26 (m, 2H), 6.23 (br s, 1H), 4.67 (dd, 1H), 3.26 (br t, 4H), 2.98 (br t, 4H), 2.92 (s, 3H), 2.90-2.72 (m, 2H), 2.02-1.80 (m, 4H). MS (ESI) m/z: Calculated: 385.52; Observed: 386.2 (M$^+$+1).

N-(5-Fluoro-2-(methylsulfonyl)phenyl)-1,2,3,4-tetrahydronaphthalen-1-amine

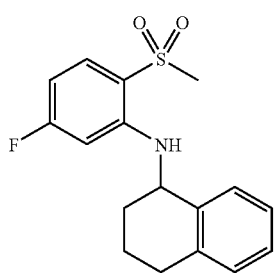

A solution of 1,2,3,4-tetrahydronaphthalen-1-amine (0.82 mL, 5.73 mmol), 2,4-difluoro-1-(methylsulfonyl)benzene (1.1 g, 5.73 mmol) and diisopropylethylamine (2.0 mL, 11.46 mmol) in CH$_3$CN (15 mL) was stirred at 60° C. for 48 h. The solvent was concentrated in vacuo, the residue was taken up in dichloromethane and washed with water and brine, dried, and concentrated under reduced pressure to yield 2.1 g of a yellow oil. The residue was purified by PTLC (20% ethyl acetate in hexanes) to give 720 mg (39%) of the desired aniline: $^1$H NMR (400 MHz, CDCl$_3$) δ 7.78 (dd, 1H), 7.28-7.13 (m, 3H), 6.60 (dd, 1H), 6.51-6.45 (m, 2H), 4.62 (dd, 1H), 2.96 (s, 3H), 2.91-2.74 (m, 2H), 2.05-1.98 (m, 2H), 1.91-1.85 (m, 2H). MS (ESI) m/z: Calculated: 319.39; Observed: 661.0 (2M$^+$+23).

EXAMPLE 28

2-(Methylsulfonyl)-N-(1-phenylethyl)-5-(piperazin-1-yl)benzenamine hydrochloride

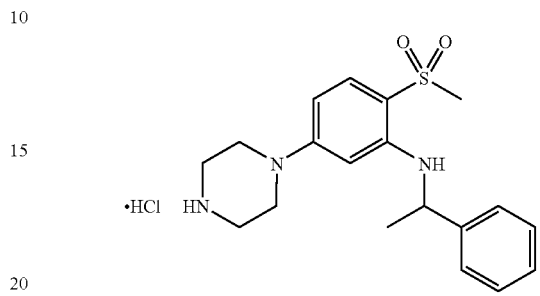

To a solution of 2-(methylsulfonyl)-N-(1-phenyl)ethyl)-5-(piperazin-1-yl)benzenamine (0.04 mmol) in dichloromethane (1 mL) was added 10 mL of 1 M HCl in ether. The solution was allowed to stir for 1 h after which a precipitate formed. The solvent was removed by rotary evaporation to collect the title compound in quantitative yield. $^1$H NMR (400 MHz, CD$_3$OD): δ 8.10 (s, 1H), 7.55 (s, 1H), 7.30 (d, 1H), 7.21 (q, 1H), 7.02 (d, 1H), 6.39 (d, 1H), 4.66 (m, 1H), 3.92 (s, 3H), 3.40 (m, 4H), 3.26 (m, 4H), 1.53 (d, 3H); MS (ESI) m/z: Calculated for C$_{19}$H$_{26}$ClN$_3$O$_2$S: 395.95; Observed: 396.1 (M$^+$+1).

2-(Methylsulfonyl)-N-(1-phenyl)ethyl)-5-(piperazin-1-yl)benzenamine is a synthetic intermediate having the following formula

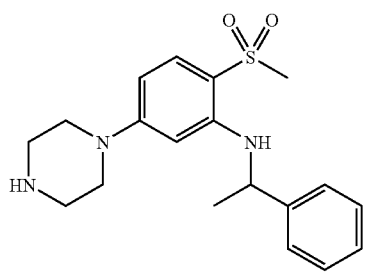

5-Fluoro-2-(methylsulfonyl) N-(1-(1-phenyl)ethyl)-benzenamine

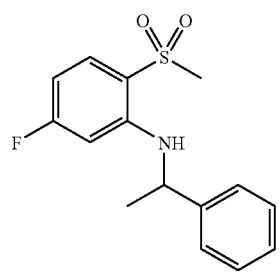

2,4-Difluoro-1-(methylsulfonyl)benzene (2.9 mmol), 1-phenylethyl amine (2.9 mmol) and N,N-diisopropylethylamine (5.9 mmol) were stirred at 65° C. in N,N-dimethylformamide (20 mL) for 24 h. The solvent was evaporated and the residue was dissolved in dichloromethane and washed with water. The dichloromethane was evaporated and purified by silica chromatography in 20% ethyl acetate in hexanes to collect the title compound (59% yield). $^1$H NMR (400 MHz, CDCl$_3$): δ 7.74 (q, 1H), 7.18 (m, 2H), 6.84 (d, 1H), 6.79 (d, 1H), 6.42 (t, 1H), 6.17 (d, 1H), 4.78 (m, 1H), 3.91 (s, 3H), 3.08 (s, 3H), 1.52 (d, 3H).

EXAMPLE 29

N-(1-(3,5-Dichlorophenyl)ethyl)-2-(methylsulfonyl)-5-(piperazin-1-yl)benzeneamine hydrochloride

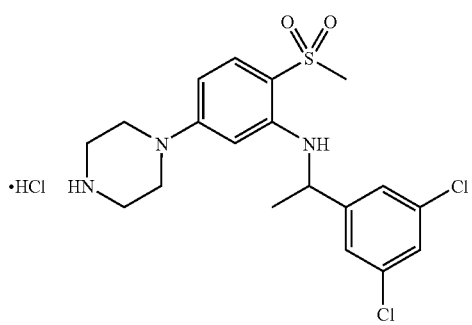

To a solution of N-(1-(3,5-dichlorophenyl)ethyl)-2-(methylsulfonyl)-5-(piperazin-1-yl)benzeneamine (0.09 mmol) in dichloromethane (2.0 mL) was added a saturated solution of HCl in diethyl ether (15 mL). The reaction mixture was stirred for 2 h. The solvent was removed by rotary evaporation to afford the title compound in 95% yield. $^1$H NMR (400 MHz, CD$_3$OD): δ 7.67 (d, 1H), 7.37 (s, 2H), 7.35 (s, 1H), 6.41 (d, 1H), 5.84 (s, 1H), 4.79 (m, 1H), 3.57 (m, 4H), 3.25 (m, 4H), 1.61 (d, 3H); MS (ESI) m/z: Calculated for C$_{19}$H$_{24}$Cl$_3$N$_3$O$_2$S: 464.8; Observed: 465.5 (M$^+$+1).

N-(1-(3,5-Dichlorophenyl)ethyl)-2-(methylsulfonyl)-5-(piperazin-1-yl)benzeneamine

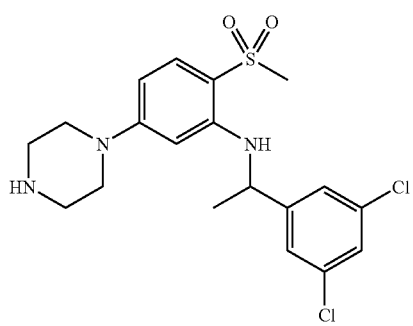

N-(1-(3,5-Dichlorophenyl)ethyl)-5-fluoro-2-(methylsulfonyl)benzenamine (600 mg, 1.62 mmol), t-butyl piperazine-1-carboxylate (0.29 mmol), N,N-diisopropylethylamine (0.58 mmol) were stirred at 60° C. in dry acetonitrile (20 mL) for 3 days. The solvent was evaporated and the residue was dissolved in dichloromethane and washed with water. The dichloromethane was evaporated and the crude compound was purified by silica chromatography using 20% ethyl acetate in hexanes to afford the title compound (49% yield). $^1$H NMR (400 MHz, CDCl$_3$): δ 9.31 (d, 1H), 7.63 (d, 1H), 7.25 (s, 1H), 7.22 (s, 2H), 6.18 (d, 1H), 5.53 (s, 1H), 4.48 (m, 1H), 3.48 (m, 4H), 3.25 (m, 4H), 1.60 (d, 3H), 1.47 (s, 9H); MS (ESI) m/z: Calculated for C$_{19}$H$_{23}$Cl$_2$N$_3$O$_2$S: 428.3; Observed: 429.4 (M$^+$+1).

N-(1-(3,5-Dichlorophenyl)ethyl)-5-fluoro-2-(methylsulfonyl)benzenamine

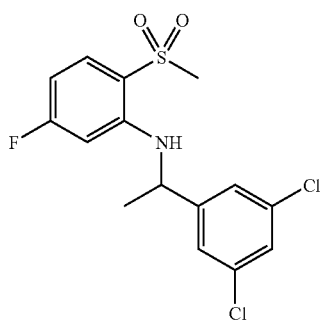

2,4-Difluoro-1-(methylsulfonyl)benzene (3.13 mmol), 1-(3,5-dichlorophenyl)ethanamine (3.13 mmol) and N,N-diisopropylethylamine (6.3 mmol) were stirred at 45° C. in dry acetonitrile (25 mL) for 16 h. The solvent was evaporated and the residue was dissolved in dichloromethane and washed with water. The dichloromethane was evaporated and purified by silica chromatography in 20% ethyl acetate in hexanes to collect the title compound (9% yield). $^1$H NMR (400 MHz, CDCl$_3$): δ 9.23 (s, 1H), 7.87 (t, 1H), 7.28 (s, 1H), 7.19 (s, 2H), 6.41 (t, 1H), 6.11 (d, 1H), 4.51 (m, 1H), 1.62 (d, 3H).

EXAMPLE 30

N-(1-(6-Chloro-2,3-dihydrobenzo[b][1,4]dioxin-8-yl)ethyl)-2-(methylsulfonyl)-5-(piperazin-1-yl)benzenamine hydrochloride

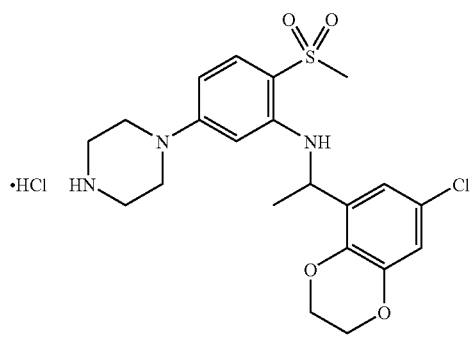

A solution of N-(1-(6-chloro-2,3-dihydrobenzo[b][1,4]dioxin-8-yl)ethyl)-2-(methylsulfonyl)-5-(piperazin-1-yl)benzenamine (50.0 mg, 0.11 mmol) in anhydrous dichloromethane (1 mL) was cooled to 0° C. and HCl (0.12 mL of a 1 M solution in diethyl ether, 0.12 mmol) was added. The mixture was allowed to stir for 30 min. The solvent was removed by rotary evaporation, more diethyl ether was added to precipitate the salt. After removal of solvent by rotary evaporation the desired product was collected (53 mg, 99%). $^1$H NMR (400 MHz, CD$_3$OD): δ 7.55 (d, 1H), 6.87 (d, 1H), 6.76 (d, 1H), 6.40 (dd, 1H), 6.02 (d, 1H), 4.84 (m, 1H), 4.33 (m, 2H), 4.27 (m, 2H), 4.43 (m, 4H), 3.30 (m, 4H), 3.07 (s, 3H), 1.54 (d, 3H); MS (ESI) m/z: 452.3 (M$^+$+1).

N-(1-(6-Chloro-2,3-dihydrobenzo[b][1,4]dioxin-8-yl)ethyl)-2-(methylsulfonyl)-5-(piperazin-1-yl)benzenamine

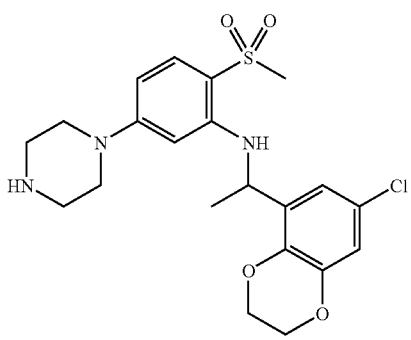

A solution of 1-(6-chloro-2,3-dihydrobenzo[b][1,4]dioxin-8-yl)ethanamine (130 mg, 0.61 mmol), 2,4-difluoro-1-(methylsulfonyl)benzene (116 mg, 0.61 mmol) and diisopropylethylamine (314 mg, 2.43 mmol) in N,N-dimethylformamide (2 mL) was stirred at 110° C. for 16 h. The reaction was cooled to room temperature, poured over water and extracted with diethyl ether. The solvent was concentrated in vacuo to collect 53.4 mg of the desired product, which was used for the next reaction without further purification. A solution of N-(1-(6-chloro-2,3-dihydrobenzo[b][1,4]dioxin-8-yl)ethyl)-5-fluoro-2-(methylsulfonyl)benzenamine (53.4 mg, 0.14 mmol), piperazine (239 mg, 2.76 mmol) and N,N-diisopropylethylamine (0.25 mL, 1.38 mmol) in acetonitrile (2 mL) was stirred at reflux for 16 h. The reaction mixture was cooled down and concentrated under reduced pressure. The residue was taken up in dichloromethane, washed with water, dried and concentrated in vacuo. The crude product was purified by silica chromatography (10% ethyl acetate in hexanes) to yield 50 mg (80%) of desired product. $^1$H NMR (400 MHz, CDCl$_3$): δ 7.58 (d, 1H), 6.82 (d, 1H), 6.76 (d, 1H), 6.60 (d, 1H), 6.23 (d, 1H), 5.87 (d, 1H), 4.73 (m, 1H), 4.28 (m, 4H), 3.24 (m, 4H), 3.05 (s, 3H), 3.03 (m, 4H), 1.54 (d, 3H); MS (ESI) m/z: 452.3 (M$^+$+1).

1-(6-Chloro-2,3-dihydrobenzo[b][1,4]dioxin-8-yl)ethanamine

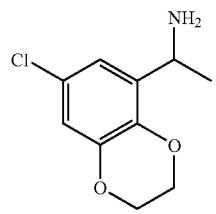

1-(6-Chloro-2,3-dihydrobenzo[b][1,4]dioxin-8-yl)ethanone (248 mg, 1.17 mmol), titanium(IV) isopropoxide (0.84 mL, 2.33 mmol) and 2 M solution of ammonia in ethanol (2.90 mL, 5.83 mmol) were stirred at room temperature for 6 h. The reaction was cooled to 0° C. and sodium borohydride was added portionwise during 10 min. (0.66 mg, 1.76 mmol); the resultant mixture was stirred at rt for an additional 3 h. The reaction was quenched by pouring it into ammonium hydroxide (2 M, 20 mL), the precipitate that formed was filtered off and washed with ethyl acetate (10 mL×3). The organic layer was separated and the remaining aqueous layer was extracted with ethyl acetate (10 mL×2). The combined organic extracts were washed with 1 M HCl (10 mL). The acidic aqueous extracts were washed with ethyl acetate (25 mL), then treated with aqueous sodium hydroxide (2 M) to pH 10-12, and extracted with ethyl acetate (25 mL×3). The combined organic extracts were washed with brine (10 mL), dried (Na$_2$SO$_4$), and concentrated in vacuo to afford the desired product (130 mg, 61% yield). $^1$H NMR (400 MHz, CDCl$_3$): δ 6.87 (d, 1H), 6.75 (d, 1H), 4.24 (m, 5H), 1.35 (d, 3H).

1-(6-Chloro-2,3-dihydrobenzo[b][1,4]dioxin-8-yl)ethanone

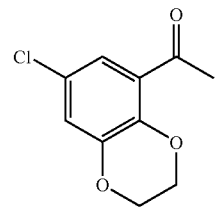

1-(6-Chloro-2,3-dihydrobenzo[b][1,4]dioxin-8-yl)ethanol (258 mg, 1.20 mmol) was dissolved in 4 mL of dichloromethane. PCC (648 mg, 3.00 mmol) was added portionwise and the mixture was stirred for 16 h (reaction is likely to be completed earlier). Diethyl ether (20 mL) was added and stirred for 10 minutes. The heterogeneous mixture was filtered through a plug of celite. The solvent was removed by rotary evaporation to collect the desired product (248 mg, 97%). $^1$H NMR (400 MHz, CDCl$_3$): δ 7.28 (d, 1H), 7.01 (d, 1H), 4.33 (m, 4H), 2.59 (s, 3H).

1-(6-Chloro-2,3-dihydrobenzo[b][1,4]dioxin-8-yl)ethanol

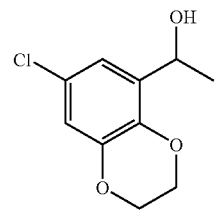

7-Chloro-2,3-dihydrobenzo[b][1,4]dioxine-5-carbaldehyde (0.26 g, 1.32 mmol) was dissolved in 10 mL of diethyl ether and cooled to 0° C. MeMgBr (1.1 mL, 3.31 mmol) was added to the solution and the ice bath was removed. The reaction was allowed to stir at rt for 10 min. and at reflux for 30 min. The reaction was cooled to 0° C. and 10 mL of sat NH$_4$Cl were added to quench the reaction. The diethyl ether layer was separated and washed with water (20 mL×2). The organic layer was dried over Na$_2$SO$_4$ and the solvent was removed by rotary evaporation to collect the desired product (258 mg, 91%). $^1$H NMR (400 MHz, CDCl$_3$): δ 6.91 (s, 1H), 6.77 (s, 1H), 5.02 (m, 1H), 4.24 (m, 4H), 1.45 (d, 3H).

7-Chloro-2,3-dihydrobenzo[b][1,4]dioxine-5-carbaldehyde

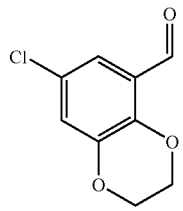

The title compound was prepared in 40.5% (0.26 g) yield from 5-chloro-2-hydroxy-3-methoxybenzaldehyde following the published procedure in WO 2004110344, which is incorporated by reference herein in its entirety.

EXAMPLE 31

N-(2-(methylsulfonyl)-5-(piperazin-1-yl)phenyl)benzo[b]thiophen-3-amine hydrochloride

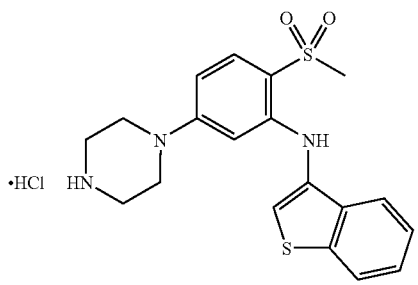

To a solution of N-(2-(methylsulfonyl)-5-(piperazin-1-yl)phenyl)benzo[b]thiophen-3-amine (0.05 mmol) in dichloromethane (2 mL) at 0° C. was added 30 µL of 2 M HCl in diethyl ether. The solution was allowed to stir for 10 minutes after which a precipitate formed. The solvent was removed by rotary evaporation to collect the title compound in 91% yield. $^1$H NMR (400 MHz, CD$_3$OD): δ 8.24 (s, 1H), 7.98 (m, 1H), 7.65 (d, 1H), 7.54 (m, 2H), 7.22 (s, 1H), 6.49 (m, 2H), 3.20 (s, 3H), 3.17 (m, 4H), 2.94 (m, 4H); MS (ESI) m/z: 388.2 (M$^+$+1).

N-(2-(Methylsulfonyl)-5-(piperazin-1-yl)phenyl)benzo[b]thiophen-3-amine

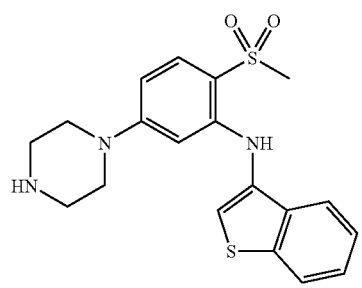

A solution of benzo[b]thiophen-3-amine (1.1 mmol), 2,4-difluoro-1-(methylsulfonyl)benzene (1.1 mmol) and N,N-diisopropylethylamine (4.00 mmol) in N,N-dimethylformamide (2 mL) was stirred at 110° C. for 16 h. The reaction was cooled to room temperature, poured over water and extracted with diethyl ether. The solvent was concentrated in vacuo and the residue was used without further purification for the following reaction. N-(5-fluoro-2-(methylsulfonyl)phenyl)benzo[b]thiophen-3-amine (0.3 mmol), piperazine (8.0 mmol), N,N-diisopropylethylamine (4.00 mmol) were stirred at 80° C. in dry acetonitrile (3 mL) for 16 h. The solvent was evaporated and the residue was dissolved in dichloromethane and washed with water. The dichloromethane was evaporated and the crude compound was purified by silica chromatography using 10% methanol in dichloromethane to afford the title compound (16% yield). $^1$H NMR (400 MHz, CDCl$_3$): δ 8.12 (s, 1H), 7.88 (m, 1H), 7.71 (d, 1H), 7.71 (m, 1H), 7.66 (m, 1H), 7.14 (s, 1H), 6.46 (d, 1H), 6.41 (dd. 1H), 3.13 (s, 3H), 3.11 (m, 4H), 2.91 (m, 4H); MS (ESI) m/z: 388.2 (M$^+$+1).

EXAMPLE 32

1,2,3,4-Tetrahydro-6,7-dimethoxy-N-(2-(methylsulfonyl)-5-(piperazin-1-yl)phenyl)naphthalen-1-amine hydrochloride

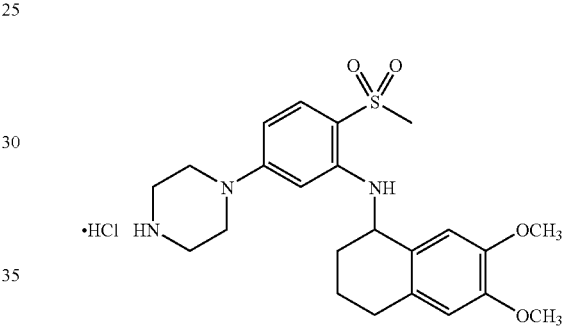

To a solution of 1,2,3,4-tetrahydro-6,7-dimethoxy-N-(2-(methylsulfonyl)-5-(piperazin-1-yl)phenyl)naphthalen-1-amine (20.0 mg, 0.05 mmol) in dichloromethane (2 mL) at 0° C. was added 29 µL of 2 M HCl in diethyl ether. The solution was allowed to stir for 10 minutes after which a precipitate formed. The solvent was removed by rotary evaporation to collect the title compound (25.0 mg, 0.05 mmol) in 100% yield. $^1$H NMR (400 MHz, CD$_3$OD): δ 7.54 (d, 1H), 6.73 (s, 1H), 6.65 (s, 1H), 6.51 (dd, 1H), 6.43 (d, 1H), 6.38 (m, 1H), 5.90 (m, 1H), 3.81 (s, 3H), 3.79 (s, 3H), 3.54 (m, 4H), 3.34 (m, 4H), 3.02 (s, 3H), 2.69 (m, 2H), 2.25 (m, 2H); MS (ESI) m/z: 446.4 (M$^+$+1).

1,2,3,4-Tetrahydro-6,7-dimethoxy-N-(2-(methylsulfonyl)-5-(piperazin-1-yl)phenyl)naphthalen-1-amine

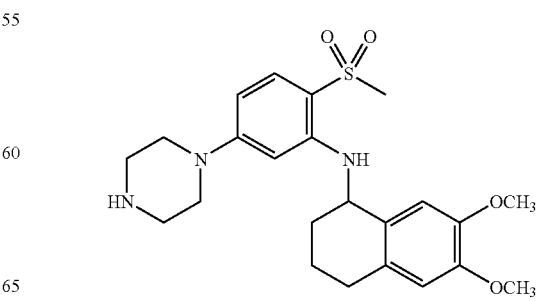

A solution of 1,2,3,4-tetrahydro-6,7-dimethoxynaphthalen-1-amine (200.0 mg, 0.96 mmol), 2,4-difluoro-1-(methylsulfonyl)benzene (185.0 mg, 0.96 mmol) and diisopropylethylamine (496.0 mg, 3.84 mmol) in N,N-dimethylformamide (2 mL) was stirred at 110° C. for 16 h. The reaction was cooled to room temperature, poured over water and extracted with diethyl ether. The solvent was concentrated in vacuo and the residue was used without further purification for the following reaction. N-(5-Fluoro-2-(methylsulfonyl)phenyl)-1,2,3,4-tetrahydro-6,7-dimethoxynaphthalen-1-amine (150 mg, 0.40 mmol), piperazine (683 mg, 7.90 mmol), N,N-diisopropylethylamine (510 mg, 4.00 mmol) were stirred at 80° C. in dry acetonitrile (3 mL) for 16 h. The solvent was evaporated and the residue was dissolved in dichloromethane and washed with water. The dichloromethane was evaporated and the crude compound was purified by silica chromatography using 10% methanol in dichloromethane to afford the title compound (30 mg, 17% yield). $^1$H NMR (400 MHz, CDCl$_3$): δ 7.63 (d, 1H), 6.79 (s, 1H), 6.59 (s, 1H), 6.31 (m, 2H), 6.25 (d, 1H), 4.62 (m, 1H), 3.87 (s, 3H), 3.78 (s, 3H), 3.30 (m, 4H), 3.02 (m, 4H), 2.94 (s, 3H), 2.72 (m, 2H), 1.84 (m, 4H); MS (ESI) m/z: 446.3 (M$^+$+1).

1,2,3,4-Tetrahydro-6,7-dimethoxynaphthalen-1-amine

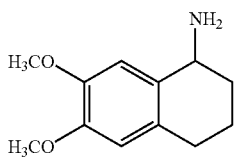

3,4-Dihydro-6,7-dimethoxynaphthalen-1(2H)-one (5.00 g, 24.2 mmol), titanium(IV) isopropoxide (14.1 mL, 48.5 mmol) and 2 M solution of ammonia in ethanol (60.6 mL, 121 mmol) were stirred at room temperature for 6 h. The reaction was cooled to 0° C. and sodium borohydride was added portionwise during 10 min. (1.37 g, 36.4 mmol); the resultant mixture was stirred at rt for an additional 3 h. The reaction was quenched by pouring it into ammonium hydroxide (2 M, 130 mL), the precipitate that formed was filtered off and washed with ethyl acetate (25 mL×3). The organic layer was separated and the remaining aqueous layer was extracted with ethyl acetate (25 mL×2). The combined organic extracts were washed with 1 M HCl (50 mL). The acidic aqueous extracts were washed with ethyl acetate (100 mL), then treated with aqueous sodium hydroxide (2 M) to pH 10-12, and extracted with ethyl acetate (75 mL×3). The combined organic extracts were washed with brine (75 mL), dried (Na$_2$SO$_4$), and concentrated in vacuo to afford the desired product (200 mg, 4% yield). $^1$H NMR (400 MHz, CDCl$_3$): δ 6.95 (s, 1H), 6.56 (s, 1H), 3.92 (m, 1H), 3.88 (s, 3H), 3.85 (s, 3H), 2.71 (m, 2H), 1.97 (m, 2H), 1.76 (m, 2H).

EXAMPLE 33

1,2,3,4-Tetrahydro-5,8-dimethoxy-N-(2-(methylsulfonyl)-5-(piperazin-1-yl)phenyl)naphthalen-1-amine

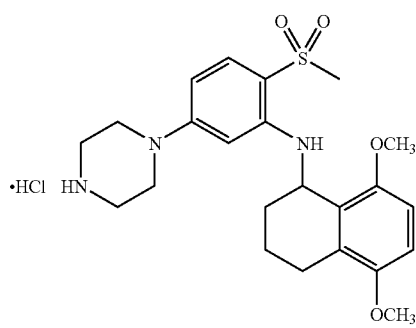

A solution of N-(5-fluoro-2-(methylsulfonyl)phenyl)-1,2,3,4-tetrahydro-5,8-dimethoxynaphthalen-1-amine (1.234 g, 3.26 mmol), piperazine (5.63 g, 65.1 mmol) and N,N-diisopropylethylamine (5.7 mL, 32.6 mmol) in acetonitrile (20 mL) was stirred at reflux for 16 h. The reaction mixture was cooled down and concentrated under reduced pressure. The residue was taken up in dichloromethane, washed with water, dried and concentrated in vacuo to yield 1.04 g of the crude aniline. The crude product was purified by PTLC (20% ethyl acetate in hexanes) to yield 610 mg (42%) of 1,2,3,4-tetrahydro-5,8-dimethoxy-N-(2-(methylsulfonyl)-5-(piperazin-1-yl)phenyl)naphthalen-1-amine: $^1$H NMR (400 MHz, CD$_3$OD): δ 7.49 (d, 1H), 6.81 (d, 1H), 6.76 (d, 1H), 6.38-6.36 (m, 2H), 5.98 (d, 1H), 4.80 (br s, 1H), 3.79 (s, 3H), 3.67 (s, 3H), 3.37-3.32 (m, 4H), 2.98-2.92 (m, 1H), 2.88-2.82 (m, 7H), 2.44-2.36 (m, 1H), 2.20 (br d, 1H0, 1.86-1.58 (m, 3H). MS (ESI) m/z: Calculated: 445.20; Observed: 446.2 (M$^+$+1).

N-(5-Fluoro-2-(methylsulfonyl)phenyl)-1,2,3,4-tetrahydro-5,8-dimethoxynaphthalen-1-amine

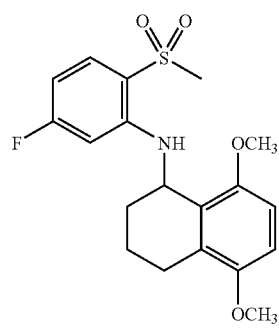

A solution of 1,2,3,4-tetrahydro-5,8-dimethoxynaphthalen-1-amine (1.1 g mL, 5.31 mmol), 2,4-difluoro-1-(methylsulfonyl)benzene (1.02 g, 5.31 mmol) and diisopropylethylamine (3.7 mL, 21.26 mmol) in N,N-dimethylformamide (10 mL) was stirred at 90° C. for 16 h. The reaction mixture was diluted with water and extracted with diethyl ether. The combined extracts were washed with water and brine, dried, and concentrated under reduced pressure to yield 1.95 g of a yellow oil. The residue was purified by PTLC (25% ethyl acetate in hexanes) to give 1.26 g (63%) of the desired aniline: $^1$H NMR (400 MHz, CDCl$_3$) δ 7.40 (dd, 1H), 6.73 (d, 1H), 6.66 (m, 2H), 6.44 (dt, 1H), 6.22 (br d, 1H), 4.79 (br s, 1H), 3.80 (s, 3H), 3.67 (s, 3H), 2.96-2.88 (m, 4H), 2.46-2.37 (m, 1H), 2.17-2.12 (br d, 1H), 1.92-1.84 (m, 1H), 1.78-1.60 (m, 2H). MS (ESI) m/z: Calculated: 379.13; Observed: 402.2 (M$^+$+23).

1,2,3,4-Tetrahydro-5,8-dimethoxynaphthalen-1-amine

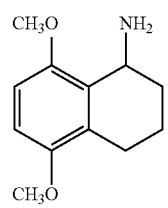

3,4-Dihydro-5,8-dimethoxynaphthalen-1(2H)-one (5 g, 24.2 mmol), titanium(IV) isopropoxide (14.2 mL, 48.5 mmol) and 2 M solution of ammonia in ethanol (60.6 mL, 121.2 mmol) were stirred at room temperature for 6 h. The reaction was cooled to 0° C. and sodium borohydride was added portionwise during 10 min. (1.4 g, 36.4 mmol); the resultant mixture was stirred at rt for an additional 3 h. The reaction was quenched by pouring it into ammonium hydroxide (2 M, 60 mL), the precipitate that formed was filtered off and washed with ethyl acetate (15 mL×3). The organic layer was separated and the remaining aqueous layer was extracted with ethyl acetate (15 mL×2). The combined organic extracts were washed with 1 M HCl (25 mL). The acidic aqueous extracts were washed with ethyl acetate (50 mL), then treated with aqueous sodium hydroxide (2 M) to pH 10-12, and extracted with ethyl acetate (40 mL×3). The combined organic extracts were washed with brine, dried (Na2SO4), and concentrated in vacuo to afford 1,2,3,4-tetrahydro-5,8-dimethoxynaphthalen-1-amine as an oil (4.68 g, 93% yield). $^1$H NMR (400 MHz, CDCl$_3$) δ 6.66 (s, 2H), 4.18 (br tr, 1H), 3.82 (s, 3H), 3.77 (s, 3H), 2.85-2.79 (m, 1H), 2.47-2.38 (m, 1H), 1.90-176 (m, 6H).

EXAMPLE 34

1,2,3,4-Tetrahydro-6-methoxy-N-(2-(methylsulfonyl)-5-(piperazin-1-yl)phenyl)naphthalen-1-amine

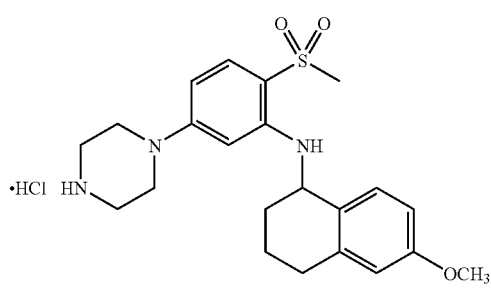

A solution of 1,2,3,4-tetrahydro-6-methoxynaphthalen-1-amine (1.0 mmol), 2,4-difluoro-1-(methylsulfonyl)benzene (1.0 mmol) and diisopropylethylamine (4.0 mmol) in N,N-dimethylformamide (2 mL) was stirred at 110° C. for 16 h. The reaction was cooled to room temperature, poured over water and extracted with diethyl ether. The solvent was concentrated in vacuo and the residue was used without further purification for the following reaction. N-(5-Fluoro-2-(methylsulfonyl)phenyl)-1,2,3,4-tetrahydro-6-methoxynaphthalen-1-amine (0.5 mmol), piperazine (8.0 mmol), N,N-diisopropylethylamine (4.0 mmol) were stirred at 80° C. in dry acetonitrile (3 mL) for 16 h. The solvent was evaporated and the residue was dissolved in dichloromethane and washed with water. The dichloromethane was evaporated and the crude compound was purified by silica chromatography using 10% methanol in dichloromethane to afford the title compound (21% yield). $^1$H NMR (400 MHz, CDCl$_3$): δ 7.61 (d, 1H), 7.21 (d, 1H), 6.72 (dd, 1H), 6.64 (d, 1H), 6.28 (dd, 1H), 6.23 (d, 1H), 4.62 (m, 1H), 3.79 (s, 3H), 3.28 (t, 4H), 3.00 (t, 4H), 2.93 (s, 3H), 2.81 (m, 2H), 1.94 (m, 4H); MS (ESI) m/z: 415.55 (M$^+$+1).

1,2,3,4-Tetrahydro-6-methoxynaphthalen-1-amine

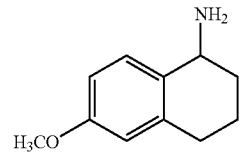

3,4-Dihydro-6,7-dimethoxynaphthalen-1(2H)-one (25.0 mmol), titanium(IV) isopropoxide (50.0 mmol) and 2 M solution of ammonia in ethanol (120 mmol) were stirred at room temperature for 6 h. The reaction was cooled to 0° C. and sodium borohydride was added portionwise during 10 min. (40.0 mmol); the resultant mixture was stirred at rt for an additional 3 h. The reaction was quenched by pouring it into ammonium hydroxide (2 M, 130 mL), the precipitate that formed was filtered off and washed with ethyl acetate (25 mL×3). The organic layer was separated and the remaining aqueous layer was extracted with ethyl acetate (25 mL×2). The combined organic extracts were washed with 1 M HCl (50 mL). The acidic aqueous extracts were washed with ethyl acetate (100 mL), then treated with aqueous sodium hydroxide (2 M) to pH 10-12, and extracted with ethyl acetate (75 mL×3). The combined organic extracts were washed with brine (75 mL), dried (Na$_2$SO$_4$), and concentrated in vacuo to afford the desired product (24% yield). $^1$H NMR (400 MHz, CDCl$_3$): δ 7.31 (d, 1H), 6.74 (dd, 1H), 6.60 (d, 1H), 3.94 (m, 1H), 3.78 (s, 3H), 2.75 (m, 2H), 2.01 (m, 2H), 1.72 (m, 2H).

EXAMPLE 35

6-Chloro-N-(2-(methylsulfonyl)-5-(piperazin-1-yl)phenyl)chroman-4-amine hydrochloride

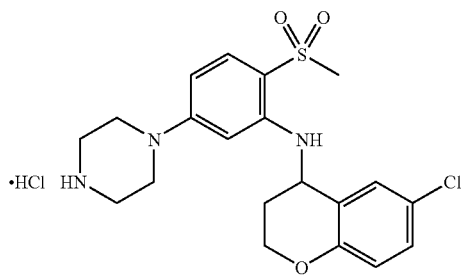

A solution of 6-chloro-N-(2-(methylsulfonyl)-5-(piperazin-1-yl)phenyl)chroman-4-amine (26.0 mg, 0.06 mmol) in anhydrous dichloromethane (5 mL) was cooled to 0° C. and HCl 37 μL of a 2M solution in diethyl ether, (0.07 mmol) were added. The mixture was allowed to stir for 30 min. After removal of solvent by rotary evaporation the desired product was collected (27.0 mg, 99%). $^1$H NMR (400 MHz, CD$_3$OD): δ 7.62 (d, 1H), 7.27 (d, 1H), 7.17 (dd, 1H), 6.83 (d, 1H), 6.51

(s, 1H), 6.48 (s, 1H), 4.89 (m, 1H), 4.25 (m, 2H), 3.59 (m, 4H), 3.34 (m, 4H), 2.98 (s, 3H), 2.16 (m, 2H); MS (ESI) m/z: 422.0 (M$^+$+1).

6-Chloro-N-(2-(methylsulfonyl)-5-(piperazin-1-yl) phenyl)chroman-4-amine

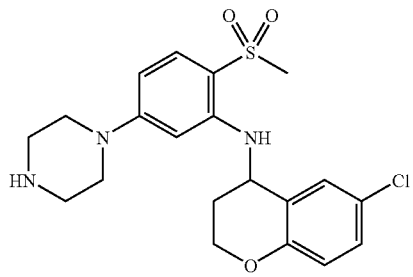

A solution of 6-chloro-N-(5-fluoro-2-(methylsulfonyl) phenyl)chroman-4-amine (143.0 mg, 0.4 mmol), piperazine (694.0 mg, 8.00 mmol) and N,N-diisopropylethylamine (0.52 mL, 4.00 mmol) in acetonitrile (5 mL) was stirred at reflux for 16 h. The reaction mixture was cooled down and concentrated under reduced pressure. The residue was taken up in dichloromethane, washed with water, dried and concentrated in vacuo. The crude product was purified by silica chromatography (5% methanol in dichloromethane) to yield 26.0 mg (15% yield) of desired product. $^1$H NMR (400 MHz, CD$_3$OD): δ 7.64 (d, 1H) 7.25 (d, 1H), 7.15 (dd, 1H), 6.81 (d, 1H), 6.45 (d, 1H), 6.35 (dd, 1H), 6.20 (d, 1H), 4.65 (m, 1H), 4.26 (m, 2H), 3.31 (m, 4H), 3.03 (m, 4H), 2.98 (s, 3H), 2.18 (m, 2H).

6-Chloro-N-(5-fluoro-2-(methylsulfonyl)phenyl) chroman-4-amine

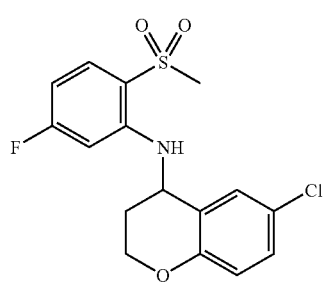

A solution of 6-chlorochroman-4-amine hydrochloride (551.0 mg, 2.50 mmol), 2,4-difluoro-1-(methylsulfonyl)benzene (496.0 mg, 2.50 mmol) and diisopropylethylamine (1.29 g, 10.0 mmol) in N,N-dimethylformamide (10 mL) was stirred at 110° C. for 16 h. The reaction was cooled to room temperature, poured over water and extracted with diethyl ether. The solvent was concentrated in vacuo and the residue was purified by silica chromatography (20% ethyl acetate in hexanes) to yield 143.0 mg (16%) of the desired product: $^1$H NMR (400 MHz, CDCl$_3$) δ 7.82 (dd, 1H), 7.19 (m, 2H), 6.83 (d, 1H), 6.57 (m, 2H), 4.60 (m, 1H), 4.30 (m, 1H), 4.28 (m, 1H), 3.01 (s, 3H), 2.19 (m, 2H).

EXAMPLE 36

N-(2-(Methylsulfonyl)-5-(piperazin-1-yl)phenyl) chroman-4-amine

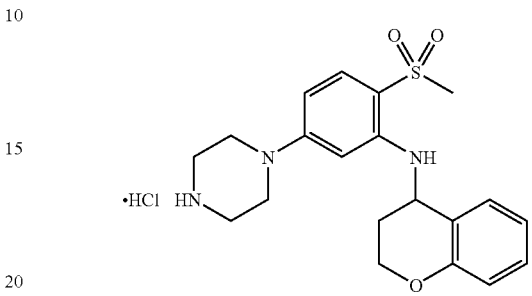

A solution of N-(5-fluoro-2-(methylsulfonyl)phenyl)chroman-4-amine (0.3 g, 0.93 mmol), piperazine (0.80 g, 9.33 mmol) and N,N-diisopropylethylamine (2.2 mL, 12.74 mmol) in acetonitrile (15 mL) was stirred at reflux for 16 h. The reaction mixture was cooled down and concentrated under reduced pressure. The residue was taken up in dichloromethane, washed with water, dried and concentrated in vacuo to yield 0.23 g of the crude aniline. The crude product was purified by PTLC (20% ethyl acetate in hexanes) to yield 144 mg (40%) of N-(2-(methylsulfonyl)-5-(piperazin-1-yl) phenyl)chroman-4-amine: $^1$H NMR (400 MHz, CD$_3$Cl): δ 7.63 (d, 1H), 7.31 (d, 1H), 7.28 (m, 1H), 6.91 (m, 1H), 6.85 (d, 1H), 6.47 (d, 1H), 6.42 (d, 1H), 6.21 (s, 1H), 4.80 (br s, 2H), 4.65 (m, 1H), 4.23 (m, 2H), 3.04 (m, 4H), 2.88 (s, 3H), 2.21 (m, 2H), 2.20 (br d, 1H). MS (ESI) m/z: Calculated: 387.16; Observed: 388.2 (M$^+$+1).

N-(5-Fluoro-2-(methylsulfonyl)phenyl)chroman-4-amine

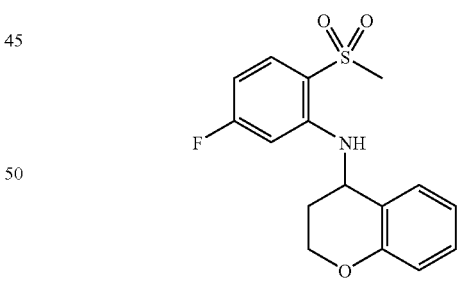

A solution of chroman-4-amine (0.38 g, 2.55 mmol), 2,4-difluoro-1-(methylsulfonyl)benzene (0.49 g, 2.55 mmol) and diisopropylethylamine (2.2 mL, 12.74 mmol) in N,N-dimethylformamide (10 mL) was stirred at 90° C. for 16 h. The reaction mixture was diluted with water and extracted with diethyl ether. The combined extracts were washed with water and brine, dried, and concentrated under reduced pressure to yield 0.48 g of a yellow oil. The residue was purified by PTLC (25% ethyl acetate in hexanes) to give 0.45 g (55%) of the desired aniline: $^1$H NMR (400 MHz, CDCl$_3$) δ 7.62 (dd, 1H), 7.35 (d, 1H), 7.28 (m, 1H), 6.91 (m, 1H), 6.85 (d, 1H), 6.57 (dd, 1H), 6.42 (dd, 1H), 4.49 (m, 1H), 4.34 (bs s, 1H), 4.29 (m, 2H), 2.86 (s, 3H), 2.23 (m, 2H). MS (ESI) m/z: Calculated: 321.08; Observed: 322.2 (M+ +1).

Chroman-4-amine

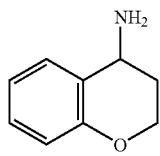

Chroman-4-one (3 g, 20.1 mmol), titanium(IV) isopropoxide (12.0 mL, 40.2 mmol) and 2 M solution of ammonia in ethanol (60.6 mL, 121.2 mmol) were stirred at room temperature for 6 h. The reaction was cooled to 0° C. and sodium borohydride was added portionwise during 10 min. (1.14 g, 30.2 mmol); the resultant mixture was stirred at rt for an additional 3 h. The reaction was quenched by pouring it into ammonium hydroxide (2 M, 60 mL), the precipitate that formed was filtered off and washed with ethyl acetate (15 mL×3). The organic layer was separated and the remaining aqueous layer was extracted with ethyl acetate (15 mL×2). The combined organic extracts were washed with 1 M HCl (25 mL). The acidic aqueous extracts were washed with ethyl acetate (50 mL), then treated with aqueous sodium hydroxide (2 M) to pH 10-12, and extracted with ethyl acetate (40 mL×3). The combined organic extracts were washed with brine, dried (Na$_2$SO$_4$), and concentrated in vacuo to afford Chroman-4-amine as an oil (2.61 g, 87% yield). $^1$H NMR (400 MHz, CDCl$_3$) δ 7.31 (d, 1H), 7.23 (m, 1H), 6.94 (m, 1H), 6.82 (d, 1H), 4.38 (m, 2H), 4.12 (m, 1H), 2.19 (m, 2H), 1.82 (m, 2H).

EXAMPLE 37

N-(1-(5-Chlorobenzo[d][1,3]dioxol-7-yl)ethyl)-2-(methylsulfonyl)-5-(piperazin-1-yl)benzenamine hydrochloride

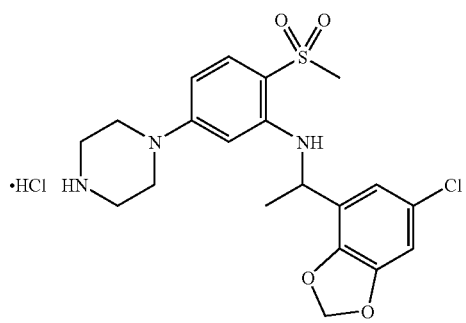

A solution of N-(1-(5-chlorobenzo[d][1,3]dioxol-7-yl)ethyl)-2-(methylsulfonyl)-5-(piperazin-1-yl)benzenamine (15.0 mg, 0.03 mmol) in anhydrous dichloromethane (0.5 mL) was cooled to 0° C. and HCl (34 μL of a 1M solution in diethyl ether, 0.03 mmol) were added. The mixture was allowed to stir for 30 min. The solvent was removed by rotary evaporation and co-evaporated with hexanes to precipitate the salt. After removal of solvent by rotary evaporation the desired product was collected (16 mg, 99%). $^1$H NMR (400 MHz, CD$_3$OD): δ 7.55 (d, 1H), 6.92 (d, 1H), 6.78 (d, 1H), 6.41 (dd, 1H), 6.06 (m 1H), 5.99 (s, 1H), 4.69 (m, 1H), 3.44 (m, 4H), 3.26 (m, 4H), 3.06 (s, 3H), 1.59 (d, 3H); MS (ESI) m/z: 438.2.0 (M+ +1).

N-(1-(5-Chlorobenzo[d][1,3]dioxol-7-yl)ethyl)-2-(methylsulfonyl)-5-(piperazin-1-yl)benzenamine

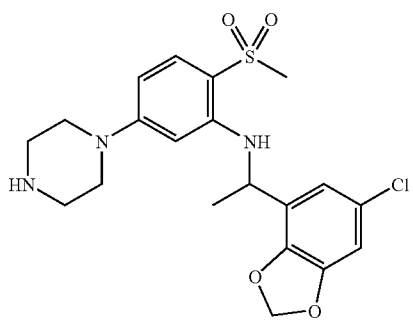

A solution of 1-(5-chlorobenzo[d][1,3]dioxol-7-yl)ethanamine (50.0 mg, 0.25 mmol), 2,4-difluoro-1-(methylsulfonyl)benzene (49.0 mg, 0.25 mmol) and diisopropylethylamine (129.0 mg, 4.0 mmol) in N,N-dimethylformamide (1 mL) was stirred at 110° C. for 16 h. The reaction was cooled to room temperature, poured over water and extracted with diethyl ether. The crude extract which contained mainly N-(1-(5-chlorobenzo[d][1,3]dioxol-7-yl)ethyl)-5-fluoro-2-(methylsulfonyl)benzenamine was used for the following reactions without further purification. A solution of N-(1-(5-chlorobenzo[d][1,3]dioxol-7-yl)ethyl)-5-fluoro-2-(methylsulfonyl)benzenamine (93.0 mg, 0.25 mmol), piperazine (432.0 mg, 5.0 mmol) and N,N-diisopropylethylamine (0.44 mL, 2.5 mmol) in acetonitrile (1 mL) was stirred at 80° C. for 16 h. The reaction mixture was cooled down and concentrated under reduced pressure. The residue was taken up in dichloromethane, washed with water, dried and concentrated in vacuo. The crude product was purified by silica chromatography (10% methanol in dichloromethane) to yield 15 mg (14%) of desired product. $^1$H NMR (400 MHz, CDCl$_3$): δ 7.56 (d, 1H), 6.80 (d, 1H), 6.72 (s, 1H), 6.51 (d, 1H), 6.26 (dd, 1H), 5.99 (dd, 2H), 5.92 (s, 1H), 4.59 (m, 1H), 3.21 (m, 4H), 2.57 (m, 4H), 1.59 (d, 3H); MS (ESI) m/z: 438.3 (M+ +1).

1-(5-Chlorobenzo[d][1,3]dioxol-7-yl)ethanamine

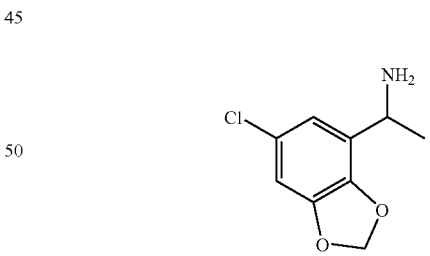

1-(5-Chlorobenzo[d][1,3]dioxol-7-yl)ethanone (90.0 mg, 0.45 mmol), titanium(IV) isopropoxide (255 mL, 0.90 mmol) and 2 M solution of ammonia in ethanol (1.10 mL, 2.26 mmol) were stirred at room temperature for 6 h. The reaction was cooled to 0° C. and sodium borohydride was added portionwise during 10 min. (25.5 mg, 0.67 mmol); the resultant mixture was stirred at rt for an additional 3 h. The reaction was quenched by pouring it into ammonium hydroxide (2 M, 10 mL), the precipitate that formed was filtered off and washed with ethyl acetate (5 mL×3). The organic layer was separated and the remaining aqueous layer was extracted with ethyl acetate (5 mL×2). The combined organic extracts were washed with 1 M HCl (5 mL). The acidic aqueous extracts were washed with ethyl acetate (15 mL), then treated with aqueous sodium hydroxide (2 M) to pH 10-12, and extracted with ethyl acetate (15 mL×3). The combined organic extracts were washed with brine (5 mL), dried (Na$_2$SO$_4$), and concentrated in vacuo to afford the desired product (50 mg, 56% yield).

1-(5-Chlorobenzo[d][1,3]dioxol-7-yl)ethanone

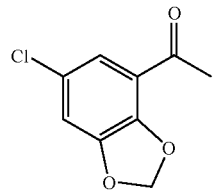

1-(5-Chlorobenzo[d][1,3]dioxol-7-yl)ethanol (155 mg, 0.77 mmol) was dissolved in 6 mL of dichloromethane. PCC (416 mg, 1.93 mmol) was added portionwise and the mixture was stirred for 16 h (reaction is likely to be completed earlier). The mixture was filtered through a plug of celite. The solvent was removed by rotary evaporation to collect the desired product (90 mg, 59% yield). $^1$H NMR (400 MHz, CDCl$_3$): δ 7.36 (d, 1H), 6.96 (d, 1H), 6.14 (s, 2H), 2.59 (s, 3H).

1-(5-Chlorobenzo[d][1,3]dioxol-7-yl)ethanol

6-Chlorobenzo[d][1,3]dioxole-4-carbaldehyde (147.0 mg, 0.79 mmol) was dissolved in 6 mL of diethyl ether and cooled to 0° C. MeMgBr (0.60 mL, 1.99 mmol) was added to the solution and the ice bath was removed. The reaction was allowed to stir at rt for 10 min. and at reflux for 30 min. The reaction was cooled to 0° C. and 10 mL of sat NH$_4$Cl were added to quench the reaction. The diethyl ether layer was separated and washed with water (10 mL×2). The organic layer was dried over Na$_2$SO$_4$ and the solvent was removed by rotary evaporation to collect the desired product (155.0 mg, 98%). $^1$H NMR (400 MHz, CDCl$_3$): δ 6.90 (d, 1H), 6.75 (d, 1H), 6.01 (d, 2H), 4.96 (m, 1H), 1.50 (d, 3H).

6-Chlorobenzo[d][1,3]dioxole-4-carbaldehyde

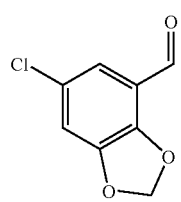

The title compound was prepared in 38% (0.15 g) yield from 5-chloro-2-hydroxy-3-methoxybenzaldehyde following the published procedure WO 2004110344, which is incorporated by reference herein in its entirety.

EXAMPLE 38

1,2,3,4-Tetrahydro-2-methyl-N-(2-(methylsulfonyl)-5-(piperazin-1-yl)phenyl)naphthalen-1-amine hydrochloride

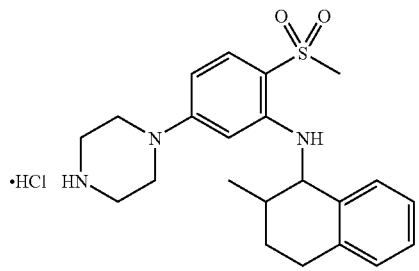

A solution of 1,2,3,4-tetrahydro-2-methyl-N-(2-(methylsulfonyl)-5-(piperazin-1-yl)phenyl)naphthalen-1-amine (70.0 mg, 0.18 mmol) in anhydrous dichloromethane (1.0 mL) was cooled to 0° C. and HCl (96 μL of a 1M solution in diethyl ether, 0.19 mmol) were added. The mixture was allowed to stir for 10 min. After removal of solvent by rotary evaporation the desired product was collected (82.0 mg, 100%). $^1$H NMR (400 MHz, CD$_3$OD): δ 7.58 (d, 1H), 7.25 (t, 1H), 7.15 (m, 3H), 6.41 (d, 1H), 6.27 (s, 1H), 4.45 (d, 1H), 3.47 (m, 4H), 3.36 (m, 1H), 3.30 (m, 4H), 2.98 (s, 3H), 2.30 (m, 1H), 2.08 (m, 2H), 1.72 (m, 1H), 1.13 (d, 3H); MS (ESI) m/z: 400.2 (M$^+$+1).

1,2,3,4-Tetrahydro-2-methyl-N-(2-(methylsulfonyl)-5-(piperazin-1-yl)phenyl)naphthalen-1-amine

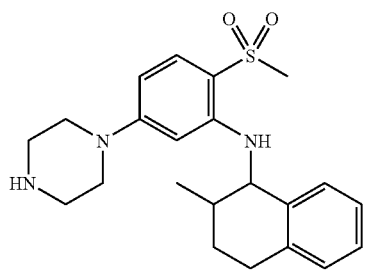

A solution of N-(5-fluoro-2-(methylsulfonyl)phenyl)-1,2,3,4-tetrahydro-2-methylnaphthalen-1-amine (63.3 mg, 0.19 mmol), piperazine (328 mg, 3.79 mmol) and N,N-diisopropylethylamine (0.34 mL, 1.99 mmol) in N,N-dimethylformamide (3 mL) was stirred at 110° C. for 16 h. The reaction mixture was cooled down, poured over 10 mL of water and extracted with diethyl ether. After evaporation of solvent the crude product was purified by silica chromatography (10% methanol in dichloromethane) to yield 70 mg (92%) of desired product. $^1$H NMR (400 MHz, CDCl$_3$): δ 7.61 (d, 1H), 7.29 (m, 1H), 7.14 (m, 3H), 6.46 (d, 1H), 6.27 (dd, 1H), 12.2 (d, 1H), 4.28 (t, 1H), 3.29 (m, 1H), 3.20 (m, 4H), 3.01 (m, 1H), 2.96 (m, 4H), 2.88 (s, 3H), 2.30-1.70 (m, 4H), 1.12 (d, 3H); MS (ESI) m/z: 400.1 (M$^+$+1).

N-(5-Fluoro-2-(methylsulfonyl)phenyl)-1,2,3,4-tetrahydro-2-methylnaphthalen-1-amine

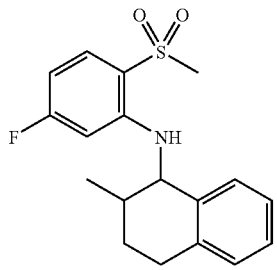

3,4-Dihydro-2-methylnaphthalen-1(2H)-one (5.2 g, 33.0 mmol), titanium(IV) isopropoxide (19.3 mL, 66.0 mmol) and 2 M solution of ammonia in ethanol (82.0 mL, 165 mmol) were stirred at room temperature for 6 h. The reaction was cooled to 0° C. and sodium borohydride was added portionwise during 10 min. (1.87 g, 49.5 mmol); the resultant mixture was stirred at rt for an additional 3 h. The reaction was quenched by pouring it into ammonium hydroxide (2 M, 20 mL), the precipitate that formed was filtered off and washed with ethyl acetate (20 mL×3). The organic layer was separated and the remaining aqueous layer was extracted with ethyl acetate (20 mL×2). The combined organic extracts were washed with 1 M HCl (15 mL). The acidic aqueous extracts were washed with ethyl acetate (30 mL), then treated with aqueous sodium hydroxide (2 M) to pH 10-12, and extracted with ethyl acetate (20 mL×3). The combined organic extracts were washed with brine (15 mL), dried (Na$_2$SO$_4$), and concentrated in vacuo to afford the desired product (1.20 g, 22.6% yield). The compound was used without further purification for the following reaction. A solution of 1,2,3,4-tetrahydro-2-methylnaphthalen-1-amine (63.0 mg, 0.39 mmol), 2,4-difluoro-1-(methylsulfonyl)benzene (85.0 mg, 0.43 mmol) and diisopropylethylamine (200 mg, 1.56 mmol) in N,N-dimethylformamide (1 mL) was stirred at 110° C. for 16 h. The reaction was cooled to room temperature, poured over water and extracted with diethyl ether. The solvent was concentrated in vacuo and the residue was purified by silica chromatography (10% ethyl acetate in hexanes) to give 65.0 mg (50%) of the desired product. $^1$H NMR (400 MHz, CDCl$_3$) δ 7.79 (dd, 1H), 7.20 (m, 4H), 6.52 (m, 3H), 4.25 (t, 1H), 2.99 (s, 3H), 2.86 (t, 1H), 2.65-1.65 (m, 4H), 1.16 (d, 3H); MS (ESI) m/z: 333.6 (M$^+$+1).

EXAMPLE 39

(1-(5-Fluoro-2-methoxy-3-chlorophenyl)ethyl)-2-(methylsulfonyl)-5-(piperazin-1-yl)benzenamine hydrochloride

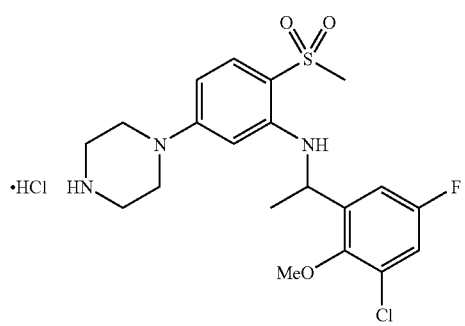

(1-(5-Fluoro-2-methoxy-3-chlorophenyl)ethyl)-2-(methylsulfonyl)-5-(piperazin-1-yl)benzenamine (70 mg, 0.15 mmol) was dissolved in dichloromethane (1.5 mL). The solution was cooled in a bath with dry ice and methanol. Hydrochloric acid (1.0 mL, 2.0 M in ether) was added slowly. The mixture was warmed to room temperature. The precipitate was filtered and washed with diethyl ether gave (1-(5-Fluoro-2-methoxy-3-chlorophenyl)ethyl)-2-(methylsulfonyl)-5-(piperazin-1-yl)benzenamine hydrochloride salt as a white solid (60 mg, 84%): $^1$H NMR (400 MHz, CD$_3$OD): δ 7.54 (d, 1H), 7.04 (m, 2H), 6.39 (d, 1H), 6.55 (s, 1H), 4.88 (m, 1H), 4.84 (bs, 3H), 3.88 (s, 3H), 3.41 (m, 4H), 3.21 (m, 4H), 1.59 (d, 3H). MS (ESI) m/z: Calculated: 441.13; Observed: 442.2 (M+H$^+$); (C$_{20}$H$_{25}$ClFN$_3$O$_3$S.HCl).

(1-(5-Fluoro-2-methoxy-3-chlorophenyl)ethyl)-2-(methylsulfonyl)-5-(piperazin-1-yl)benzenamine

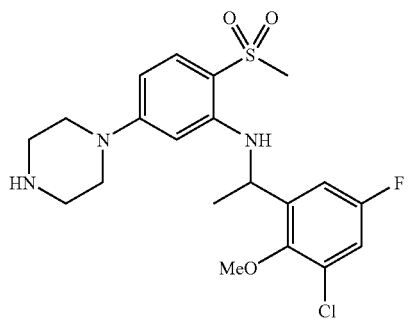

A solution of 5-Fluoro-N-(1-(5-fluoro-2-methoxy-3-chlorophenyl)ethyl)-2-(methylsulfonyl)benzenamine (0.15 g, 0.40 mmol), piperazine (0.1 g, 1.20 mmol) and N,N-diisopropylethylamine (0.21 mL, 1.20 mmol) in acetonitrile (10 mL) was stirred at 80° C. for 24 h. The reaction mixture was cooled down and concentrated under reduced pressure. The residue was taken up in dichloromethane, washed with water, dried and concentrated in vacuo to yield the crude residue which was purified by preparative TLC (3% methanol/dichloromethane) to (1-(5-Fluoro-2-methoxy-3-chlorophenyl)ethyl)-2-(methylsulfonyl)-5-(piperazin-1-yl)benzenamine (70 mg, 40%). $^1$H NMR (400 MHz, CDCl$_3$): δ 7.58 (d, 1H), 7.02 (dd, 1H), 6.95 (dd, 1H), 6.57 (d, 1H), 6.15 (dd, 1H), 5.84 (bs, 2H), 4.83 (m, 1H), 3.92 (s, 3H), 3.21-3.03 (m, 4H), 3.02 (s, 3H), 2.95 (m, 4H), 1.59 (d, 3H). MS (ESI) m/z: Calculated: 441.13; Observed: 442.2 (M+H$^+$); (C$_{20}$H$_{25}$ClFN$_3$O$_3$S).

5-Fluoro-N-(1-(5-fluoro-2-methoxy-3-chlorophenyl)ethyl)-2-(methylsulfonyl)benzenamine

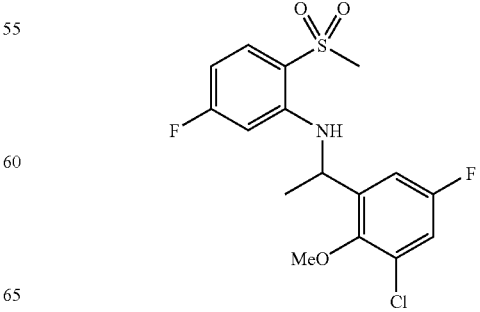

A solution of 1-(5-Fluoro-2-methoxy-3-chlorophenyl)ethanamine (0.38 g, 1.87 mmol), 2,4-difluoro-1-methanesulfonyl-benzene (0.3 g, 1.56 mmol) and N,N-diisopropylethylamine (1.4 mL, 7.81 mmol) in N,N-dimethylformamide (10 mL) was stirred at 110° C. for 18 h. Dichloromethane was added (20 mL) and washed with water (2×20), brine (20 mL), dried, and concentrated under reduced pressure to the crude compound which was purified by silica gel column (20% ethyl acetate in hexanes) to afford 5-fluoro-N-(1-(5-fluoro-2-methoxy-3-chlorophenyl)ethyl)-2-(methylsulfonyl)benzenamine (0.15 g, 26%): $^1$H NMR (400 MHz, CDCl$_3$): δ 7.76 (dd, 1H), 7.06 (dd, 1H), 6.84 (dd, 1H), 6.79 (bs, 1H), 6.42 (dd, 1H), 6.19 (dd, 1H), 4.82 (m, 1H), 3.97 (s 3H), 3.05 (s, 3H), 1.58 (d, 3H).

1-(5-Fluoro-2-methoxy-3-chlorophenyl)ethanamine

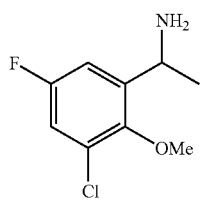

To a stirred solution of 1-(5-fluoro-2-methoxy-3-chlorophenyl)ethanone (1.9 g, 9.38 mmol), titanium(IV) isopropoxide (5.54 mL, 18.76 mmol) and ammonia in ethanol (23.5 mL) was stirred under nitrogen in a capped flask at ambient temperature for 6 h. Sodium borohydride (0.53 g, 14.07 mmol) was added and resulting mixture was stirred at room temperature for 3 h. The reaction was then quenched by pouring into ammonium hydroxide (40 mL), the resulting inorganic precipitate was filtered off, and washed with ethyl acetate (2×40 mL). the organic layer was separated and aqueous layer was extracted with ethyl acetate (2×40 mL). The combined organic layers were dried over Na$_2$SO$_4$, filtered, and evaporated to afford 1-(5-Fluoro-2-methoxy-3-chlorophenyl)ethanamine (1.7 g, 89%): $^1$H NMR (400 MHz, CDCl$_3$): δ 6.78 (dd, 1H), 6.68 (dd, 1H), 4.25 (m, 1H), 3.82 (s, 3H), 1.42 (d, 3H).

1-(5-Fluoro-2-methoxy-3-chlorophenyl)ethanone

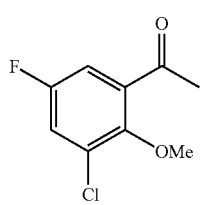

To a solution of 1-(5-Fluoro-2-methoxy-3-chlorophenyl)ethanol (2.1 g 10.1 mmol) in acetone (30 mL) at room temperature was added pyridinium chlorochromate (5.5 g, 26.2 mmol). The reaction was stirred for 3 hours, diethyl ether was added (50 mL). The resultant sludge was filtered through celite. The organic phase was dried over Na$_2$SO$_4$, filtered over silica gel, and concentrated to the crude compound which was purified by silica gel column (20% ethyl acetate in hexanes) to afford 1-(5-fluoro-2-methoxy-3-chlorophenyl)ethanone (1.9 g, 97%): $^1$H NMR (400 MHz, CDCl$_3$): δ 7.24 (m, 2H), 3.84 (s, 3H), 2.63 (s, 3H).

1-(5-Fluoro-2-methoxy-3-chlorophenyl)-ethanol

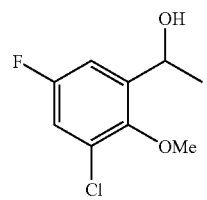

To a stirred solution of 5-Fluoro-2-methoxy-3-chlorobenzaldehyde (2.0 g, 11.0 mmol) in dry diethyl ether (40 mL) at 0° C. was added methylmagnesium bromide of 3.0 M in ether (8.8 mL, 27.12 mmol). The reaction mixture was brought to room temperature and was stirred for 30 min then refluxed for 3 hours. It was then cooled to 0° C. and quenched by adding saturated aqueous NH$_4$Cl. The two liquid layers were separated. The aqueous layer was extracted with ether. The combined organic layers were washed with water, dried, and concentrated to the crude compound which was purified by silica gel column (10-25% ethyl acetate in hexanes) to afford 1-(5-Fluoro-2-methoxy-3-chlorophenyl)ethanol (2.1 g, 98%): $^1$H NMR (400 MHz, CDCl$_3$): δ 7.12 (dd, 1H), 7.04 (dd, 1H), 5.19 (m, 1H), 3.84 (s, 3H), 2.18 (bs, 1H), 1.43 (d, 3H).

5-Fluoro-2-methoxy-3-chlorobenzaldehyde

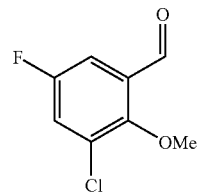

5-Fluoro-2-hydroxy-3-chlorobenzaldehyde (2.0 g, 11.01 mmol) was dissolved in N,N-dimethylformamide (30 mL) and to the solution was added methyl iodide (1.1 mL, 18.11 mmol) and potassium carbonate (4.4 g, 30.21 mmol). The mixture was stirred at 100° C. for one hour, cooled to room temperature and then diluted with water (40 mL). After extraction twice with ethyl acetate (40 mL) the combined organic layer was washed with brine and then dried over Na$_2$SO$_4$. The solvent was removed and the solid residue was treated with methanol. After filtration and drying desired compound was obtained 2.0 g (99%). $^1$H NMR (400 MHz, CDCl$_3$): δ 10.21 (s, 1H), 7.25 (dd, 1H), 7.12 (dd, 1H), 3.75 (s, 3H).

EXAMPLE 40

(1-(5-Fluoro-2-methoxy-3-methylphenyl)ethyl)-2-(methylsulfonyl)-5-(piperazin-1-yl)benzenamine hydrochloride

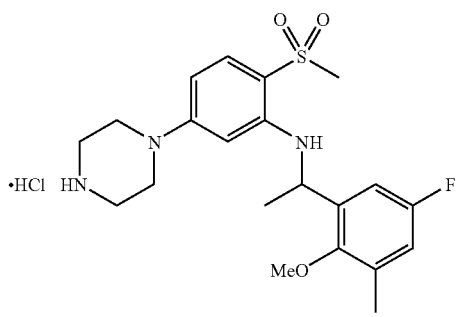

(1-(5-Fluoro-2-methoxy-3-methylphenyl)ethyl)-2-(methylsulfonyl)-5-(piperazin-1-yl)benzenamine (60 mg, 0.14 mmol) was dissolved in dichloromethane (1.5 mL). The solution was cooled in a bath with dry ice and methanol. Hydrochloric acid (1.0 mL, 2.0 M in ether) was added slowly. The mixture was warmed to room temperature. The precipitate was filtered and washed with diethyl ether gave (1-(5-Fluoro-2-methoxy-3-methylphenyl)ethyl)-2-(methylsulfonyl)-5-(piperazin-1-yl)benzenamine hydrochloride salt as a white solid (52 mg, 81%): $^1$H NMR (400 MHz, CD$_3$OD): $^1$H NMR (400 MHz, CD$_3$OD): δ 7.71 (d, 1H), 6.94 (dd, 1H), 6.85 (dd, 1H), 6.59 (d, 1H), 6.39 (dd, 1H), 4.95 (bs, 3H), 4.88 (m, 1H), 3.79 (s, 3H), 3.34-3.15 (m, 4H), 3.15 (s, 3H), 2.98 (m, 4H), 2.32 (s, 3H), 1.49 (d, 3H). MS (ESI) m/z: Calculated: 421.18; Observed: 422.2 (M+H$^+$); (C$_{21}$H$_{28}$FN$_3$O$_3$S.HCl).

(1-(5-Fluoro-2-methoxy-3-methylphenyl)ethyl)-2-(methylsulfonyl)-5-(piperazin-1-yl)benzenamine

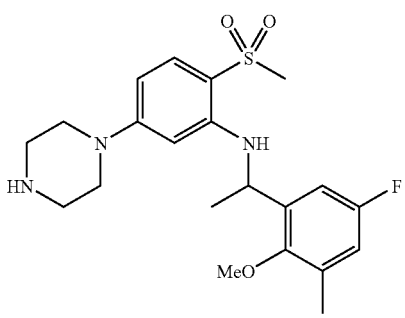

A solution of 5-fluoro-N-(1-(5-fluoro-2-methoxy-3-methylphenyl)ethyl)-2-(methylsulfonyl)benzenamine (0.083 g, 0.23 mmol), piperazine (0.1 g, 1.17 mmol) and N,N-diisopropylethylamine (0.20 mL, 1.17 mmol) in acetonitrile (10 mL) was stirred at 80° C. for 24 h. The reaction mixture was cooled down and concentrated under reduced pressure. The residue was taken up in dichloromethane, washed with water, dried and concentrated in vacuo to yield the crude residue which was purified by preparative TLC (3% methanol/dichloromethane) to (1-(5-Fluoro-2-methoxy-3-methylphenyl)ethyl)-2-(methylsulfonyl)-5-(piperazin-1-yl)benzenamine (60 mg, 91%). $^1$H NMR (400 MHz, CDCl$_3$): δ 7.52 (d, 1H), 6.84 (dd, 1H), 6.75 (dd, 1H), 6.49 (d, 1H), 6.19 (dd, 1H), 5.95 (bs, 2H), 4.85 (m, 1H), 3.78 (s, 3H), 3.24-3.05 (m, 4H), 3.15 (s, 3H), 2.88 (m, 4H), 2.32 (s, 3H), 1.39 (d, 3H). MS (ESI) m/z: Calculated: 421.18; Observed: 422.2 (M+H$^+$); (C$_{21}$H$_{28}$FN$_3$O$_3$S).

5-Fluoro-N-(1-(5-fluoro-2-methoxy-3-methylphenyl)ethyl)-2-(methylsulfonyl)benzenamine

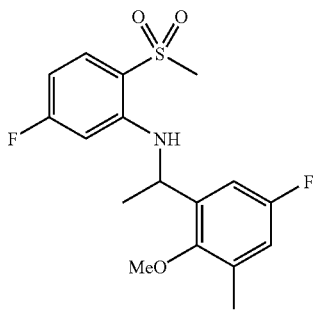

A solution of 1-(5-Fluoro-2-methoxy-3-methylphenyl)ethanamine (0.34 g, 1.87 mmol), 2,4-difluoro-1-methanesulfonyl-benzene (0.3 g, 1.56 mmol) and diisopropylethylamine (1.4 mL, 7.81 mmol) in N,N-dimethylformamide (10 mL) was stirred at 110° C. for 18 h. Dichloromethane was added (20 mL) and washed with water (2×20 mL), brine (20 mL), dried, and concentrated under reduced pressure to the crude compound which was purified by silica gel column (20% ethyl acetate in hexanes) to afford 5-fluoro-N-(1-(5-fluoro-2-methoxy-3-methylphenyl)ethyl)-2-(methylsulfonyl)benzenamine (83 mg, 14%): $^1$H NMR (400 MHz, CDCl$_3$): δ 7.78 (dd, 1H), 7.07 (dd, 1H), 7.03 (dd, 1H), 6.53 (dd, 1H), 6.32 (dd, 1H), 4.82 (bs, 1H), 4.45 (m, 1H), 3.75 (s, 3H), 3.07 (s, 3H), 2.41 (s, 3H), 1.48 (d, 3H).

1-(5-Fluoro-2-methoxy-3-methylphenyl)ethanamine

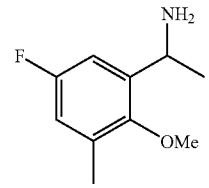

To a stirred solution of 1-(5-fluoro-2-methoxy-3-methylphenyl)ethanone (1.2 g, 6.59 mmol), titanium(IV) isopropoxide (3.89 mL, 13.17 mmol) and ammonia in ethanol (16.5 mL) was stirred under nitrogen in a capped flask at ambient temperature for 6 h. Sodium borohydride (0.37 g, 9.88 mmol) was added and resulting mixture was stirred at room temperature for 3 h. The reaction was then quenched by pouring into ammonium hydroxide (30 mL), the resulting inorganic precipitate was filtered off, and washed with ethyl acetate (2×25 mL). the organic layer was separated and aqueous layer was extracted with ethyl acetate (2×25 mL). The combined organic layers were dried over Na$_2$SO$_4$, filtered, and evaporated to afford 1-(5-Fluoro-2-methoxy-3-methylphenyl)ethanamine (1.0 g, 82%): $^1$H NMR (400 MHz, CDCl$_3$): δ 6.98 (dd, 1H), 6.78 (dd, 1H), 4.15 (m, 1H), 3.82 (s, 3H), 2.31 (s, 3H), 1.45 (d, 3H).

1-(5-Fluoro-2-methoxy-3-methylphenyl)ethanone

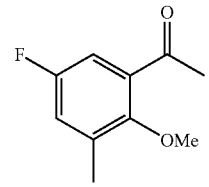

To a solution of 1-(5-Fluoro-2-methoxy-3-methylphenyl)ethanol (1.3 g 7.13 mmol) in acetone (15 mL) at room temperature was added pyridinium chlorochromate (3.8 g, 17.64 mmol). The reaction was stirred for 3 hours, diethyl ether was added (30 mL). The resultant sludge was filtered through celite. The organic phase was dried over Na$_2$SO$_4$, filtered over silica gel, and concentrated to the crude compound which was purified by silica gel column (20% ethyl acetate in hexanes) to afford 1-(5-fluoro-2-methoxy-3-methylphenyl)ethanone (1.2 g, 98%): $^1$H NMR (400 MHz, CDCl$_3$): δ 7.18 (dd, 1H), 7.05 (dd, 1H), 3.63 (s, 3H), 2.61 (s, 3H), 2.39 (s, 3H).

1-(5-Fluoro-2-methoxy-3-methylphenyl)-ethanol

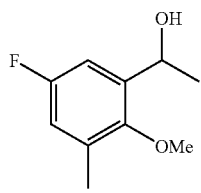

To a stirred solution of 5-Fluoro-2-methoxy-3-methylbenzaldehyde (1.2 g, 7.13 mmol) in dry diethyl ether (20 mL) at 0° C. was added methylmagnesium bromide of 3.0 M in ether (6.0 mL, 17.83 mmol). The reaction mixture was brought to room temperature and was stirred for 30 min then refluxed for 3 h. It was then cooled to 0° C. and quenched by adding saturated aqueous NH$_4$Cl. The two liquid layers were separated. The aqueous layer was extracted with ether. The combined organic layers were washed with water, dried, and concentrated to the crude compound which was purified by silica gel column (10-25% ethyl acetate in hexanes) to afford 1-(5-fluoro-2-methoxy-3-methylphenyl)ethanol (1.0 g, 76%): $^1$H NMR (400 MHz, CDCl$_3$): δ 7.12 (dd, 1H), 6.83 (dd, 1H), 4.72 (m, 1H), 3.81 (s, 3H), 2.38 (s, 3H), 1.47 (d, 3H).

5-Fluoro-2-methoxy-3-methylbenzaldehyde

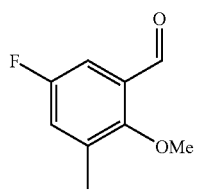

5-Fluoro-2-hydroxy-3-methylbenzaldehyde (1.24 g, 8.01 mmol) was dissolved in N,N-dimethylformamide (20 mL) and to the solution was added methyl iodide (0.8 mL, 12.71 mmol) and potassium carbonate (3.1 g, 22.52 mmol). The mixture was stirred at 100° C. for one hour, cooled to room temperature and then diluted with water (40 mL). After extraction twice with ethyl acetate (40 mL) the combined organic layer was washed with brine and then dried over Na$_2$SO$_4$. The solvent was removed and the solid residue was treated with methanol. After filtration and drying desired compound was obtained 1.2 g (99%). $^1$H NMR (400 MHz, CDCl$_3$): δ 0.12 (s, 1H), 7.23 (dd, 1H), 6.85 (dd, 1H), 3.75 (s, 3H), 2.32 (s, 3H).

EXAMPLE 41

N-(1-(5-Chloro-2,3-dimethoxyphenyl)ethyl)-5-(4-methylpiperazin-1-yl)-2-(methylsulfonyl)benzenamine hydrochloride

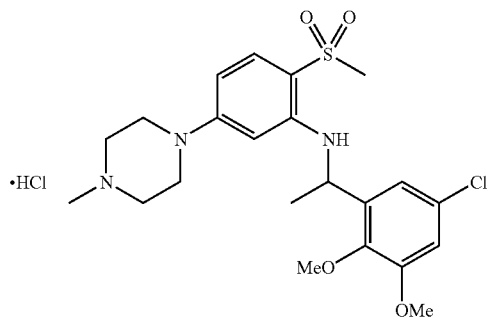

To a solution of N-(1-(5-chloro-2,3-dimethoxyphenyl)ethyl)-5-(4-methylpiperazin-1-yl)-2-(methylsulfonyl)benzenamine (45.1 mg, 0.10 mmol) in dichloromethane (2 mL) was added 0.06 mL (0.13 mmol) of 2 M HCl in diethyl ether. The solution was allowed to stir for 15 minutes and the solvent was removed by rotary evaporation. The residue was dissolved in dichloromethane and triturated with diethyl ether. The solvent was removed by rotary evaporation to collect the title compound (43.0 mg, 0.09 mmol) in 89.6% yield. $^1$H NMR (400 MHz, CD$_3$OD): δ 7.51 (d, 1H), 6.92 (m, 2H), 6.36 (d, 1H), 6.10 (s, 1H), 4.94 (m, 1H), 3.92 (m, 4H), 3.89 (s, 3H), 3.86 (s, 3H), 3.49 (m, 2H), 3.11 (m, 2H), 3.04 (s, 3H), 2.90 (s, 3H), 1.56 (d, 3H); MS (ESI) m/z: 468.0 (M$^+$+1).

N-(1-(5-Chloro-2,3-dimethoxyphenyl)ethyl)-5-(4-methylpiperazin-1-yl)-2-(methylsulfonyl)benzenamine

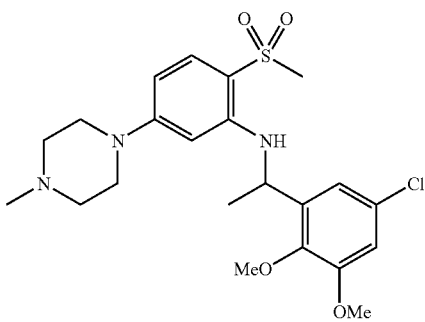

N-(1-(5-Chloro-2,3-dimethoxyphenyl)ethyl)-5-fluoro-2-(methylsulfonyl)benzenamine (0.50 g, 1.29 mmol), 1-methylpiperazine (0.60 g, 6.40 mmol), N,N-diisopropylethylamine (0.66 g, 5.15 mmol) were stirred at 110° C. in dry acetonitrile (3 mL) for 16 h. The solvent was evaporated and the residue was dissolved in dichloromethane and washed with water. The dichloromethane was evaporated and the crude compound was purified by silica chromatography using 10% methanol in dichloromethane to afford the title compound (45.1 mg, 7.5% yield). $^1$H NMR (400 MHz, CDCl$_3$): δ 7.54 (d, 1H), 6.87 (d, 1H), 6.76 (d, 1H), 6.52 (d, 1H), 6.22 (dd, 1H), 5.91 (d, 1H), 4.85 (m, 1H), 3.89 (s, 3H), 3.85 (s, 3H), 3.19 (m, 4H), 3.04 (s, 3H), 2.43 (m, 4H), 1.54 (d, 3H); MS (ESI) m/z: 468.0 (M$^+$).

EXAMPLE 42

1-(3-(1-(5-Chloro-2,3-dimethoxyphenyl)ethylamino)-4-(methylsulfonyl)phenyl)-N,N-dimethylpiperidin-4-amine hydrochloride

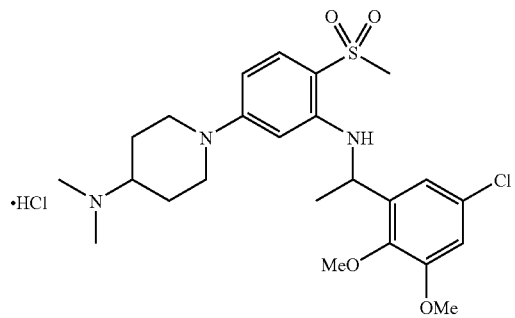

To a solution of 1-(3-(1-(5-chloro-2,3-dimethoxyphenyl)ethylamino)-4-(methylsulfonyl)phenyl)-N,N-dimethylpiperidin-4-amine (25.0 mg, 0.05 mmol) in dichloromethane (1 mL) was added 0.06 mL (0.06 mmol) of 1 M HCl in diethyl ether. The solution was allowed to stir for 15 minutes and the solvent was removed by rotary evaporation. The residue was dissolved in dichloromethane and triturated with diethyl ether. The solvent was removed by rotary evaporation to collect the title compound (26.0 mg, 0.05 mmol) in 97% yield. $^1$H NMR (400 MHz, CD$_3$OD): δ 7.49 (d, 1H), 6.93 (s, 1H), 6.91 (s, 1H), 6.37 (d, 1H), 6.08 (s, 1H), 3.93 (m, 2H), 3.90 (s, 3H), 3.86 (s, 3H), 3.45 (m, 1H), 3.04 (s, 3H), 2.92 (m, 2H), 2.82 (s, 6H), 2.04 (t, 2H), 1.66 (m, 2H), 1.55 (d, 3H), 1.49 (m, 2H); MS (ESI) m/z: 497.2 (M$^+$+1).

1-(3-(1-(5-Chloro-2,3-dimethoxyphenyl)ethylamino)-4-(methylsulfonyl)phenyl)-N,N-dimethylpiperidin-4-amine

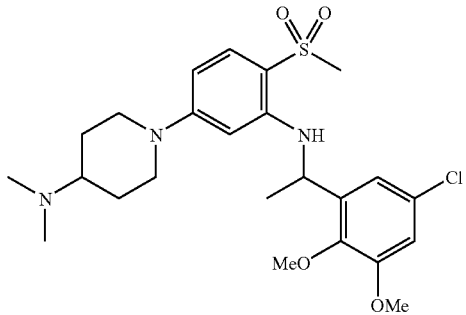

N-(1-(5-Chloro-2,3-dimethoxyphenyl)ethyl)-5-fluoro-2-(methylsulfonyl)benzenamine (100.0 mg, 0.26 mmol), N,N-dimethylpiperidin-4-amine (66.0 mg, 0.51 mmol), N,N-diisopropylethylamine (133.0 mg, 1.03 mmol) were stirred at 100° C. in dry acetonitrile (3 mL) for 16 h. The solvent was evaporated and the residue was dissolved in dichloromethane and washed with water. The dichloromethane was evaporated and the crude compound was purified by silica chromatography using 10% methanol in dichloromethane to afford the title compound (25.0 mg, 19.6% yield). $^1$H NMR (400 MHz, CDCl$_3$): δ 7.53 (d, 1H), 6.88 (d, 1H), 6.78 (d, 1H), 6.50 (d, 1H), 6.21 (d, 1H), 5.90 (d, 1H), 4.85 (m, 1H), 3.90 (s, 3H), 3.85 (s, 3H), 3.74 (m, 2H), 3.24 (m, 1H), 3.05 (s, 3H), 2.76 (q, 2H), 2.26 (s, 6H), 1.78 (t, 2H), 1.55 (d, 3H), 1.45 (m, 2H); MS (ESI) m/z: 496.1 (M$^+$).

EXAMPLE 43

(R)-1-(3-(1-(5-Chloro-2,3-dimethoxyphenyl)ethylamino)-4-(methylsulfonyl)phenyl)pyrrolidin-3-amine hydrochloride

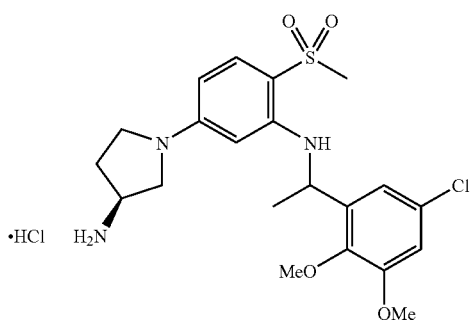

To a solution of (R)-1-(3-(1-(5-chloro-2,3-dimethoxyphenyl)ethylamino)-4-(methylsulfonyl)phenyl)pyrrolidin-3-amine (50.0 mg, 0.10 mmol) in dichloromethane (1 mL) was added 0.12 mL (0.12 mmol) of 1 M HCl in diethyl ether. The solution was allowed to stir for 15 minutes and the solvent was removed by rotary evaporation. The residue was dissolved in dichloromethane and triturated with diethyl ether. The solvent was removed by rotary evaporation to collect the title compound (50.0 mg, 0.10 mmol) in 93% yield. $^1$H NMR (400 MHz, CD$_3$OD): δ 7.48 (d, 1H), 6.91 (s, 1H), 6.88 (s, 1H), 6.03 (d, 1H), 5.66 (s, 1H), 3.99 (m, 1H), 3.91 (s, 3H), 3.85 (s, 3H), 3.62-3.21 (m, 4), 3.05 (s, 3H), 2.40 (m, 1H), 2.10 (m, 1H), 1.53 (d, 3H); MS (ESI) m/z: 455.1 (M$^+$+1).

(R)-1-(3-(1-(5-Chloro-2,3-dimethoxyphenyl)ethylamino)-4-(methylsulfonyl)phenyl)pyrrolidin-3-amine

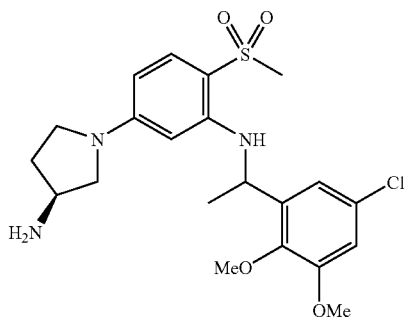

N-(1-(5-Chloro-2,3-dimethoxyphenyl)ethyl)-5-fluoro-2-(methylsulfonyl)benzenamine (100.0 mg, 0.26 mmol), pyrrolidin-3-amine (86.1 mg, 0.51 mmol), N,N-diisopropylethylamine (133.0 mg, 1.03 mmol) were stirred at 100° C. in dry acetonitrile (3 mL) for 16 h. The solvent was evaporated and the residue was dissolved in dichloromethane and washed with water. The dichloromethane was evaporated and the crude compound was purified by silica chromatography using 10% methanol in dichloromethane to afford the title compound (50.0 mg, 42.8% yield). $^1$H NMR (400 MHz, CDCl$_3$): δ 7.52 (d, 1H), 6.88 (d, 1H), 6.76 (d, 1H), 6.51 (d, 1H), 6.89 (dd, 1H), 4.84 (m, 1H), 3.89 (s, 3H), 3.84 (s, 3H), 3.64 (m, 1H), 3.46-2.84 (m, 4H), 3.04 (s, 3H), 2.12 (m, 1H), 2.01 (s, 3H), 1.75, (m, 1H), 1.53 (d, 3H); MS (ESI) m/z: 454.1 (M$^+$).

EXAMPLE 44

2-Nitro-(N-(1-phenylethyl)-5-(piperazin-1-yl))benzenamine hydrochloride

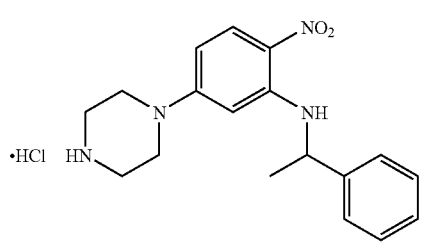

To a solution of t-butyl 4-(3-(1-phenylethylamino)-4-nitrophenyl)piperazine-1-carboxylate (0.1 mmol) in dry dichloromethane (1.0 mL) was added a saturated solution of HCl in diethyl ether (20 mL). The reaction mixture was stirred for 2 h. The solvent was removed by rotary evaporation to afford the title compound (68%). $^1$H NMR (400 MHz, CD$_3$OD): δ 7.63 (d, 1H), 7.36 (m, 5H), 6.36 (d, 1H), 5.86 (s, 1H), 4.75 (m, 1H), 3.52 (m, 2H), 3.45 (m, 2H), 3.17 (m, 4H), 1.60 (d, 3H); MS (ESI) m/z: Calculated: 377.4; Observed: 378.5 (M$^+$+1).

t-Butyl 4-(3-(1-phenylethylamino)-4-nitrophenyl)piperazine-1-carboxylate has the following formula

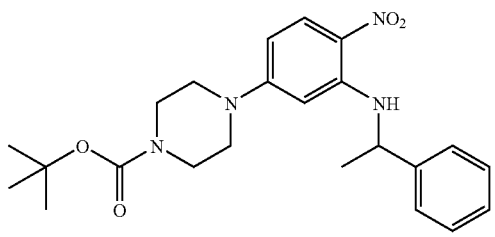

EXAMPLE 45

N-(3,5-Dichlorobenzyl)-2-nitro-5-(piperazin-1-yl)benzeneamine hydrochloride

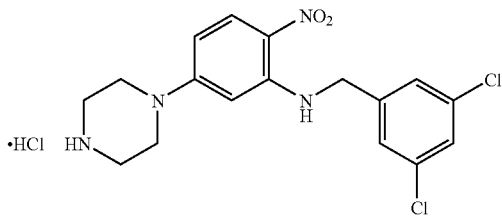

A mixture of tert-butyl 4-(3-(3,5-dichlorobenzylamino)-4-(2,2,2-trifluoroacetyl)phenyl)-piperazine-1-carboxylate (0.25 g, 0.5 mmol), trifluoroacetic acid (5 mL) and dichloromethane (10 mL) was stirred for 3 h and concentrated in vacuo. The residue was dissolved in dichloromethane; this solution was washed with aqueous NaHCO$_3$ solution, dried over Na$_2$SO$_4$ and concentrated in vacuo. The yellow solid residue was dissolved in dichloromethane (1 mL), reacted with 1 N HCl in diethyl ether (1 mL) and concentrated in vacuo to yield the title compounds as a yellow solid (76%). $^1$H NMR (400 MHz, CDCl$_3$): δ 9.37 (br, 1H), 7.62 (d, 1H), 7.28 (s, 1H), 7.22 (s, 2H), 6.24 (dd, 1H), 5.71 (d, 1H), 4.43 (d, 2H), 3.30 (m, 4H), 2.93 (m, 4H). MS (ESI) m/z: Calculated: 417.72; Observed: 381.26 (M+H$^+$ of free base).

t-Butyl 4-(3-(3,5-dichlorobenzylamino)-4-nitrophenyl-piperazine-1-carboxylate

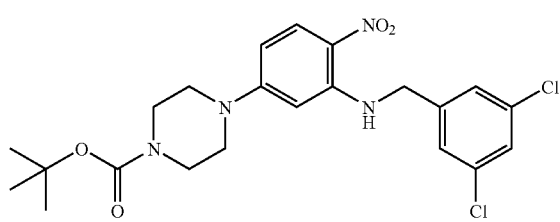

A mixture of 1-(2-(3,5-dichlorobenzylamino)-4-fluorophenyl)-nitrobenzene (2.1 mmol), t-butyl piperazine-1-carboxylate (2.2 mmol), N,N-diisopropylethylamine (4.4 mmol) and acetonitrile (10 mL) was heated at reflux for 18 h, cooled to room temperature and concentrated in vacuo. The residue was dissolved in ethyl acetate; this solution was washed with water, dried over Na$_2$SO$_4$ and concentrated in vacuo. The residue was purified by flash column chromatography on silica gel using 10% ethyl acetate in hexanes as eluent to yield the title compounds as a yellow solid (32%). $^1$H NMR (400 MHz, CDCl$_3$): δ 9.38 (br, 1H), 7.67 (d, 1H), 7.31 (s, 1H), 7.21 (s, 2H), 6.13 (dd, 1H), 5.70 (d, 1H), 4.42 (d, 2H), 3.54 (m, 4H), 3.38 (m, 4H), 1.49 (s, 9H). MS (ESI) m/z: Calculated: 481.37; Observed: 482.6 (M+H$^+$).

1-(2-(3,5-Dichlorobenzylamino)-4-fluoro-nitrobenzene

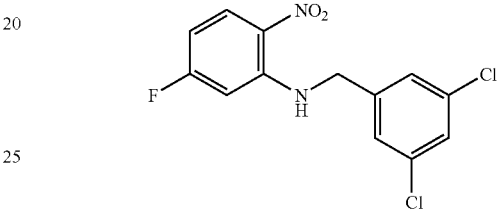

A mixture of 2,4-difluoronitrobenzene (5.0 mmol), 3,5-dichlorobenzylamine (5.0 mmol), N,N-diisopropylethylamine (10.0 mmol) and acetonitrile (25 mL) was heated at reflux for 18 h, cooled and concentrated in vacuo. The residue was dissolved in ethyl acetate; this solution was washed with water, dried over Na$_2$SO$_4$ and concentrated in vacuo. The residue was purified by flash column chromatography on silica gel using 5% ethyl acetate in hexanes as eluent to yield the title compound as a yellowish solid (46%). $^1$H NMR (400 MHz, CDCl$_3$): δ 9.28 (br s, 1H), 7.88 (m, 1H), 7.34 (s, 1H), 7.22 (s, 2H), 6.44 (m, 1H), 6.30 (dd, 1H), 4.43 (d, 2H).

EXAMPLE 46

2-Nitro-N-(1-phenyl)ethyl)-5-(piperazin-1-yl)benzenamine hydrochloride

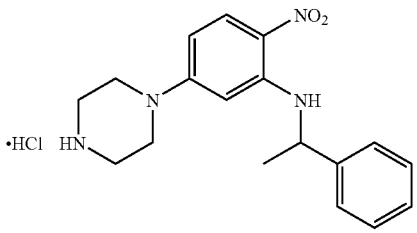

To a solution of 2-(nitro)-N-(1-phenyl)ethyl)-5-(piperazin-1-yl)benzenamine (0.04 mmol) in dichloromethane (1 mL) was added 10 mL of 1 M HCl in ether. The solution was allowed to stir for 1 h after which a precipitate formed. The solvent was removed by rotary evaporation to collect the title compound as off-white solid (89%). $^1$H NMR (400 MHz, CD$_3$OD): δ 8.10 (s, 1H), 7.55 (s, 1H), 7.30 (d, 1H), 7.21 (q, 1H), 7.02 (d, 1H), 6.39 (m, 1H), 4.66 (m, 1H), 3.92 (s, 3H), 3.40 (m, 4H), 3.26 (m, 4H), 1.53 (d, 3H); MS (ESI) m/z: Calculated for C$_{18}$H$_{22}$N$_4$O$_2$.HCl: 362.85; Observed: 327.4 (M$^+$+1 of its free base).

2-Nitro-N-(1-phenyl)ethyl)-5-(piperazin-1-yl)benzenamine

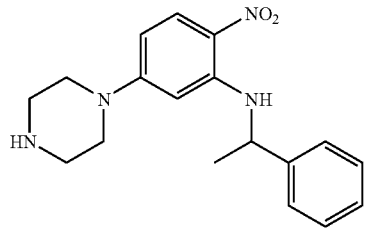

5-Fluoro-2-nitro-N-(1-(1-phenylethyl)-benzenamine (0.14 mmol), piperazine (0.42 mmol), N,N-diisopropylethylamine (0.28 mmol) were stirred at 80° C. in dry acetonitrile (5 mL) for 48 h. The solvent was evaporated and the residue was dissolved in dichloromethane and washed with water. The dichloromethane was evaporated and the crude compound was purified by silica chromatography using 15% methanol in dichloromethane to afford the title compound (31% yield). $^1$H NMR (400 MHz, CDCl$_3$): δ 7.55 (d, 1H), 7.16 (d, 1H), 6.81 (d, 1H), 6.58 (d, 1H), 6.22 (d, 1H), 5.83 (s, 1H), 5.30 (s, 1H), 4.85 (m, 1H), 3.87 (s, 3H), 3.11 (m, 4H), 2.91 (m, 4H), 1.51 (d, 3H); MS (ESI) m/z: Calculated for C$_{18}$H$_{22}$N$_4$O$_2$: 326.39; Observed: 327.4 (M$^{+1}$).

5-Fluoro-2-nitro-N-(1-(1-phenylethyl)-benzenamine

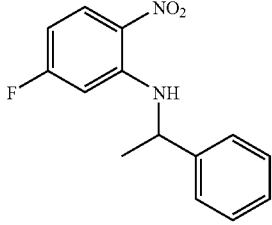

2,4-Difluoro-1-nitrobenzene (2.9 mmol), 1-phenylethyl amine (2.9 mmol) and N,N-diisopropylethylamine (5.9 mmol) were stirred at 65° C. in N,N-dimethylformamide (20 mL) for 24 h. The solvent was evaporated and the residue was dissolved in dichloromethane and washed with water. The dichloromethane was evaporated and purified by silica chromatography in 20% ethyl acetate in hexanes to collect the title compound (54% yield). $^1$H NMR (400 MHz, CDCl$_3$): δ 7.74 (q, 1H), 7.18 (m, 2H), 6.84 (d, 1H), 6.79 (d, 1H), 6.42 (t, 1H), 6.17 (d, 1H), 4.78 (m, 1H), 3.91 (s, 3H), 3.08 (s, 3H), 1.52 (d, 3H).

EXAMPLE 47

N-(1-(3,5-Dichlorophenyl)ethyl)-2-nitro 5-(piperazin-1-yl)-benzeneamine hydrochloride

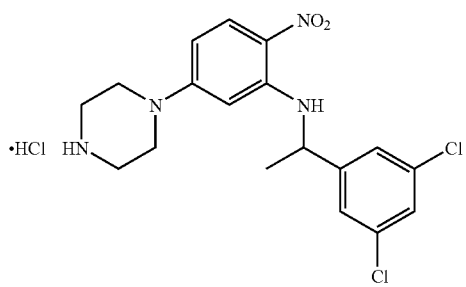

To a solution of N-(1-(3,5-dichlorophenyl)ethyl)-2-nitro-5-(piperazin-1-yl)benzeneamine (0.09 mmol) in dichloromethane (2.0 mL) was added a saturated solution of HCl in diethyl ether (15 mL). The reaction mixture was stirred for 2 h. The solvent was removed by rotary evaporation to afford the title compound in 39% yield. $^1$H NMR (400 MHz, CD$_3$OD): δ 7.67 (d, 1H), 7.37 (s, 2H), 7.35 (s, 1H), 6.41 (d, 1H), 5.84 (s, 1H), 4.79 (m, 1H), 3.57 (m, 4H), 3.25 (m, 4H), 1.61 (d, 3H); MS (ESI) m/z: Calculated for C$_{18}$H$_{20}$Cl$_2$N$_4$O$_2$.HCl: 431.74; Observed: 396.4 (M$^+$+1 corresponding to its free base).

N-(1-(3,5-Dichlorophenyl)ethyl)-2-nitro-5-(piperazin-1-yl)benzeneamine

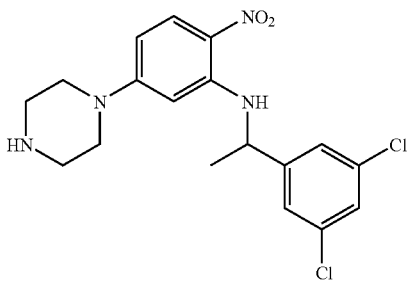

N-(1-(3,5-dichlorophenyl)ethyl)-5-fluoro-2-nitrobenzenamine (1.62 mmol), piperazine (8.1 mmol), N,N-diisopropylethylamine (0.58 mmol) were stirred at 60° C. in dry acetonitrile (20 mL) for 3 days. The solvent was evaporated and the residue was dissolved in dichloromethane and washed with water. The dichloromethane was evaporated and the crude compound was purified by silica chromatography using 20% ethyl acetate in hexanes to afford the title compound (19% yield). $^1$H NMR (400 MHz, CDCl$_3$): δ 9.31 (d, 1H), 7.63 (d, 1H), 7.25 (s, 1H), 7.22 (s, 2H), 6.18 (d, 1H), 5.53 (s, 1H), 4.48 (m, 1H), 3.48 (m, 4H), 3.25 (m, 4H), 1.60 (d, 3H), 1.47 (s, 9H); MS (ESI) m/z: Calculated for C$_{18}$H$_{20}$O$_2$N$_4$O$_2$: 395.28; Observed: 396.3 (M$^+$+1).

N-(1-(3,5-dichlorophenyl)ethyl)-5-fluoro-2-nitrobenzenamine

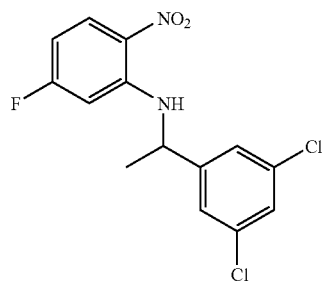

A mixture of 2,4-difluoro-nitrobenzene (3.13 mmol), 1-(3,5-dichlorophenyl)ethanamine (3.13 mmol) and N,N-diisopropylethylamine (6.3 mmol) were stirred at 45° C. in dry acetonitrile (25 mL) for 16 h. The solvent was evaporated and the residue was dissolved in dichloromethane and washed with water. The dichloromethane was evaporated and purified by silica chromatography in 20% ethyl acetate in hexanes to collect the title compound (11% yield). ¹H NMR (400 MHz, CDCl₃): δ 9.23 (s, 1H), 7.87 (t, 1H), 7.28 (s, 1H), 7.19 (s, 2H), 6.41 (t, 1H), 6.11 (d, 1H), 4.51 (m, 1H), 1.62 (d, 3H).

EXAMPLE 48

N-(3,5-Dichlorobenzyl)-2-(methylsulfonyl)-5-(piperazin-1-yl)benzenamine hydrochloride

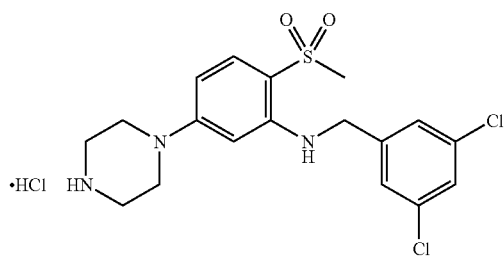

A mixture of tert-butyl 4-(3-(3,5-dichlorobenzylamino)-4-(methylsulfonyl)phenyl)-piperazine-1-carboxylate (0.5 mmol), trifluoroacetic acid (5 mL) and dichloromethane (10 mL) was stirred for 3 h and concentrated in vacuo. The residue was dissolved in dichloromethane; this solution was washed with aqueous NaHCO₃ solution, dried over Na₂SO₄ and concentrated in vacuo. The yellow solid residue was dissolved in dichloromethane (1 mL), reacted with 1 N HCl in ether (1 mL) and concentrated in vacuo to yield the title compound as a yellow solid (59%). ¹H NMR (400 MHz, CDCl₃): δ 9.37 (br, 1H), 7.62 (d, 1H), 7.28 (s, 1H), 7.22 (s, 2H), 6.24 (dd, 1H), 5.71 (d, 1H), 4.43 (d, 2H), 3.30 (m, 4H), 2.93 (m, 4H). MS (ESI) m/z: Calculated: 450.81; Observed: 415.4 (M+H⁺ corresponding to its free base).

t-Butyl 4-(3-(3,5-dichlorobenzylamino)-4-(methylsulfonyl)phenyl)piperazine-1-carboxylate

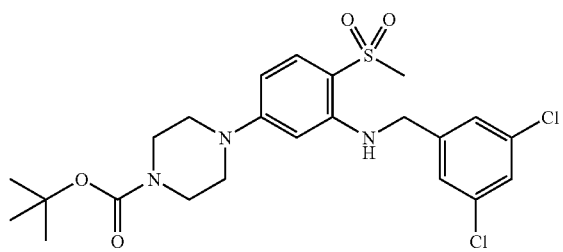

A mixture of N-(3,5-dichlorobenzyl)-5-fluoro-2-(methylsulfonyl)benzenamine (2.1 mmol), t-butyl piperazine-1-carboxylate (2.2 mmol), N,N-diisopropylethylamine (4.4 mmol) and acetonitrile (10 mL) was heated at reflux for 18 h, cooled to room temperature and concentrated in vacuo. The residue was dissolved in ethyl acetate; this solution was washed with water, dried over Na₂SO₄ and concentrated in vacuo. The residue was purified by flash column chromatography on silica gel using 10% ethyl acetate in hexanes as eluent to yield the title compounds as a yellow solid (23%). ¹H NMR (400 MHz, CDCl₃): δ 9.38 (br, 1H), 7.67 (d, 1 H), 7.31 (s, 1H), 7.21 (s, 2H), 6.13 (dd, 1H), 5.70 (d, 1H), 4.42 (d, 2H), 3.54 (m, 4H), 3.38 (m, 4H), 1.49 (s, 9H). MS (ESI) m/z: Calculated: 514.47; Observed: 515.6 (M+1).

N-(3,5-Dichlorobenzyl)-5-fluoro-2-(methylsulfonyl)benzenamine

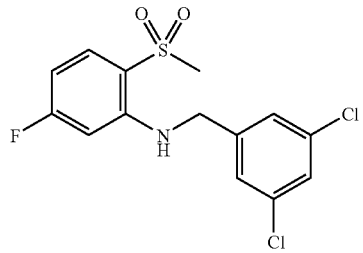

A mixture of 2,4-difluoromethylsulfonylbenzene (5.0 mmol), 3,5-dichlorobenzylamine (5.0 mmol), N,N-diisopropylethylamine (10.0 mmol) and acetonitrile (25 mL) was heated at reflux for 18 h, cooled and concentrated in vacuo. The residue was dissolved in ethyl acetate; this solution was washed with water, dried over Na₂SO₄ and concentrated in vacuo. The residue was purified by flash column chromatography on silica gel using 5% ethyl acetate in hexanes as eluent to yield the title compounds as a yellowish solid (37%). ¹H NMR (400 MHz, CDCl₃): δ 9.28 (br s, 1H), 7.88 (m, 1H), 7.34 (s, 1H), 7.22 (s, 2H), 6.44 (m, 1H), 6.30 (dd, 1H), 4.43 (d, 2H).

EXAMPLE 49

N-3,5-Dichlorobenzyl)-4-nitro-3-(piperazin-1-yl)benzenamine hydrochloride

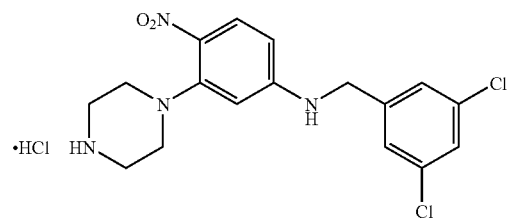

To a solution of N-(3,5-dichlorobenzyl)-4-nitro-3-(piperazin-1-yl)benzenamine (0.17 mmol) in dry dichloromethane (1.0 mL) was added a saturated solution of HCl in diethyl ether (15 mL). The reaction mixture was stirred for 4 h. The solvent was evaporated and the precipitate was recrystallized from methanol (0.3 mL), dichloromethane (0.5 mL) and diethyl ether (5 mL). The product was collected by filtration and dried under vacuum to afford the title compound (61%). ¹H NMR (400 MHz, CDCl₃): δ 9.37 (br, 1H), 7.62 (d, 1H), 7.28 (s, 1H), 7.22 (s, 2H), 6.24 (dd, 1H), 5.71 (d, 1H), 4.43 (d, 2H), 3.30 (m, 4H), 2.93 (m, 4H). MS (ESI) m/z: Calculated: 417.72; Observed: 382.4 (M+H⁺ of free base).

t-Butyl 4-(5-(3,5-dichlorobenzylamino)-2-nitrophenyl)piperazine-1-carboxylate

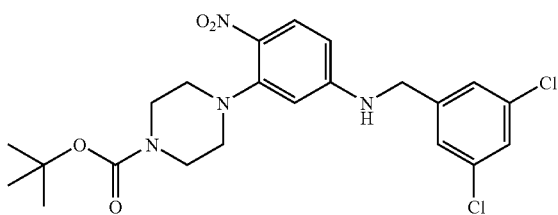

t-Butyl 4-(5-fluoro-2-nitrophenyl)piperazine-1-carboxylate (1.3 mmol), 3,5-dichlorobenzylamine (1.3 mmol), N,N-diisopropylethylamine (1.3 mmol) were stirred at 80° C. in dry acetonitrile (25 mL) for 72 h. The solvent was evaporated and the residue was dissolved in dichloromethane and washed with water. The dichloromethane was evaporated and the crude compound was purified by silica chromatography using 25% ethyl acetate in hexanes to afford the title compound (41%). $^1$H NMR (400 MHz, CDCl$_3$): δ 9.38 (br, 1H), 7.67 (d, 1H), 7.31 (s, 1H), 7.21 (s, 2H), 6.13 (dd, 1H), 5.70 (d, 1H), 4.42 (d, 2H), 3.54 (m, 4H), 3.38 (m, 4H), 1.49 (s, 9 H). MS (ESI) m/z: Calculated: 481.37; Observed: 482.6 (M+H$^+$).

t-Butyl 4-(5-fluoro-2-nitrophenyl)piperazine-1-carboxylate

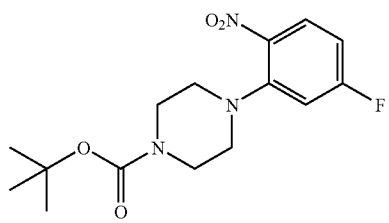

2,4-Difluoronitrobenzene (10.0 g, 62.9 mmol), t-butyl piperazine-1-carboxylate (11.7 g, 62.9 mmol) and N,N-diisopropylethylamine (8.10 g, 62.9 mmol) were stirred at room temperature in dry acetonitrile (100 mL) for 16 h. The solvent was removed by rotary evaporation and the residue was dissolved in dichloromethane and washed with water. The dichloromethane was removed by rotary evaporation to collect the title compound (19.0 g, 93%). $^1$H NMR (400 MHz, CDCl$_3$): δ 7.91 (dd, 1H), 6.75 (m, 2H), 3.60 (m, 4H), 3.03 (m, 4H), 1.48 (s, 9H); MS (ESI) m/z: Calculated for C$_{15}$H$_{20}$FN$_3$O$_4$Na: 348.13; Observed: 348.1 (M$^+$+Na).

EXAMPLE 50

N-(1-(3,5-Dichlorophenyl)ethyl-4-nitro-3-(piperazin-1-yl)benzenamine hydrochloride

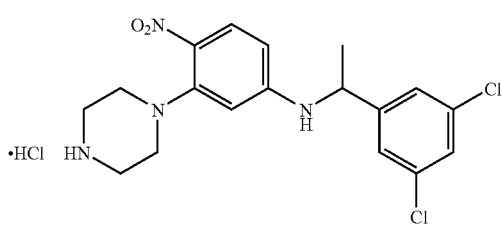

Characterization data for the title compound is: $^1$H NMR (400 MHz, CD$_3$OD): δ 7.67 (d, 1H), 7.37 (s, 2H), 7.35 (s, 1H), 6.41 (d, 1H), 5.84 (s, 1H), 4.79 (m, 1H), 3.57 (m, 4H), 3.25 (m, 4H), 1.61 (d, 3H); MS (ESI) m/z: Calculated for C$_{18}$H$_{20}$Cl$_2$N$_4$O$_2$.HCl: 431.74; Observed: 396.4 (M$^+$+1 corresponding to its free base).

t-Butyl 4-(5-(1-(3,5-dichlorophenyl)ethylamino-2-nitrophenyl)piperazine-1-carboxylate

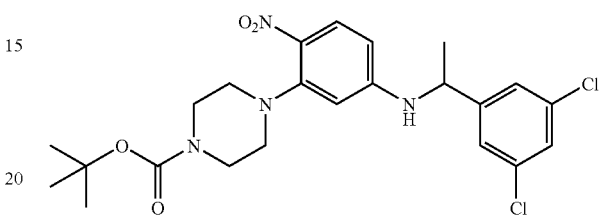

t-Butyl 4-(5-fluoro-2-nitrophenyl)piperazine-1-carboxylate (1.3 mmol), 1-(3,5-dichlorophenyl)ethanamine (1.3 mmol), N,N-diisopropylethylamine (1.3 mmol) were stirred at 80° C. in dry acetonitrile (25 mL) for 72 h. The solvent was evaporated and the residue was dissolved in dichloromethane and washed with water. The dichloromethane was evaporated and the crude compound was purified by silica chromatography using 25% ethyl acetate in hexanes to afford the title compound (41% yield). $^1$H NMR (400 MHz, CDCl$_3$): δ 9.31 (d, 1H), 7.63 (d, 1H), 7.25 (s, 1H), 7.22 (s, 2H), 6.18 (d, 1H), 5.53 (s, 1H), 4.48 (m, 1H), 3.48 (m, 4H), 3.25 (m, 4H), 1.60 (d, 3H), 1.47 (s, 9H); MS (ESI) m/z: Calculated: 495.4; Observed: 496.3 (M$^+$+1).

EXAMPLE 51

5-(1,4-Diazepan-1-yl)-2-nitro-N-(1-phenylethyl)benzenamine hydrochloride

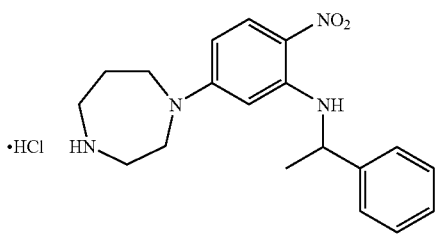

To a solution of t-butyl 4-(3-(1-phenylethylamino)-4-nitrophenyl)-1,4-diazepane-1-carboxylate (0.1 mmol) in dry dichloromethane (1.0 mL) was added a saturated solution of HCl in diethyl ether (20 mL). The reaction mixture was stirred for 2 h. The solvent was removed by rotary evaporation to afford the title compound (68%). $^1$H NMR (400 MHz, CD$_3$OD): δ 7.99 (d, 1H), 7.52 (m, 5H), 6.36 (d, 1H), 5.86 (s, 1H), 4.75 (m, 1H), 3.52 (m, 2H), 3.45 (m, 2H), 3.17 (m, 4H), 1.81 (m, 2H), 1.60 (d, 3H); MS (ESI) m/z: Calculated: 376.8; Observed: 341.5 (M$^+$+1).

t-Butyl 4-(3-(1-phenylethylamino)-4-nitrophenyl)-1,4-diazepane-1-carboxylate

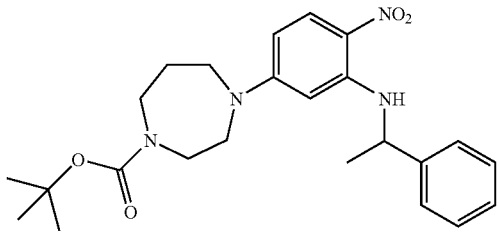

1-(2-(1-Phenylethylamino)-4-fluorophenyl)-4-nitrobenzene (0.5 mmol), t-butyl 1,4-diazepane-1-carboxylate (0.55 mmol), N,N-diisopropylethylamine (1.0 mmol) were stirred at 80° C. in dry acetonitrile (25 mL) for 21 h. The solvent was evaporated and the residue was dissolved in dichloromethane and washed with water. The dichloromethane was evaporated and the crude compound was purified by silica chromatography using 25% ethyl acetate in hexanes to afford the title compound (18% yield). $^1$H NMR (400 MHz, CDCl$_3$): δ 9.36 (d, 1H), 7.82 (d, 1H), 7.32 (m, 4H), 7.24 (m, 1H), 6.13 (d, 1H), 5.61 (s, 1H), 4.55 (m, 1H), 3.39 (m, 4H), 3.25 (m, 2H), 3.14 (m, 2H), 1.79 (m, 2H), 1.61 (d, 3H), 1.46 (s, 9H); MS (ESI) m/z: Calculated: 441.2; Observed: 442.3 (M+1).

EXAMPLE 52

N-(1-(6-Chloro-2,3-dihydrobenzo[b][1,4]dioxin-8-yl)ethyl)-2-(methylsulfonyl)-5-(N,N-dimethylpiperidin)-benzenamine hydrochloride

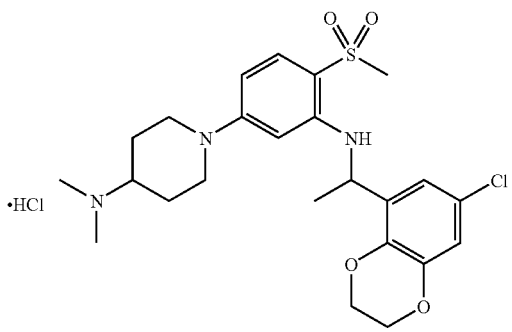

A solution of N-(1-(6-chloro-2,3-dihydrobenzo[b][1,4]dioxin-8-yl)ethyl)-2-(methylsulfonyl)-5-(N,N-dimethylpiperidin)-benzenamine (0.025 mmol) in anhydrous dichloromethane (1 mL) was cooled to 0° C. and HCl (0.12 mL of a 1 M solution in diethyl ether, 0.12 mmol) was added. The mixture was allowed to stir for 30 min. The solvent was removed by rotary evaporation, more diethyl ether was added to precipitate the salt. After removal of solvent by rotary evaporation the desired product was collected (82%). $^1$H NMR (400 MHz, CD$_3$OD): δ 7.68 (d, 1H), 6.96 (d, 1H), 6.81 (d, 1H), 6.60 (dd, 1H), 6.11 (d, 1H), 4.93 (m, 1H), 4.38 (m, 2H), 4.36 (m, 2H), 3.89 (m, 4H), 2.98 (s, 3H), 2.82 (m, 1H), 2.77 (s, 6H), 1.68 (m, 4H), 1.54 (d, 3H); MS (ESI) m/z: 495.0 (M$^+$+1).

N-(1-(6-Chloro-2,3-dihydrobenzo[b][1,4]dioxin-8-yl)ethyl)-2-(methylsulfonyl)-5-(N,N-dimethylpiperidin)-benzenamine

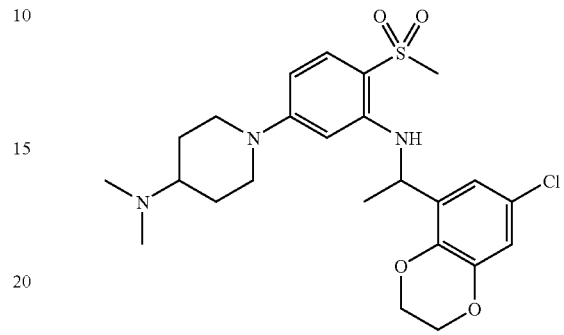

A solution of 1-(6-chloro-2,3-dihydrobenzo[b][1,4]dioxin-8-yl)ethanamine (130 mg, 0.61 mmol), 2,4-difluoro-1-(methylsulfonyl)benzene (116 mg, 0.61 mmol) and N,N-diisopropylethylamine (314 mg, 2.43 mmol) in N,N-dimethylformamide (2 mL) was stirred at 110° C. for 16 h. The reaction was cooled to room temperature, poured over water and extracted with diethyl ether. The solvent was concentrated under vacuo to collect 53.4 mg of the desired product, which was used for the next reaction without further purification. A solution of N-(1-(6-chloro-2,3-dihydrobenzo[b][1,4]dioxin-8-yl)ethyl)-5-fluoro-2-(methylsulfonyl)benzenamine (0.1 mmol), 4-N,N-dimethylaminopiperazine (3.0 mmol) and N,N-diisopropylethylamine (1.4 mmol) in acetonitrile (2 mL) was stirred at reflux for 16 h. The reaction mixture was cooled down and concentrated under reduced pressure. The residue was taken up in dichloromethane, washed with water, dried and concentrated under vacuo. The crude product was purified by silica chromatography (10% ethyl acetate in hexanes) to afford the desired product (12%). $^1$H NMR (400 MHz, CDCl$_3$): δ 7.52 (d, 1H), 6.87 (d, 1H), 6.76 (d, 1H), 6.54 (dd, 1H), 6.07 (d, 1H), 4.78 (m, 1H), 4.29 (m, 2H), 4.22 (m, 2H), 3.75 (m, 4H), 2.85 (s, 3H), 2.79 (m, 1H), 2.64 (s, 6H), 1.70 (m, 4H), 1.61 (d, 3H); MS (ESI) m/z: 495.1 (M$^+$+1).

EXAMPLE 53

N$^3$-(1-(6-Chloro-2,3-dihydrobenzo[b][1,4]dioxin-8-yl)ethyl)-N$^1$-(2-dimethylamino)ethyl)-N$^1$-methyl-4-(methylsulfonyl)-benzene-1,3-diamine hydrochloride

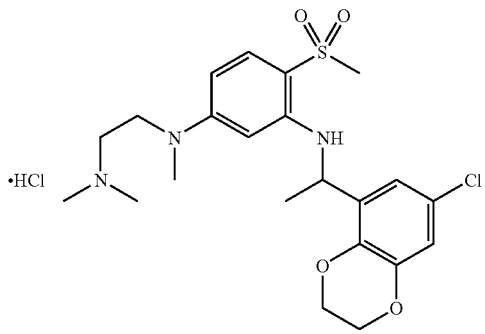

A solution of N³-(1-(6-Chloro-2,3-dihydrobenzo[b][1,4]dioxin-8-yl)ethyl)-N¹-(2-dimethylamino)ethyl)-N¹-methyl-4-(methylsulfonyl)-benzene-1,3-diamine (0.025 mmol) in anhydrous dichloromethane (1 mL) was cooled to 0° C. and HCl (0.12 mL of a 1 M solution in diethyl ether, 0.12 mmol) was added. The mixture was allowed to stir for 30 min. The solvent was removed under reduced pressure to give the desired product (75%). ¹H NMR (400 MHz, CD₃OD): δ 7.78 (d, 1H), 7.01 (d, 1H), 6.89 (d, 1H), 6.64 (dd, 1H), 6.15 (d, 1H), 4.98 (m, 1H), 4.42 (m, 4H), 3.61 (t, 2H), 2.93 (s, 3H), 2.80 (s, 3H), 2.68 (t, 2H), 2.61 (s, 6H), 1.60 (d, 3H); MS (ESI) m/z: 469.0 (M⁺+1).

N³-(1-(6-Chloro-2,3-dihydrobenzo[b][1,4]dioxin-8-yl)ethyl)-N¹-(2-dimethylamino)ethyl)-N¹-methyl-4-(methylsulfonyl)-benzene-1,3-diamine

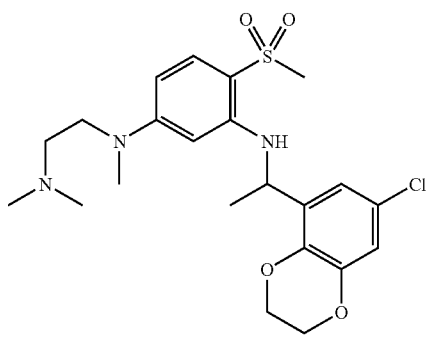

A solution of N-(1-(6-chloro-2,3-dihydrobenzo[b][1,4]dioxin-8-yl)ethyl)-5-fluoro-2-(methylsulfonyl)benzenamine (0.1 mmol), N¹,N¹,N²-trimethylethane-1,2-diamino (3.0 mmol) and N,N-diisopropylethylamine (1.4 mmol) in acetonitrile (2 mL) was stirred at reflux for 16 h. The reaction mixture was cooled down and concentrated under reduced pressure. The residue was taken up in dichloromethane, washed with water, dried and concentrated under vacuo. The crude product was purified by silica chromatography (10% ethyl acetate in hexanes) to afford the desired product (12%). ¹H NMR (400 MHz, CDCl₃): δ 7.52 (d, 1H), 6.87 (d, 1H), 6.76 (d, 1H), 6.54 (dd, 1H), 6.07 (d, 1H), 4.86 (m, 1H), 4.34 (m, 4H), 3.56 (t, 2H), 2.85 (s, 3H), 2.81 (s, 3H), 2.65 (t, 2H), 2.62 (s, 6H), 1.59 (d, 3H); MS (ESI) m/z: 469.2 (M⁺+1).

EXAMPLE 54

[1-(5-Chloro-2,3-dimethoxy-phenyl)-ethyl]-(2-methanesulfonyl-5-piperazin-1-yl-phenyl)-amine hydrochloride

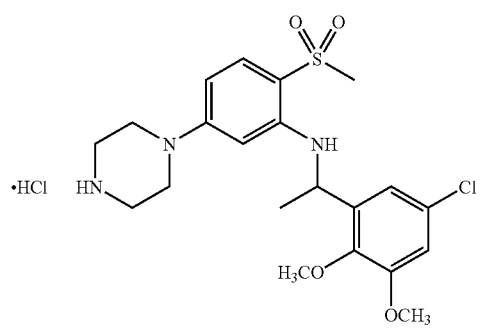

Large scale synthesis of 1-(5-Chloro-2,3-dimethoxy-phenyl)-ethyl]-(2-methanesulfonyl-5-piperazin-1-yl-phenyl)-amine hydrochloride (see Example 25) is described in the following example. [1-(5-Chloro-2,3-dimethoxy-phenyl)-ethyl]-(2-methanesulfonyl-5-piperazin-1-yl-phenyl)-amine (59 g, 0.13 mol) was suspended in 0.2 L DCM and the mixture was heated to give a solution. As 5 M HCl in i-PrOH (26 mL) was added, an exotherm was observed. After 10-15 min of stirring, a solid started to precipitate. The thick slurry was concentrated under vacuum until 10-15 mL solvent remained. 180 mL TBME was added, the solid was filtered, washed with 180 mL TBME and dried under vacuum o/n. The solid was dried at 50 C for 2 hours (30"Hg vacuum); 58.7 g were obtained. HPLC 98.3% purity.

[1-(5-Chloro-2,3-dimethoxy-phenyl)-ethyl]-(2-methanesulfonyl-5-piperazin-1-yl-phenyl)-amine

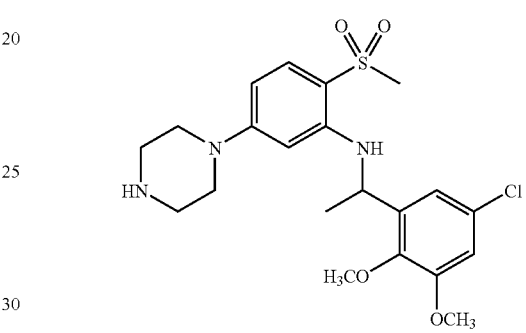

[1-(5-Chloro-2,3-dimethoxy-phenyl)-ethyl]-(5-fluoro-2-methanesulfonyl-phenyl)-amine (100 g, 0.26 mol), piperazine (444 g, 5.16 mol), Hunig's base (0.45 L, 2.6 mol) and ACN (0.75 L) were heated at 80° C. for 13.5 hours (a solution formed upon heating to 67° C.). Upon cooling, a large amount of solids precipitated. Filtration, washing of the filter cake with ACN, and concentration afforded a solid which was treated with 1 L EtOAc. The EtOAc layers were combined and washed with 3×1 L water, dried over sodium sulfate, and concentrated to give 26 g of product. The solid collected by filtration was suspended in 0.5 L DCM and washed with 0.5 L water. The water was back-extracted with 0.25 L DCM. The DCM layers were combined, washed with 7×0.5 L water, dried over sodium sulfate and concentrated. 65 g of the resulting white solid were suspended in TBME and left o/n. The mixture was filtered, re-triturated in 210 mL TBME, filtered, washed with 70 mL TBME and air-dried to afford 59.4 g (50.7%) of product as a white solid.

[1-(5-Chloro-2,3-dimethoxy-phenyl)-ethyl]-(5-fluoro-2-methanesulfonyl-phenyl)-amine

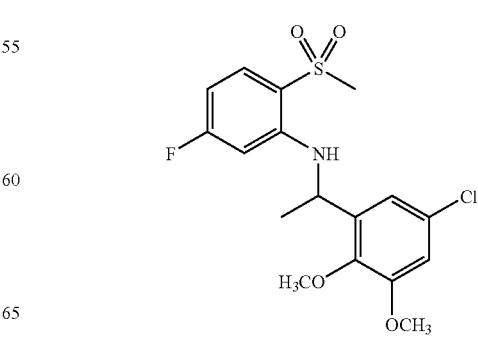

To the solution of 1-(5-chloro-2,3-dimethoxy-phenyl)-ethyl amine (112 g, 0.52 mol) and Hunig's base (0.36 L, 2.1 mol) in DMF (0.5 L), sulfone (99.9 g, 0.52 mol) was added. The reaction mixture was heated to 110° C. for 18 h. The reaction mixture was cooled and two layers separated. The bottom layer (yellow solution, 0.9 L) was mixed with 1.5 L water. An emulsion formed and some oil separated. 1.5 L TBME was added and the organic phase was separated. The aqueous phase was re-extracted with 0.5 L TBME. The combined TBME layers (1.6 L) were washed with water (3×0.5 L), dried over sodium sulfate and concentrated. The concentrate was pre-adsorbed on silica gel (128 g) and loaded on a silica gel plug (384 g). DCM elution and concentration gave 148.7 g of an oil that solidified. It was recrystallized from 325 mL EtOH and washed with 0.1 L EtOH to yield 112.3 g solid that contained product and residual EtOH (by NMR). EtOH was chased with toluene to yield 103.2 g solid (51.1% yield).

1-(5-Chloro-2,3-dimethoxy-phenyl)-ethyl amine

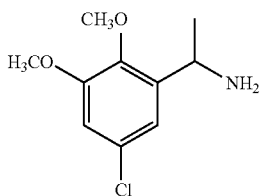

To a solution of 1-(5-chloro-2,3-dimethoxy-phenyl)-ethanone (145.8 g, 0.68 mol) in NH$_3$/EtOH (2M, 2.0 L) was added titanium isopropoxide (482 g, 1.6 mol) over 5-10 min. The temperature increased from 16 to 26° C. after half of the titanium isopropoxide had been added. After the total amount of titanium isopropoxide had been added, the temperature had increased to 32.4° C. The reaction solution was allowed to stir under nitrogen for 16 hours. It was cooled to 1.4° C. and sodium borohydride (61.7 g, 1.6 mol) was added in portions over 40 min. An exotherm was observed (temperature ranged between 5 and 19° C.). The cooling bath was removed and the reaction mixture was stirred for 3.5 hours. TLC (1:4 heptane: acetone) showed no starting material present.

0.52 L of 30% ammonium hydroxide was diluted with water to the total volume of 2 L. The reaction mixture was added to this solution in portions (temperature increased from 21 to 26° C.). The resulting thick white slurry was separated by filtration (filtration was quite slow). Addition of ethyl acetate (~1 L) to the filtrate (~5 L) did not cause separation of layers. The solution was concentrated under reduced pressure to ~2 L volume. Ethyl acetate (1 L) and water (1 L) were added (EtOAc alone was insufficient to cause separation), the organic phase was separated, and the aq. phase was washed with 0.5 L EtOAc. The organic phases were combined, dried over sodium sulfate (~2 Kg) and concentrated. Upon concentration to ~0.5 L an oil separated from the aqueous portion. The layers were separated, the aq. layer was extracted with ~0.1 L EtOAc, and the oil and ethyl acetate solutions were concentrated again. Residual water was removed by chasing with 2×0.2 L of toluene. The oil was left under vacuum to yield 134.5 g of product (91.7% yield, HPLC 93% pure).

1-(5-Chloro-2,3-dimethoxy-phenyl)-ethanone

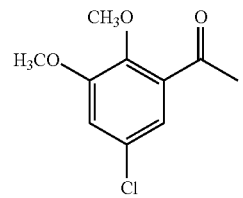

1-(5-Chloro-2,3-dimethoxy-phenyl)-ethanol (204 g, 943 mmol) was dissolved in DCM (2.0 L) and PCC (was added to the reaction mixture in portions, over 2 hours. Over the first 1.5 hours the temperature increased from 17.2° C. to 30.7° C. while a total of 315 g PCC was added. Addition of the remaining PCC did not result in a temperature increase. The reaction mixture was tested by TLC 1 hour after the PCC addition was completed; full conversion was observed. After an additional 40 min, 2 L TBME was added and a 4° C. exotherm was observed. The dark slurry was poured into 0.2 kg celite, mixed, then filtered over an additional 0.2 kg celite. The tar-like material remained in the reaction flask. DCM/TBME solution was concentrated under reduced pressure. A coating of tar formed on the flask walls; a solid also formed. The solid was dissolved in 0.2 L DCM (the tar did not dissolve). The solution was mixed with 0.2 kg silica gel and the DCM was allowed to evaporate. The product pre-adsorbed on silica gel was placed on top of a silica gel plug (0.4 kg silica gel) and the organic material was eluted with TBME until no product was observed by TLC. The resulting yellow solution was concentrated to yield a yellow solid. This solid was re-dissolved in TBME and the solution was flushed through a 0.4 kg silica gel plug. The resulting solution was concentrated to yield 145.8 g dry solid (72% yield, 95% pure by HPLC).

1-(5-Chloro-2,3-dimethoxy-phenyl)-ethanol

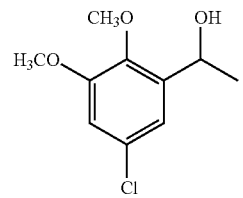

To a mixture of 5-chloro-2,3-dimethoxybenzaldehyde (339, 1.69 mol) in TBME (5.6 L) was added 3M methylmagnesium bromide in ether (660 mL, 1.98 mol) over 1 hour at 9 to 12° C. The mixture was warmed at 33° C. for 1 hour 20 minutes. There was significant starting material present so more methylmagnesium bromide was added (590 mL, 1.77 mol) over 1 hour 20 minutes with the reaction temperature at 33° C. The reaction was cooled to room temperature overnight and poured into ammonium chloride (20 wt %, 3 kg) over 5 minutes. The temperature rose from 11 to 28° C. The reaction flask was rinsed with ammonium chloride solution (500 mL) and TBME (250 mL). The layers were separated and the organic layer was concentrated to an orange yellow thick oil. Yield: 348 g (96% yield, 94% purity).

5-Chloro-2,3-dimethoxybenzaldehyde

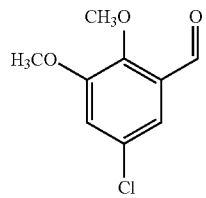

A mixture of 5-Chloro-2-hydroxy-3-methoxybenzaldehyde (275 g, 1.47 mol) and DMF were stirred as potassium carbonate (411 g, 2.97 mol) was added over 5 minutes. The mixture temperature rose from 22 to 29° C. over 10 minutes. Dimethylsulfate (283 g, 2.24 mol) was added over 15 minutes causing a temperature rise from 28 to 47° C. The mixture was then heated with a heating mantle to 61° C. over 15 minutes and stirred at 61° C. for 1.5 hours; the reaction was complete by TLC. The reaction mixture was cooled to 22° C., transferred to a 22-L flask and diluted with water (8.2 L) over 5 minutes; the temperature rose to 38° C. The light yellow mixture was filtered and the flask and filter cake rinsed with 1.5 L water. The solid was dried under vacuum for 15 hour at 50° C. The material contained inorganic salts and was suspended in water (3 L) for 1.5 hours. After filtration and a 500 mL water rinse, the filter cake was dried under by suction and overnight at 65° C. under vacuum. Yield: 305 g (100% yield, 99.1% purity).

5-Chloro-2-hydroxy-3-methoxybenzaldehyde

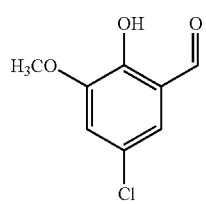

o-Vanillin (100.5 g, 660 mmol), acetic acid (504 mL) and N-chlorosuccinimide (83.8 g, 627 mmol) were mixed and heated to 105° C. over 30 minutes. A rapid exotherm from 55 to 105° C. occurred over 7 minutes. The mixture refluxed for a few minutes and was allowed to cool slowly to room temperature (2.5 h). Water (1 L, 2 volume equivalents) was added to the mixture slowly over 10 minutes. The mixture was stirred for 5 minutes, filtered and the crude product air dried to afford 146.9 g of wet cake as a light yellow powder with 90% product, 3% o-vanillin and 7% dichlorovanillin. Recrystallization from 200 g ethanol afforded 61 g (52% yield).

Biological Tests

The ability of a compound of to the invention to bind a $5\text{-HT}_6$ receptor, and to be pharmaceutically useful, can be determined using in vivo and in vitro assays known in the art. Examples of compounds of the invention as compared to known antipsychotics are shown in the table below.

Compound Binding Profiles

| | $5HT_{1A}$ | $5HT_{2A}$ | $5HT_{2C}$ | $5HT_6$ | D1 | D2 | D3 | D4 | M1 | α1 | α2 | H1 |
|---|---|---|---|---|---|---|---|---|---|---|---|---|
| Clozapine | ▼ | ▲ | = | = | ▼ | ▼ | ▼ | ▼ | ▲ | ▲ | = | = |
| Ziprasidome | ▲ | ▲ | ▲ | = | ▼ | ▲ | ▲ | ▼ | ▲ | ▼ | ▼ | = |
| Aripiprazole | = | = | = | = | ▼ | ▲ | = | ▼ | = | = | ▼ | = |
| Olozapine | | ▲ | ▲ | ▲ | ▼ | = | = | = | ▲ | = | ▼ | ▲ |
| Cpd. A | 420 nM | 2.5* μM | 3.8* μM | 4.0 nM | ▼ | 9.0* μM | 71 nM | ▼ | 3.4* μM | 24* μM | 23* μM | 22* μM |
| Cpd. A − B | ▼ | 1.5* μM | 2.6* μM | 2.1 nM | ▼ | 10* μM | 27 nM | ▼ | 3.5* μM | 8* μM | 25* μM | 25* μM |
| Cpd. E[1] | ▼ | 150 nM | 12 nM | 1.3 nM | ▼ | 613* nM | 2.8 nM | ▼ | 10* μM | 24* μM | 30* μM | 20* μM |

▲ High ($K_i < 10$ nM);
= Moderate ($K_i = 11\text{-}100$ nM);
▼ Low ($K_i = 100\text{-}1000$ nM);
* = Estimated $IC_{50}$
[1] N-(1-(6-Chloro-2,3-dihydrobenzo[b][1,4]dioxin-8-yl)ethyl)-2-(methylsulfonyl)-5-(piperazin-1-yl)benzenamine hydrochloride The following examples demonstrate the utility of compounds of the invention.

EXAMPLE 55

In vivo assay of reduction of food intake. For a review on serotonin and food intake, see Blundell, J. E. and Halford, J. C. G. (1998) Serotonin and Appetite Regulation. Implications for the Pharmacological Treatment of Obesity. CNS Drugs 9:473-495. Obese (ob/ob) mouse may be selected as the primary animal model for screening, since this mutant mouse consumes high amounts of food resulting in a high signal/noise ratio. To further substantiate and compare efficacy data, the effect of the compounds on food consumption may also be studied in wild type (C57BL/6J) mice. The amount of food consumed during 15-20 hours of infusion of compounds is recorded.

Male mice (obese C57BL/6JBom-Lep$^{ob}$ and lean wild-type C57Bl/6JBom; Bomholtsgaard, Denmark) 8-9 weeks with an average body weight of 50 g (obese) and 25 g (lean) are used in all studies. Animals are housed singly in cages at 23±1° C., 40-60% humidity and have free access to water and standard laboratory chow. The 12/12-h light/dark cycle is set to lights off at 5 p.m. Animals are conditioned for at least one week before start of study.

Test compounds are dissolved in solvents suitable for each specific compound such as cyclodextrin, cyclodextrin/methane sulfonic acid, polyethylene glycol/methane sulfonic acid, and saline. Fresh solutions are made for each study. Doses of 30, 50 and 100 mg kg/day are used. The purity of the test compounds is of analytical grade.

Animals are weighed at the start of the study and randomized based on body weight. Osmotic minipumps are used. Continuous subcutaneous infusion with 24 hours duration is used. The minipumps are either filled with different concentrations of test compounds dissolved in vehicle or with only vehicle solution and maintained in vehicle pre-warmed to about 37° C. The minipumps are implanted subcutaneously in the neck/back region under short acting anesthesia. This surgical procedure lasts approximately 5 min.

Food pellet weight is measured at 5 p.m. and at 8 p.m. for two days before (baseline) and one day after minipump implantation. The weigh-in is performed with a computer assisted balance. Occasional spillage is corrected for. At the end of the study the animals are killed by neck dislocation and trunk blood sampled for later analysis of plasma drug concentrations. Plasma sample proteins are precipitated with methanol, centrifuged and the supernatant is transferred to HPLC vials and injected into an LC/MS system. The mass spectrometer is set for electrospray positive ion mode and Multiple Reaction Monitoring. A linear regression analysis of the standards forced through the origin is used to calculate the concentrations of the unknown samples.

Food consumption for 15 hours is measured for the three consecutive days and the percentage of basal level values is derived for each animal from the day before and after treatment. The values are expressed as mean±SD and ±SEM from eight animals per dose group. Statistical evaluation is performed by Kruskal-Wallis one-way ANOVA using the percent basal values. If statistical significance is reached at the level of $p<0.05$, Mann-Whitney U-test for statistical comparison between control and treatment groups is performed. Compounds according to the invention show an effect in the range of 5-200 mg/kg.

The hypophagic effect of two compounds of the invention, Compound B (2-(methylsulfonyl)-N-(1-phenylethyl)-5-(piperazin-1-yl)benzenamine hydrochloride, $K_i=47$ nM) and Compound C (1-(2-(1-(3,5-dimethoxyphenyl)ethylamino)-4-(piperazin-1-yl)phenyl)-2,2,2-trifluoroethanone hydrochloride, $K_i=34$ nM) was evaluated in ob/ob mice as above. As can be seen from the data shown in FIGS. 1A, and B, administration of Compound B (30 mg/kg bid i.p) and Compound C (30 mg/kg qd i.p) for 7 days produced a significant reduction in food intake of 60-70%, which was also accompanied by a significant reduction in body weight (10-15%.)

Figure 2A:
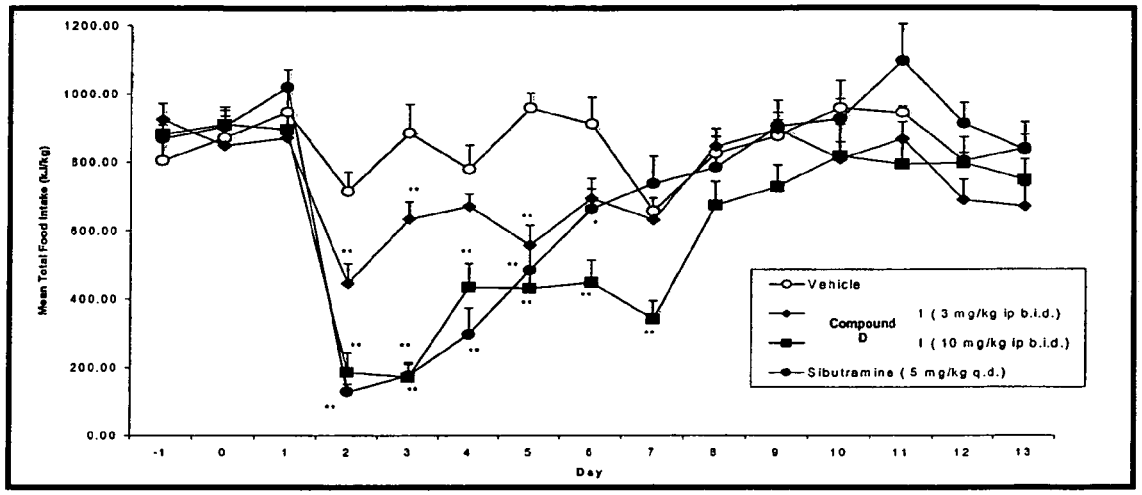
FIG. 2 shows the effect of a compound of the invention, Compound D on food intake (FIG. 2A) and body weight (FIG. 2B) in diet-induced obese rats.
Figure 2B:
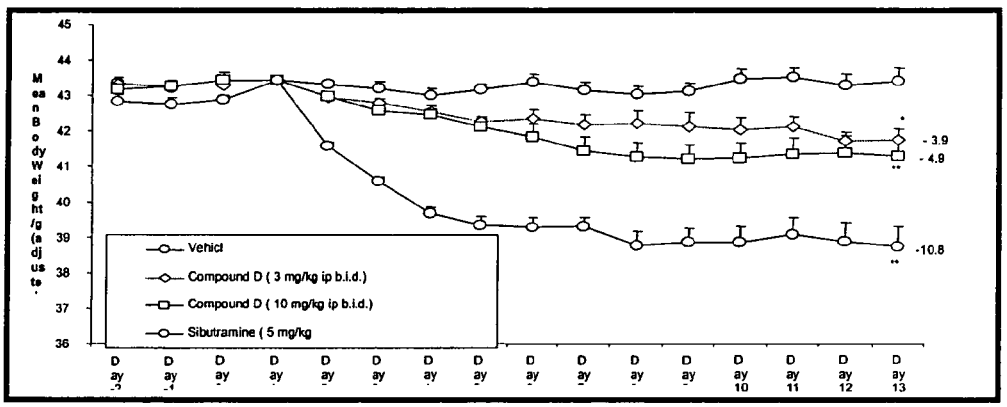
Figure 3:
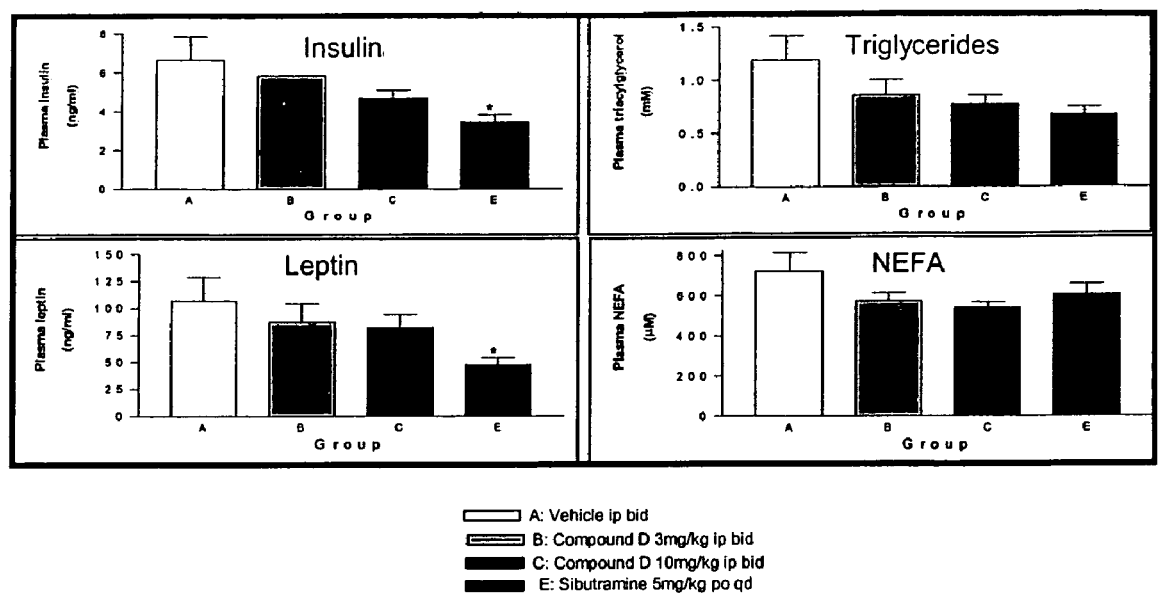
FIG. 3 shows the effect of a compound of the invention, Compound D on plasma biomarkers in diet-induced obese rats.

An additional compound of the invention, Compound D (N-(1-(3,5-dimethoxyphenyl)ethyl-2-(methylsulfonyl)-5-(piperazin-1-yl)-benzeneamine hydrochloride, $K_i=27$ nM), induced a significant decrease in food intake and body weight in DIO (diet-induced obese) rats following two weeks of dosing at 3, 10 mg/kg bid, as seen in FIGS. 2A and 2B. A reduction in plasma levels of Insulin, Leptin, triglycerides, and NEFA was also observed (FIG. 3).

Figure 4A:
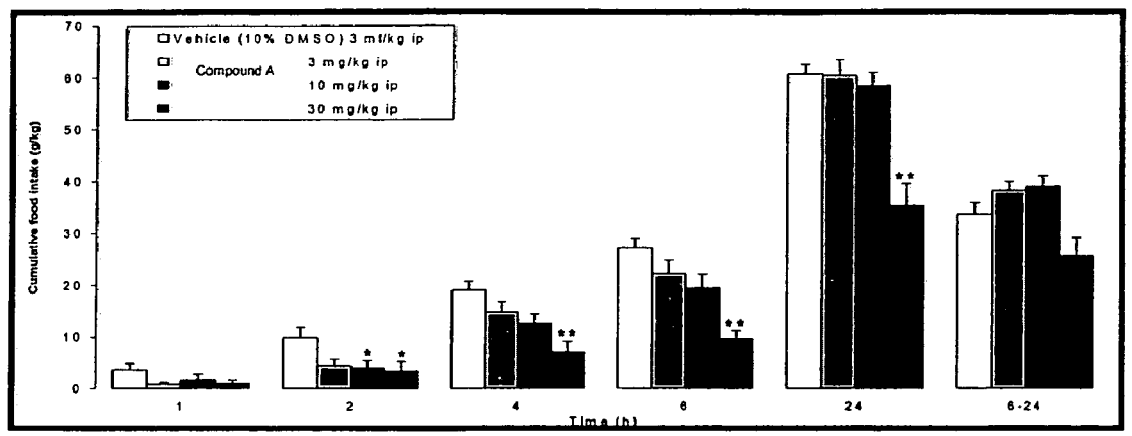
FIG. 4 shows the effect of a compound of the invention, Compound A on food intake (FIG. 4A) and body weight (FIG. 4B) in lean rats.
Figure 4B:
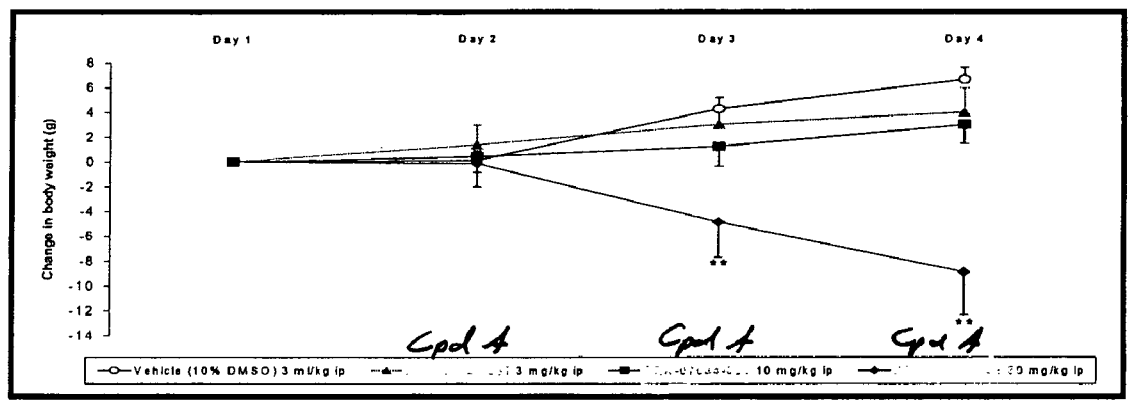

Compound A ([1-(5-Chloro-2,3-dimethoxy-phenyl)-ethyl]-(2-methanesulfonyl-5-piperazin-1-yl-phenyl)-amine hydrochloride salt), a highly selective (>100-fold safety margin to more than 70 tested receptors) 5-HT$_6$ receptor antagonist ($K_i=4$ nM) was found to have excellent bioavailability in dogs (F=81%) and half-life ($T_{1/2}=5$ hr) following oral administration (5 mg/kg). In rodents, the observed bioavailability was 38%, with $T_{1/2}=1.5$ hr following oral administration (5 mg/kg). Compound A also showed no significant CYP inhibition ($IC_{50}>7.5$ mM for CYP1A2, CYP3A4, CYP2C9 and CYP2C19; $IC_{50}=7.8$ µM for CYP2D6) and possesses excellent stability (HLM=>90 minutes). In in vivo studies, Compound A induces a significant reduction in food intake and body weight in rats and mice following sub-chronic dosing (10 and 30 mg/kg qd, i.p.) These data are illustrated in FIGS. 4A and 4B.

Thus, these in vivo experiments demonstrate that the potent and selective 5-HT6 receptor antagonists of the invention induce a dose-dependent reduction in food intake and body weight in different obesity-related animal models. This reduction in body weight was accompanied by an improved plasma profile of a number of co-morbid metabolic factors in ob/ob mice and diet-induced obese rats; as such, the compounds of the invention are expected to provide a useful treatment for obesity.

EXAMPLE 56

This study aimed to test the potential cognitive enhancing properties of Compound A using the novel object recognition test in C57Bl/6J mice.

Material and Methods

Animals

Male C57Bl/6J mice from Jackson Laboratories (Bar Harbor, Me.) were used. Mice were received at 6-weeks of age. Upon receipt, mice were assigned unique identification numbers (tail marked) and were group housed in polycarbonate cages with filter tops. All animals remained housed in groups of four during the remainder of the study. All mice were acclimated to the colony room for at least two weeks prior to testing and were subsequently tested at an average age of 8 weeks of age. During the period of acclimation, mice were examined on a regular basis, handled, and weighed to assure adequate health and suitability. Mice were maintained on a 12/12 light/dark cycle with the light on at 6:00 a.m. The room temperature was maintained between 20 and 23° C. with a relative humidity maintained between 30% and 70%. Chow and water were provided ad libitum for the duration of the study. In each test, animals were randomly assigned across treatment groups.

Drugs

The following compounds were used for this study:

Test Compound:

Compound A (doses 1, 3, and 10 mg/kg). The pH at the 10 mg/kg was around 5.5.

Reference Compounds:

Rolipram (0.1 mg/kg, Sigma, Lot #054K4610)

Compound A was dissolved in 10% DMSO and sterile water and administered intraperitoneally on day 1 after habituation and also 20 min prior to training on Day 2. Rolipram, also dissolved in 10% DMSO was only administered 20 min prior to training on Day 2.

Methods

Novel Object Recognition

On Day 1, mice were habituated to a circular open field environment (d=18 in, h=15 cm) for one hour in cage groups of four. Each Arena was constructed out of acrylic that was painted black to block reflection. On day 2, mice were placed back into the same arena for a training trial and allowed to explore a set of two identical objects placed equidistance apart from both each other and the arena walls. Individual mice were trained for a total of 15 minutes and then placed back into their home cages. On Day 3, mice were placed back into the same arena in the presence of both the familiar (previously explored) and a novel object. The spatial positions of the familiar and novel object (i.e. left-right sides) were counterbalanced between subjects. The difference in time spent exploring each object during the test trial was used as an index of object recognition and memory retention. Each animals test trial was recorded and these tapes were observed and scored after test completion. The first 10 min of each session was scored and object recognition was computed using the formula:

(Time spent with novel object*100)/(Total Time exploring both objects).

Tissue Harvest

On Day 4, mice were injected with vehicle or Compound A compound and cardiac blood and brains were collected 20 min after injection. Samples were collected from 4 mice per dose level and stored at −80° C. until shipment to analytical lab.

Statistical Analysis

Data were analyzed by analysis of variance (ANOVA) followed by post-hoc comparisons with Fisher Tests when appropriate. An effect was considered significant if p<0.05. Data are represented as the mean and standard error to the mean.

Results

Memory Index

Figure 5:
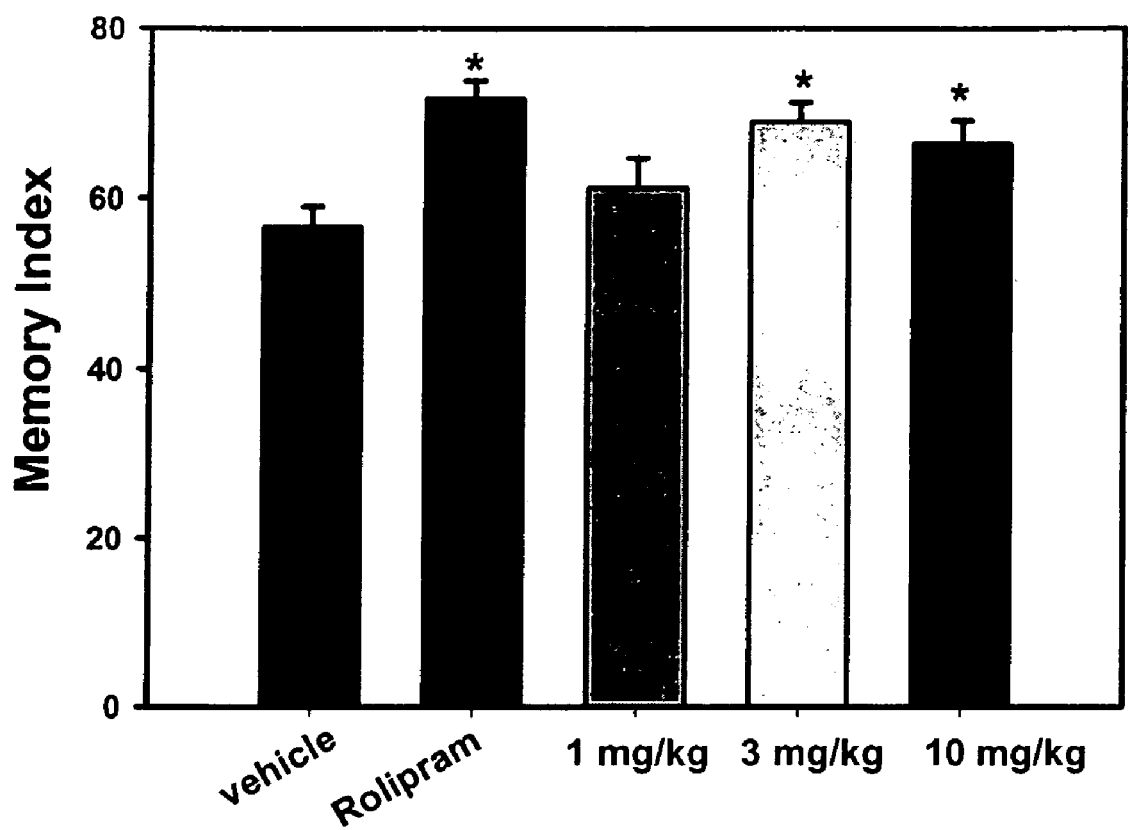
FIG. 5 illustrates the effect of rolipram and a compound of the invention, Compound A (1, 3, and 10 mg/kg) on object recognition over a test trial as further described in Example 55. Data represent mean±SEM of 10 mice/treatment group (*=p<0.05 compared with vehicle)

The effects of Compound A and rolipram on memory index are shown in FIG. 5. ANOVA found a significant treatment effect. The reference compounds rolipram (0.1 mg/kg) significantly increased the recognition index during the 10 min test. In addition, at 3 mg/kg and 10 mg/kg, Compound A significantly increased the recognition index (p=0.002 and 0.01, respectively).

Fisher's PLSD for Memory Index
Effect:
Significance Level: 5

|  | Mean Diff. | Crit. Diff. | P-Value |  |
|---|---|---|---|---|
| Vehicle, Rolipram 0.1 mg/kg | — | 7.680 | .0003 | S |
| Vehicle, Compound A 1 mg/kg | −4.573 | 7.680 | .2367 |  |
| Vehicle, Compound A 3 mg/kg | — | 7.680 | .0023 | S |
| Vehicle, Compound A 10 mg/kg | −9.784 | 7.680 | .0137 | S |
| Rolipram 0.1 mg/kg, Compound A 1 mg/kg | 10.491 | 7.680 | .0085 | S |
| Rolipram 0.1 mg/kg, Compound A 3 mg/kg | 2.725 | 7.680 | .4785 |  |
| Rolipram 0.1 mg/kg, Compound A 10 mg/kg | 5.279 | 7.680 | .1730 |  |
| PRX-07034-001 1 mg/kg, Compound A 3 mg/kg | −7.766 | 7.680 | .0476 | S |
| PRX-07034-001 1 mg/kg, Compound A 10 mg/kg | −5.211 | 7.680 | .1785 |  |
| PRX-07034-001 3 mg/kg, Compound A 10 mg/kg | 2.555 | 7.680 | .5063 |  |

Effect of Compound A on Exploration Time

Figure 6:
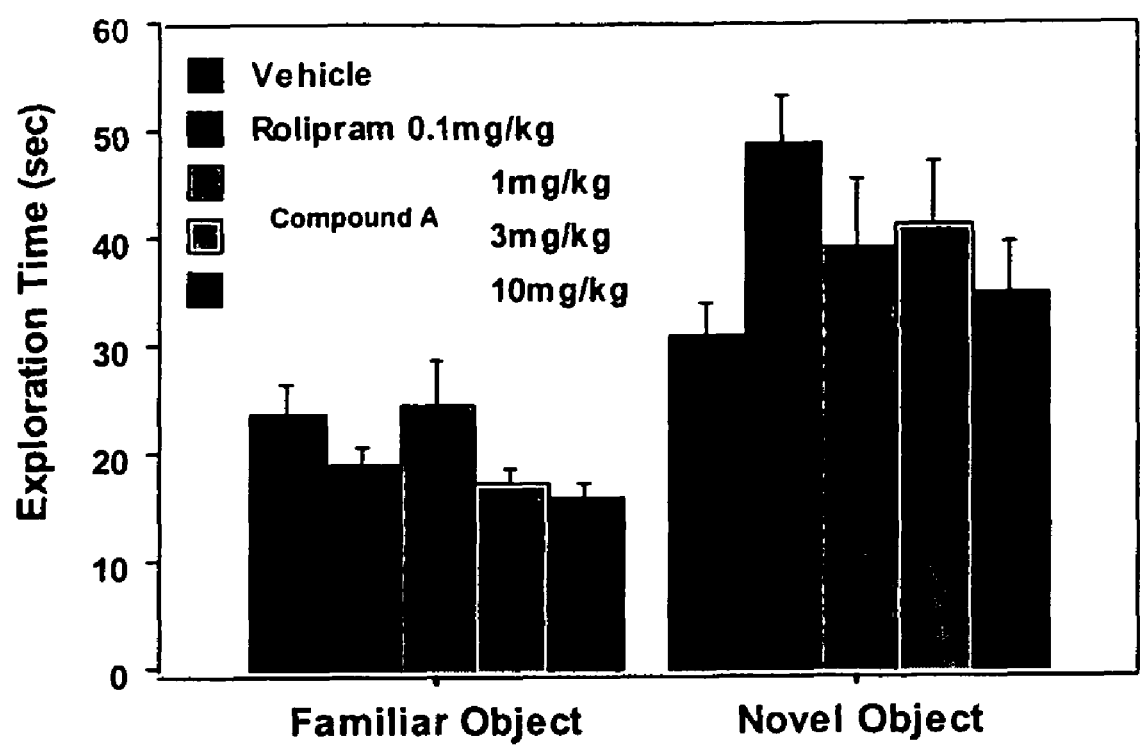
FIG. 6 illustrates the effect of rolipram and Compound A (1, 3, and 10 mg/kg) on exploration time during testing as more fully described in Example 56. Data represent mean±SEM of 10 mice/treatment group.

The effects of Compound A exploration time of both novel and familiar objects are presented in FIG. 6. ANOVA found no significant treatment effect on this measure, but a significant time effect and a significant time×treatment interaction. Post hoc analysis found that mice treated with rolipram or Compound A (1, 3, and 10 mg/kg) spent more time exploring novel object than the familiar object.

Means Table for Memory Index

|  | Count | Mean | Std. Dev. | Std. Err. |
|---|---|---|---|---|
| Vehicle | 10 | 56.607 | 7.828 | 2.476 |
| Rolipram 0.1 mg/kg | 10 | 71.670 | 6.836 | 2.162 |
| Compound A 1 mg/kg | 10 | 61.179 | 11.191 | 3.539 |
| Compound A 3 mg/kg | 10 | 68.946 | 7.325 | 2.316 |
| Compound A 10 mg/kg | 10 | 66.391 | 8.749 | 2.767 |

ANOVA Table for Memory Index

|  | DF | Sum of Squares | Mean Square | F-Value | P-Value | Lambda | Power |
|---|---|---|---|---|---|---|---|
| Treatment | 4 | 1470.338 | 367.584 | 5.057 | .0019 | 20.227 | .953 |
| Residual | 45 | 3271.069 | 72.690 |  |  |  |  |

Means Table for Exploration Time

|  | Count | Mean | Std. Dev. | Std. Err |
|---|---|---|---|---|
| Vehicle, Familiar Object | 10 | 23.979 | 8.759 | 2.770 |
| Vehicle, Novel Object | 10 | 30.984 | 10.440 | 3.301 |
| Rolipram 0.1 mg/kg, Familiar Object | 10 | 19.172 | 5.539 | 1.752 |
| Rolipram 0.1 mg/kg, Novel Object | 10 | 48.975 | 14.037 | 4.439 |
| Compound A 1 mg/kg, Familiar Object | 10 | 24.810 | 13.254 | 4.191 |
| Compound A 1 mg/kg, Novel Object | 10 | 39.266 | 19.640 | 6.211 |
| Compound A 3 mg/kg, Familiar Object | 10 | 17.506 | 4.004 | 1.266 |
| Compound A 3 mg/kg, Novel Object | 10 | 41.377 | 18.070 | 5.714 |
| Compound A 10 mg/kg, Familiar Object | 10 | 16.153 | 4.064 | 1.285 |
| Compound A 10 mg/kg, Novel Object | 10 | 35.031 | 14.815 | 4.685 |

ANOVA Table for Exploration Time

|  | DF | Sum of Squares | Mean Square | F-Value | P-Value | Lambda | Power |
|---|---|---|---|---|---|---|---|
| Treatment | 4 | 929.095 | 232.274 | 1.033 | .4006 | 4.133 | .293 |
| Subject(Group) | 45 | 10115.807 | 224.796 |  |  |  |  |
| Category for Exploration Time | 1 | 8838.444 | 8838.444 | 102.916 | <.0001 | 102.916 | 1.000 |
| Category for Exploration Time * Treatment | 4 | 1523.897 | 380.974 | 4.436 | .0042 | 17.745 | .919 |
| Category for Exploration Time * Subject(Group) | 45 | 3864.595 | 85.880 |  |  |  |  |

| | Fisher's PLSD for Exploration Time<br>Effect: Category for Exploration Time<br>Significance Level: 5% | | |
|---|---|---|---|
| | Mean Diff. | Crit. Diff. | P-Value |
| Familar Object, Novel Object | −18.803 | 3.733 | <.0001 S |

| Comparison | Diff of Means | LSD (alpha = 0.050) | P | Diff >= LSD |
|---|---|---|---|---|
| Comparisons for factor: Exploration Time within 10% DMSO | | | | |
| Novel vs. Familiar | 7.005 | 8.347 | 0.098 | No |
| Comparisons for factor: Exploration Time within Rolipram | | | | |
| Novel vs. Familiar | 29.803 | 8.347 | <0.001 | Yes |
| Comparisons for factor: Exploration Time within Compound A (1 mg/kg) | | | | |
| Novel vs. Familiar | 14.456 | 8.347 | 0.001 | Yes |
| Comparisons for factor: Exploration Time within Compound A (3 mg/kg) | | | | |
| Novel vs. Familiar | 23.871 | 8.347 | <0.001 | Yes |
| Comparisons for factor: Exploration Time within Compound A (10 mg/kg) | | | | |
| Novel vs. Familiar | 18.878 | 8.347 | <0.001 | Yes |

| Comparisons for factor: Treatment within Familiar | | | | |
|---|---|---|---|---|
| Comparison | Diff of Means | LSD (alpha = 0.050) | P | Diff >= LSD |
| 10% DMSO vs. Cpd. A - 1 mg/kg | 0.831 | 11.104 | 0.882 | No |
| 10% DMSO vs. Cpd. A - 10 mg/kg | 7.826 | 11.104 | 0.164 | No |
| 10% DMSO vs. Cpd. A - 3 mg/kg | 6.473 | 11.104 | 0.249 | No |
| 10% DMSO vs. Rolipram | 4.807 | 11.104 | 0.391 | No |
| Rolipram vs. Cpd. A - 10 mg/kg | 3.019 | 11.104 | 0.590 | No |
| Rolipram vs. Cpd. A - 3 mg/kg | 1.666 | 11.104 | 0.766 | No |
| Cpd. A - 3 mg/kg vs. Cpd. A - 10 mg/kg | 1.353 | 11.104 | 0.809 | No |
| Cpd. A - 1 mg/kg vs. Cpd. A - 10 mg/kg | 8.657 | 11.104 | 0.125 | No |
| Cpd. A - 1 mg/kg vs. Cpd. A - 3 mg/kg | 7.304 | 11.104 | 0.194 | No |
| Cpd. A - 1 mg/kg vs. Rolipram | 5.638 | 11.104 | 0.315 | No |

| Comparisons for factor: Treatment within Novel | | | | |
|---|---|---|---|---|
| Comparison | Diff of Means | LSD (alpha = 0.050) | P | Diff >= LSD |
| Rolipram vs. 10% DMSO | 17.991 | 11.104 | 0.002 | Yes |
| Cpd. A - 1 mg/kg vs. 10% DMSO | 8.282 | 11.104 | 0.142 | No |
| Cpd. A - 3 mg/kg vs. 10% DMSO | 10.393 | 11.104 | 0.066 | No |
| Cpd. A - 10 mg/kg vs. 10% DMSO | 4.047 | 11.104 | 0.470 | No |
| Cpd. A - 3 mg/kg vs. Cpd. A - 10 mg/kg | 6.346 | 11.104 | 0.259 | No |
| Cpd. A - 3 mg/kg vs. Cpd. A - 1 mg/kg | 2.111 | 11.104 | 0.706 | No |
| Cpd. A - 1 mg/kg vs. Cpd. A - 10 mg/kg | 4.235 | 11.104 | 0.450 | No |
| Rolipram vs. Cpd. A - 10 mg/kg | 13.944 | 11.104 | 0.015 | Yes |
| Rolipram vs. Cpd. A - 1 mg/kg | 9.709 | 11.104 | 0.086 | No |
| Rolipram vs. Cpd. A - 3 mg/kg | 7.598 | 11.104 | 0.177 | No |

It is seen from the above data that Compound A (3 and 10 mg/kg) produces a significant, positive effect on object recognition compared to vehicle-treated mice. This effect suggests a potential for cognitive enhancement activity for this compound. The reference compound Rolipram (0.1 mg/kg i.p), as expected, had a significant, positive effect on object recognition indicating that this experiment was functioning. No significant treatment effect was found on novel vs familiar object exploration time. Rolipram and Compound A-treated mice spent more time exploring the novel object.

EXAMPLE 57

The following example details the resolution of enantiomers of the compound of Example 25, [1-(5-Chloro-2,3-dimethoxy-phenyl)-ethyl]-(2-methanesulfonyl-5-piperazin-1-yl-phenyl)-amine hydrochloride.

Chiral Separation of Free Base Enantiomers

Column Packing: A 2 inch column was packed with 500 grams of CHIRALCEL OJ using 50:50 IPA:heptane as slurry solvent. The column was packed to 2000 psi. The column was flushed and equilibrated prior to starting the $1^{st}$ pass injections.

Method for purification: 70:30 heptane (+0.1% diethylamine)/ethanol was the mobile phase.

$1^{st}$ Pass Prep Injections:

Loading: 200-250 mg of free base in 10 mL of Ethanol was heated until dissolved.

Prep Injections: 22 injections were performed. 2.0 grams of peak 1 were isolated as an off-white solid (Chiral purity: 99%). Peak 2 was pooled if the chiral purity was greater than 90%.

$2^{nd}$ Pass Prep Injections:

Loading: 200-250 mg of off-spec peak 2 in 10 mL of ethanol was heated until dissolved.

Prep Injections: 8 injections were performed. 1.3 grams of peak 2 was isolated as an off-white solid (Chiral purity: 99%).

2. Preparations of (+)- and (−)-enantiomer

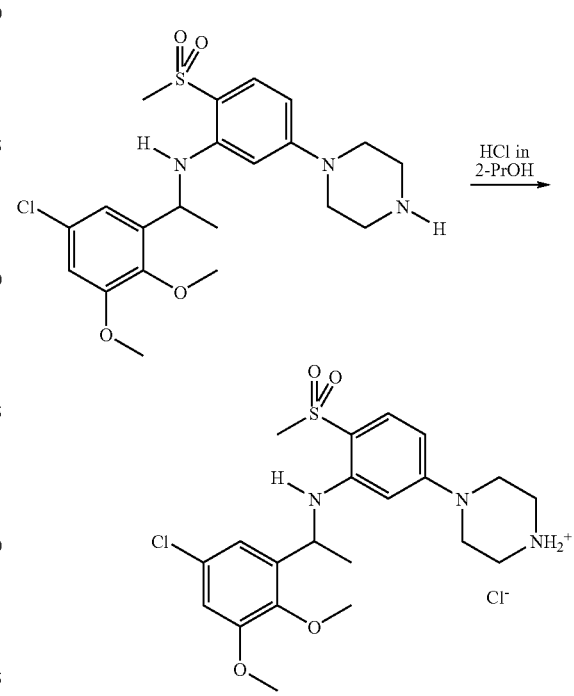

Salt of Peak 1:

Starting materials: Peak 1, 2 g, 4.4 mmol; 2-PrOH, 40 mL; 5.5 M HCl in 2-PrOH, 0.92 mL, 5.0 mmol, 1.15 eq The free base (99.1% chiral purity) and 2-propanol were heated to 80° C. to give a clear solution. To this solution was added HCl in 2-propanol and the solution was removed from the heat and allowed to cool to room temperature, and then in an ice bath for 10 minutes. The mixture was filtered and the filter cake washed with room temperature 2-propanol and dried by suction overnight. The solid was dried for three days at 40° C. and two days at 55 to 70° C. Final mass: 1.08 g (50% yield). $^1$H NMR showed the presence of approximately 3.9% residual 2-propanol. HPLC purity: 99.3% AUC; chiral purity: 100%. This is the dextrorotatory or (+) isomer. This compound shows a 5-HT$_6$ K$_i$ of 18 nM.

Salt of Peak 2:

Starting materials: Peak 2, 1.3 g, 2.86 mmol; 2-PrOH, 26 mL; 5.5 M HCl in 2-PrOH, 0.60 mL, 3.3 mmol, 1.15 eq The free base (99.0% chiral purity) and 2-propanol were heated to 80° C. to give a clear dark yellow solution. To this solution was added HCl in 2-propanol and the solution was removed from the heat and allowed to cool to room temperature overnight. The brown mixture was filtered and the pale pink filter cake washed with room temperature 2-propanol until the washes were colorless. The solid was dried for three days at 40° C. and two days at 75° C. during the day and 60° C. at night. Final mass: 0.95 g (67% yield). $^1$H NMR showed the presence of approximately 2.7% residual 2-propanol. HPLC purity: 100% AUC. This is the levorotatory or (−) isomer. This compound shows a 5-HT$_6$ K$_i$ of 4.5 nM.

EQUIVALENTS

Those skilled in the art will recognize, or be able to ascertain using no more than routine experimentation, numerous equivalents to the specific procedures described herein. Such equivalents are considered to be within the scope of the invention and are covered by the following claims. Various substitutions, alterations, and modifications may be made to the invention without departing from the spirit and scope of the invention as defined by the claims. Other aspects, advantages, and modifications are within the scope of the invention. The contents of all references, issued patents, and published patent applications cited throughout this application are hereby incorporated by reference. The appropriate components, processes, and methods of those patents, applications and other documents may be selected for the invention and embodiments thereof.

What is claimed is:

1. A compound of formula I:

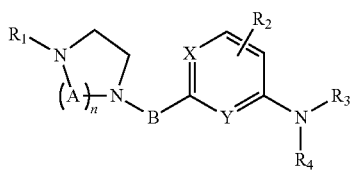

or a pharmaceutically acceptable salt or ester thereof, wherein
n is 1, 2, 3, or 4;
A is a lower alkyl group;
$R_1$ is hydrogen or substituted or unsubstituted alkyl;
$R_2$ is —SO$_2$—(C$_1$-C$_6$ alkyl); —SO$_2$-haloalkyl; or haloalkoxy;
$R_3$ is hydrogen, substituted or unsubstituted alkyl, aryl, alkylaryl, heteroaryl or alkylheteroaryl; $R_4$ is substituted or unsubstituted aryl, alkylaryl, heteroaryl or alkylheteroaryl; or, taken together, $R_3$ and $R_4$ form one substituted or unsubstituted heteroaryl group;
B, when present, is lower alkyl; and
X and Y are CH.

2. The compound of claim 1, wherein A is methylene, ethylene, or propylene, and n=1.

3. The compound of claim 1, wherein $R_1$ is lower alkyl.

4. The compound of claim 1, wherein $R_4$ is alkylaryl.

5. A compound of formula III:

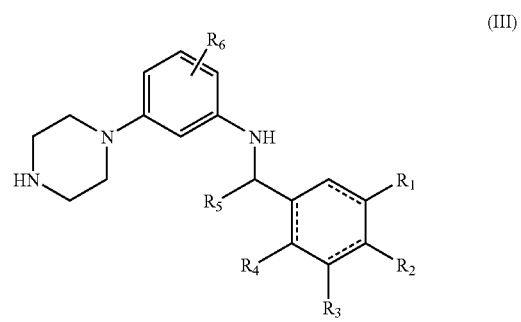

or a pharmaceutically acceptable salt or ester thereof, wherein
$R_1$, $R_2$, $R_3$ and $R_4$ independently are hydrogen, halo or lower alkoxy, or two adjoining $R_1$, $R_2$, $R_3$ or $R_4$ lower alkoxy groups may, taken with the benzyl ring to which they are attached, combine to form a ring;
$R_5$ is hydrogen or lower alkoxy; and
$R_6$ is a sulfone or COCF$_3$.

6. The compound of claim 1, wherein the compound is [1-(5-Chloro-2,3-dimethoxy-phenyl)-ethyl]-(2-methylsulfonyl-5-piperazin-1-yl-phenyl)-amine, or a pharmaceutically acceptable salt or ester thereof.

7. The compound of claim 1, wherein the compound is (2-(methylsulfonyl)-N-(1-phenylethyl)-5-(piperazin-1-yl) benzenamine, or a pharmaceutically acceptable salt or ester thereof.

8. The compound of claim 1, wherein the compound is (N-(1-(3,5-dimethoxyphenyl)ethyl)-2-(methylsulfonyl)-5-(piperazin-1-yl)-benzeneamine, or a pharmaceutically acceptable salt or ester thereof.

9. The compound of claim 1, wherein the compound is N-(1-(6-Chloro-2,3-dihydrobenzo[b][1,4]dioxin-8-yl) ethyl)-2-(methylsulfonyl)-5-(piperazin-1-yl)benzenamine, or a pharmaceutically acceptable salt or ester thereof.

10. The compound of claim 1, wherein the compound is N-(1-(5-Chloro-2-methoxyphenyl)ethyl)-2-(methylsulfonyl)-5-(piperazin-1-yl)benzenamine, or a pharmaceutically acceptable salt or ester thereof.

11. The compound of claim 5, wherein the compound is 1-(2-(3,5-Dimethoxybenzylamino)-4-(piperazin-1-yl)phenyl)-2,2,2-trifluoroethanone, or a pharmaceutically acceptable salt or ester thereof.

12. The compound 4-Methoxy-N-(1-phenyl)ethyl)-3-(piperazin-1-yl)benzenamine, or a pharmaceutically acceptable salt or ester thereof.

13. The compound of claim 5, wherein the compound is 1-(2-(3-bromobenzylamino)-4-(piperazin-1-yl)phenyl)-2,2, 2-trifluoroethanone, or a pharmaceutically acceptable salt or ester thereof.

14. The compound of claim 1, wherein the compound is N-(1-(3-Chloro-4,5-dimethoxyphenyl)ethyl)-2-(methylsulfonyl)-5-(piperazin-1-yl)-benzeneamine, or a pharmaceutically acceptable salt or ester thereof.

15. The compound of claim 1, wherein the compound is N-(1-(3-Chloro-5-methoxyphenyl)ethyl)-2-(methylsulfonyl)-5-(piperazin-1-yl)-benzeneamine, or a pharmaceutically acceptable salt or ester thereof.

16. The compound of claim 1, wherein the compound is N-(1-(3-Trifluoromethyl)ethyl)-2-(methylsulfonyl)-5-(piperazin-1-yl)-benzeneamine, or a pharmaceutically acceptable salt or ester thereof.

17. The compound of claim 1, wherein the compound is N-(2-(Methylsulfonyl)-5-(piperazin-1-yl)phenyl)naphthalen-1-amine, or a pharmaceutically acceptable salt or ester thereof.

18. A pharmaceutical composition comprising the compound of claim 1 and a pharmaceutically-acceptable carrier.

19. 1-(2-(3,5-Dichlorobenzylamino)-4-(piperazin-1-yl)phenyl)-2,2,2-trifluoroethanone;
[1-(5-Chloro-2,3-dimethoxy-phenyl)-ethyl]-(2-methylsulfonyl-5-piperazin-1-yl-phenyl)-amine;
1,2,3,4-Tetrahydro-N-(2-(methylsulfonyl)-5-(piperazin-1-yl)phenyl)naphthalen-1-amine;
N-(1-(3,5-Dichlorophenyl)ethyl)-2-(methylsulfonyl)-5-(piperazin-1-yl)benzeneamine;
N-(2-(methylsulfonyl)-5-(piperazin-1-yl)phenyl)benzo[b]thiophen-3-amine;
1,2,3,4-Tetrahydro-6,7-dimethoxy-N-(2-(methylsulfonyl)-5-(piperazin-1-yl)phenyl)naphthalen-1-amine;
1,2,3,4-Tetrahydro-5,8-dimethoxy-N-(2-(methylsulfonyl)-5-(piperazin-1-yl)phenyl)naphthalen-1-amine;
1,2,3,4-Tetrahydro-6-methoxy-N-(2-(methylsulfonyl)-5-(piperazin-1-yl)phenyl)naphthalen-1-amine;
6-Chloro-N-(2-(methylsulfonyl)-5-(piperazin-1-yl)phenyl)chroman-4-amine;
N-(2-(Methylsulfonyl)-5-(piperazin-1-yl)phenyl)chroman-4-amine;
N-(1-(5-Chlorobenzo[d][1,3]dioxol-7-yl)ethyl)-2-(methylsulfonyl)-5-(piperazin-1-yl)benzenamine;
1,2,3,4-Tetrahydro-2-methyl-N-(2-(methylsulfonyl)-5-(piperazin-1-yl)phenyl)naphthalen-1-amine;
(1-(5-Fluoro-2-methoxy-3-chlorophenyl)ethyl)-2-(methylsulfonyl)-5-(piperazin-1-yl)benzenamine;
(1-(5-Fluoro-2-methoxy-3-methylphenyl)ethyl)-2-(methylsulfonyl)-5-(piperazin-1-yl)benzenamine;
N-(1-(5-Chloro-2,3-dimethoxyphenyl)ethyl)-5-(4-methylpiperazin-1-yl)-2-(methylsulfonyl)benzenamine;
1-(3-(1-(5-Chloro-2,3-dimethoxyphenyl)ethylamino)-4-(methylsulfonyl)phenyl)-N,N-dimethylpiperidin-4-amine;
(R)-1-(3-(1-(5-Chloro-2,3-dimethoxyphenyl)ethylamino)-4-(methylsulfonyl)phenyl)pyrrolidin-3-amine;
N-(3,5-Dichlorobenzyl)-2-nitro-5-(piperazin-1-yl)benzeneamine;
N-(1-(3,5-Dichlorophenyl)ethyl)-2-nitro-5-(piperazin-1-yl)benzeneamine;
N-(3,5-Dichlorobenzyl)-2-(methylsulfonyl)-5-(piperazin-1-yl)benzenamine;
N-(3-Chlorobenzyl)-4-nitro-3-(piperazin-1-yl)benzenamine;
N-(1-(3,5-Dichlorophenyl))ethyl-4-nitro-3-(piperazin-1-yl)benzenamine;
5-(1,4-Diazepan-1-yl)-2-nitro-N-(1-phenylethyl)benzenamine;
1-(3-(1-(7-chloro-2,3-dihydrobenzo[b][1,4]dioxin-5-yl)ethylamino)-4-(methylsulfonyl)phenyl)-N,N-dimethylpiperidin-4-amine;
$N^3$-(1-(6-Chloro-2,3-Dihydrobenzo[b][1,4]dioxin-8-yl)ethyl)-$N^1$-((2-dimethylamino)ethyl)-$N^1$-methyl-4-(methylsulfonyl)-benzene-1,3-diamine;
1-(2-(1-(3,5-Dimethoxyphenyl)ethylamino)-4-(piperazin-1-yl)phenyl)-2,2,2-trifluoroethanone;
1-(2-(1-Phenylethylamino)-4-(piperazin-1-yl)phenyl)-2,2,2-trifluoroethanone;
1-(2-(1-(3,5-Dimethoxyphenyl)ethylamino)-4-(piperazin-1-yl)phenyl)-2,2,2-trifluoroethanone;
1-(2-(1-(3,5-Dichlorophenyl)ethylamino)-4-(piperazin-1-yl)phenyl)-2,2,2-trifluoroethanone;
(S)-1-(2-(1-Phenylethylamino)-4-(piperazin-1-yl)phenyl)-2,2,2-trifluoroethanone;
(R)-1-(2-(1-Phenylethylamino)-4-(piperazin-1-yl)phenyl)-2,2,2-trifluoroethanone;
N-(3-Chlorobenzyl)-2-nitro-5-(piperazin-1-yl)benzenamine;
N-(1-(3-Chlorophenyl)ethyl)-2-nitro-5-(piperazin-1-yl)benzenamine;
N-(1-(3,5-Dimethoxyphenyl)ethyl)-2-nitro-5-(piperazin-1-yl)benzenamine;
N-(2-Methyl-1-phenylpropyl)-2-nitro-5-(piperazin-1-yl)benzenamine;
N-(1-(3-Bromophenyl)ethyl)-2-nitro-5-(piperazin-1-yl)benzenamine;
N-(3-Bromobenzyl)-2-nitro-5-(piperazin-1-yl)benzenamine; or
N-(1-(3,5-Dimethylphenyl)ethyl)-2-nitro-5-(piperazin-1-yl)benzenamine; or a pharmaceutically acceptable salt thereof.

20. N-(1-(5-Chlorobenzo[d][1,3]dioxol-7-yl)ethyl)-2-(methylsulfonyl)-5-(piperazin-1-yl)benzenamine, or a pharmaceutically acceptable salt thereof.

21. The compound of claim 20, wherein said compound is N-(1-(5-chlorobenzo[d][1,3]dioxol-7-yl)ethyl)-2-(methylsulfonyl)-5-(piperazin-1-yl)benzenamine hydrochloride.

22. A pharmaceutical composition comprising a compound of claim 1 and an atypical antipsychotic agent.

23. The pharmaceutical composition of claim 22, wherein the atypical antipsychotic agent is aripiprazole, clozapine, olanzapine, quetiapine, risperidone, or ziprasidone.

24. A pharmaceutical composition comprising N-(1-(5-Chlorobenzo[d][1,3]dioxol-7-yl)ethyl)-2-(methylsulfonyl)-5-(piperazin-1-yl)benzenamine, or a pharmaceutically acceptable salt thereof, and a pharmaceutically-acceptable carrier.

25. The compound of claim 1, wherein the substituted aryl, alkylaryl, heteroaryl or alkylheteroaryl of $R_3$ or $R_4$ are independently substituted by one or more substituents selected from the group consisting of halogen, hydroxyl, alkoxy, carboxylate, amino, trifluoromethyl, and alkyl; and wherein the substituted alkyl of $R_3$ is substituted by one or more substituents selected from the group consisting of halogen, hydroxyl, alkoxy, carboxylate, amino, and trifluoromethyl.

26. The compound of claim 1, wherein n is 1 and A is ethylene.

27. The compound of claim 26, wherein B is absent.

28. The compound of claim 27, wherein $R_1$ and $R_3$ are hydrogen.

29. The compound of claim 28, wherein $R_2$ is —$SO_2$—($C_1$-$C_6$ alkyl).

30. The compound of claim 28, wherein $R_2$ is —$SO_2$—$R_6$, wherein $R_6$ is methyl, ethyl, n-propyl, isopropyl, n-butyl, tert-butyl, or isobutyl.

31. The compound of claim 28, wherein $R_2$ is —$SO_2$-methyl.

32. The compound of claim 29, wherein $R_4$ is alkylaryl.

33. The compound of claim 31, wherein $R_4$ is alkylaryl.

34. The compound of claim 29, wherein $R_4$ is alkylaryl substituted by one or more substituents selected from the group consisting of halogen, hydroxyl, alkoxy, carboxylate, amino, trifluoromethyl, and alkyl.

35. The compound of claim 31, wherein $R_4$ is alkylaryl substituted by one or more substituents selected from the group consisting of halogen, hydroxyl, alkoxy, carboxylate, amino, trifluoromethyl, and alkyl.

36. The compound of claim 29, wherein $R_4$ is benzyl substituted by one or more substituents selected from the group consisting of halogen, hydroxyl, alkoxy, carboxylate, amino, trifluoromethyl, and alkyl.

37. The compound of claim 31, wherein $R_4$ is benzyl substituted by one or more substituents selected from the group consisting of halogen, hydroxyl, alkoxy, carboxylate, amino, trifluoromethyl, and alkyl.

38. The compound of claim 5, wherein $R_6$ is —$SO_2$—($C_1$-$C_6$ alkyl).

39. The compound of claim 5, wherein $R_6$ is —$SO_2$—$R_6$, wherein $R_6$, is methyl, ethyl, n-propyl, isopropyl, n-butyl, tert-butyl, or isobutyl.

40. The compound of claim 5, wherein $R_6$ is —$SO_2$-methyl.

41. [1-(5-Chloro-2,3-dimethoxy-phenyl)-ethyl]-(2-methylsulfonyl-5-piperazin-1-yl-phenyl)-amine.

42. The compound of claim 41, wherein the chiral purity of the R isoform is at least about 99%.

43. The compound of claim 41, wherein the chiral purity of the S isoform is at least about 99%.

44. (R)-[1-(5-Chloro-2,3-dimethoxy-phenyl)-ethyl]-(2-methylsulfonyl-5-piperazin-1-yl-phenyl)-amine.

45. (S)-[1-(5-Chloro-2,3-dimethoxy-phenyl)-ethyl]-(2-methylsulfonyl-5-piperazin-1-yl-phenyl)-amine.

46. A pharmaceutically acceptable salt of [1-(5-Chloro-2,3-dimethoxy-phenyl)-ethyl]-(2-methylsulfonyl-5-piperazin-1-yl-phenyl)-amine.

47. A pharmaceutically acceptable salt of (R)-[1-(5-Chloro-2,3-dimethoxy-phenyl)-ethyl]-(2-methylsulfonyl-5-piperazin-1-yl-phenyl)-amine.

48. A pharmaceutically acceptable salt of (S)-[1-(5-Chloro-2,3-dimethoxy-phenyl)-ethyl]-(2-methylsulfonyl-5-piperazin-1-yl-phenyl)-amine.

49. [1-(5-Chloro-2,3-dimethoxy-phenyl)-ethyl]-(2-methylsulfonyl-5-piperazin-1-yl-phenyl)-amine hydrochloride.

50. (R)-[1-(5-Chloro-2,3-dimethoxy-phenyl)-ethyl]-(2-methylsulfonyl-5-piperazin-1-yl-phenyl)-amine hydrochloride.

51. (S)-[1-(5-Chloro-2,3-dimethoxy-phenyl)-ethyl]-(2-methylsulfonyl-5-piperazin-1-yl-phenyl)-amine hydrochloride.

52. A pharmaceutical composition comprising [1-(5-Chloro-2,3-dimethoxy-phenyl)-ethyl]-(2-methylsulfonyl-5-piperazin-1-yl-phenyl)-amine.

53. A pharmaceutical composition comprising (R)-[1-(5-Chloro-2,3-dimethoxy-phenyl)-ethyl]-(2-methylsulfonyl-5-piperazin-1-yl-phenyl)-amine.

54. A pharmaceutical composition comprising (S)-[1-(5-Chloro-2,3-dimethoxy-phenyl)-ethyl]-(2-methylsulfonyl-5-piperazin-1-yl-phenyl)-amine.

55. A pharmaceutical composition comprising a pharmaceutically acceptable salt of [1-(5-Chloro-2,3-dimethoxy-phenyl)-ethyl]-(2-methylsulfonyl-5-piperazin-1-yl-phenyl)-amine.

56. A pharmaceutical composition comprising a pharmaceutically acceptable salt of (R)-[1-(5-Chloro-2,3-dimethoxy-phenyl)-ethyl]-(2-methylsulfonyl-5-piperazin-1-yl-phenyl)-amine.

57. A pharmaceutical composition comprising a pharmaceutically acceptable salt of (S)-[1-(5-Chloro-2,3-dimethoxy-phenyl)-ethyl]-(2-methylsulfonyl-5-piperazin-1-yl-phenyl)-amine.

58. A pharmaceutical composition comprising [1-(5-Chloro-2,3-dimethoxy-phenyl)-ethyl]-(2-methylsulfonyl-5-piperazin-1-yl-phenyl)-amine hydrochloride.

59. A pharmaceutical composition comprising (R)-[1-(5-Chloro-2,3-dimethoxy-phenyl)-ethyl]-(2-methylsulfonyl-5-piperazin-1-yl-phenyl)-amine hydrochloride.

60. A pharmaceutical composition comprising (S)-[1-(5-Chloro-2,3-dimethoxy-phenyl)-ethyl]-(2-methylsulfonyl-5-piperazin-1-yl-phenyl)-amine hydrochloride.

* * * * *